United States Patent
Nae et al.

(10) Patent No.: US 12,296,122 B2
(45) Date of Patent: May 13, 2025

(54) HYBRID DEVICES WITH DIMENSIONS THAT CAN BE ADJUSTED IN VIVO AND METHODS OF MANUFACTURING THEREOF

(71) Applicant: V-Wave Ltd., Caesarea (IL)

(72) Inventors: Nir Nae, Binyamina (IL); Neal Eigler, Agoura Hills, CA (US); Lior Rosen, Zikhron Ya'akov (IL); Erez Rozenfeld, Shoham (IL); Werner Hafelfinger, Thousand Oaks, CA (US); John Wardle, San Clemente, CA (US); James S. Whiting, Los Angeles, CA (US)

(73) Assignee: V-Wave Ltd., Caesarea (IL)

( * ) Notice: Subject to any disclaimer, the term of this patent is extended or adjusted under 35 U.S.C. 154(b) by 0 days.

(21) Appl. No.: 18/917,388

(22) Filed: Oct. 16, 2024

(65) Prior Publication Data

US 2025/0128032 A1 Apr. 24, 2025

Related U.S. Application Data

(60) Provisional application No. 63/591,428, filed on Oct. 18, 2023.

(51) Int. Cl.
*A61M 27/00* (2006.01)

(52) U.S. Cl.
CPC ... *A61M 27/002* (2013.01); *A61M 2205/0216* (2013.01); *A61M 2205/0266* (2013.01); *A61M 2210/125* (2013.01)

(58) Field of Classification Search
CPC ........ A61M 27/002; A61M 2205/0216; A61M 2205/0266; A61M 2210/125
See application file for complete search history.

(56) References Cited

U.S. PATENT DOCUMENTS

| 744,589 A | 11/1903 | Moore |
|---|---|---|
| 3,852,334 A | 12/1974 | Dusza et al. |

(Continued)

FOREIGN PATENT DOCUMENTS

| AU | 2003291117 B2 | 4/2009 |
|---|---|---|
| CA | 2378920 A1 | 2/2001 |

(Continued)

OTHER PUBLICATIONS

U.S. Appl. No. 09/839,643 / U.S. Pat. No. 8,091,556, filed Apr. 20, 2001 / Jan. 10, 2012.

(Continued)

*Primary Examiner* — Susan S Su
*Assistant Examiner* — Erin A Kim
(74) *Attorney, Agent, or Firm* — Greenberg Traurig, LLP; Christopher C. Bolten; Albert K. Heng

(57) ABSTRACT

Devices are provided with an internal dimension that can be reduced and increased in vivo. In one example, an interatrial shunt for placement at an atrial septum of a patient's heart includes a body. The body includes first and second regions coupled in fluid communication by a neck region. The body includes a shape-memory material. The body defines a passageway through the neck region for blood to flow between a first atrium and a second atrium. The first and second regions are superelastic at body temperature, and the neck region is malleable at body temperature. A flow area of the passageway through the neck region may be adjusted in vivo.

30 Claims, 38 Drawing Sheets

(56) References Cited

U.S. PATENT DOCUMENTS

| | | |
|---|---|---|
| 3,874,388 A | 4/1975 | King et al. |
| 3,952,334 A | 4/1976 | Bokros et al. |
| 4,364,395 A | 12/1982 | Redmond et al. |
| 4,484,955 A | 11/1984 | Hochstein |
| 4,601,309 A | 7/1986 | Chang |
| 4,617,932 A | 10/1986 | Kornberg |
| 4,662,355 A | 5/1987 | Pieronne et al. |
| 4,665,906 A | 5/1987 | Jervis |
| 4,705,507 A | 11/1987 | Boyles |
| 4,836,204 A | 6/1989 | Landymore et al. |
| 4,979,955 A | 12/1990 | Smith |
| 4,988,339 A | 1/1991 | Vadher |
| 4,995,857 A | 2/1991 | Arnold |
| 5,035,702 A | 7/1991 | Taheri |
| 5,035,706 A | 7/1991 | Giantureo et al. |
| 5,037,427 A | 8/1991 | Harada et al. |
| 5,089,005 A | 2/1992 | Harada |
| 5,108,420 A | 4/1992 | Marks |
| 5,186,431 A | 2/1993 | Tamari |
| 5,197,978 A | 3/1993 | Hess |
| 5,234,447 A | 8/1993 | Kaster et al. |
| 5,267,940 A | 12/1993 | Moulder |
| 5,290,227 A | 3/1994 | Pasque |
| 5,312,341 A | 5/1994 | Turi |
| 5,326,374 A | 7/1994 | Ilbawi et al. |
| 5,332,402 A | 7/1994 | Teitelbaum |
| 5,334,217 A | 8/1994 | Das |
| 5,378,239 A | 1/1995 | Termin et al. |
| 5,409,019 A | 4/1995 | Wilk |
| 5,429,144 A | 7/1995 | Wilk |
| 5,479,945 A | 1/1996 | Simon |
| 5,500,015 A | 3/1996 | Deac |
| 5,531,759 A | 7/1996 | Kensey et al. |
| 5,545,210 A | 8/1996 | Hess et al. |
| 5,556,386 A | 9/1996 | Todd |
| 5,578,008 A | 11/1996 | Hara |
| 5,584,803 A | 12/1996 | Stevens et al. |
| 5,597,377 A | 1/1997 | Aldea |
| 5,645,559 A | 7/1997 | Hachtman et al. |
| 5,655,548 A | 8/1997 | Nelson et al. |
| 5,662,711 A | 9/1997 | Douglas |
| 5,702,412 A | 12/1997 | Popov et al. |
| 5,725,552 A | 3/1998 | Kotula et al. |
| 5,741,324 A | 4/1998 | Glastra |
| 5,749,880 A | 5/1998 | Banas et al. |
| 5,779,716 A | 7/1998 | Cano et al. |
| 5,795,307 A | 8/1998 | Krueger |
| 5,810,836 A | 9/1998 | Hussein et al. |
| 5,824,062 A | 10/1998 | Patke et al. |
| 5,824,071 A | 10/1998 | Nelson et al. |
| 5,846,261 A | 12/1998 | Kotula et al. |
| 5,910,144 A | 6/1999 | Hayashi |
| 5,916,193 A | 6/1999 | Stevens et al. |
| 5,941,850 A | 8/1999 | Shah et al. |
| 5,951,583 A | 9/1999 | Jensen et al. |
| 5,957,949 A | 9/1999 | Leonhardt et al. |
| 5,990,379 A | 11/1999 | Gregory |
| 6,007,544 A | 12/1999 | Kim |
| 6,027,518 A | 2/2000 | Gaber |
| 6,039,755 A | 3/2000 | Edwin et al. |
| 6,039,759 A | 3/2000 | Carpentier et al. |
| 6,059,810 A | 5/2000 | Brown et al. |
| 6,086,610 A | 7/2000 | Duerig et al. |
| 6,111,520 A | 8/2000 | Allen et al. |
| 6,117,159 A | 9/2000 | Huebsch et al. |
| 6,120,534 A | 9/2000 | Ruiz |
| 6,124,523 A | 9/2000 | Banas et al. |
| 6,126,686 A | 10/2000 | Badylak et al. |
| 6,165,188 A | 12/2000 | Saadat et al. |
| 6,210,318 B1 | 4/2001 | Lederman |
| 6,214,029 B1 | 4/2001 | Thill et al. |
| 6,214,039 B1 | 4/2001 | Banas et al. |
| 6,217,541 B1 | 4/2001 | Yu |
| 6,221,096 B1 | 4/2001 | Aiba et al. |
| 6,231,587 B1 | 5/2001 | Makower |
| 6,242,762 B1 | 6/2001 | Brown et al. |
| 6,245,099 B1 | 6/2001 | Edwin et al. |
| 6,254,564 B1 | 7/2001 | Wilk et al. |
| 6,260,552 B1 | 7/2001 | Mortier et al. |
| 6,264,684 B1 | 7/2001 | Banas et al. |
| 6,270,515 B1 | 8/2001 | Linden et al. |
| 6,270,526 B1 | 8/2001 | Cox |
| 6,277,078 B1 | 8/2001 | Porat et al. |
| 6,278,379 B1 | 8/2001 | Allen et al. |
| 6,290,728 B1 | 9/2001 | Phelps et al. |
| 6,302,892 B1 | 10/2001 | Wilk |
| 6,306,141 B1 | 10/2001 | Jervis |
| 6,328,699 B1 | 12/2001 | Eigler et al. |
| 6,344,022 B1 | 2/2002 | Jarvik |
| 6,358,277 B1 | 3/2002 | Duran |
| 6,391,036 B1 | 5/2002 | Berg et al. |
| 6,398,803 B1 | 6/2002 | Layne et al. |
| 6,406,422 B1 | 6/2002 | Landesberg |
| 6,447,539 B1 | 9/2002 | Nelson et al. |
| 6,451,051 B2 | 9/2002 | Drasler et al. |
| 6,458,153 B1 | 10/2002 | Bailey et al. |
| 6,468,303 B1 | 10/2002 | Amplatz et al. |
| 6,475,136 B1 | 11/2002 | Forsell |
| 6,478,776 B1 | 11/2002 | Rosenman et al. |
| 6,485,507 B1 | 11/2002 | Walak et al. |
| 6,488,702 B1 | 12/2002 | Besselink |
| 6,491,705 B2 | 12/2002 | Gifford, III et al. |
| 6,527,698 B1 | 3/2003 | Kung et al. |
| 6,544,208 B2 | 4/2003 | Ethier et al. |
| 6,547,814 B2 | 4/2003 | Edwin et al. |
| 6,562,066 B1 | 5/2003 | Martin |
| 6,572,652 B2 | 6/2003 | Shaknovich |
| 6,579,314 B1 | 6/2003 | Lombardi et al. |
| 6,589,198 B1 | 7/2003 | Soltanpour et al. |
| 6,616,675 B1 | 9/2003 | Evard et al. |
| 6,632,169 B2 | 10/2003 | Korakianitis et al. |
| 6,638,303 B1 | 10/2003 | Campbell |
| 6,641,610 B2 | 11/2003 | Wolf et al. |
| 6,645,220 B1 | 11/2003 | Huter et al. |
| 6,652,578 B2 | 11/2003 | Bailey et al. |
| 6,685,664 B2 | 2/2004 | Levin et al. |
| 6,712,836 B1 | 3/2004 | Berg et al. |
| 6,740,115 B2 | 5/2004 | Lombardi et al. |
| 6,758,858 B2 | 7/2004 | McCrea et al. |
| 6,764,507 B2 | 7/2004 | Shanley et al. |
| 6,770,087 B2 | 8/2004 | Layne et al. |
| 6,797,217 B2 | 9/2004 | McCrea et al. |
| 6,890,350 B1 | 5/2005 | Walak |
| 6,923,829 B2 | 8/2005 | Boyle et al. |
| 6,970,742 B2 | 11/2005 | Mann et al. |
| 7,001,409 B2 | 2/2006 | Amplatz |
| 7,004,966 B2 | 2/2006 | Edwin et al. |
| 7,025,777 B2 | 4/2006 | Moore |
| 7,060,150 B2 | 6/2006 | Banas et al. |
| 7,083,640 B2 | 8/2006 | Lombardi et al. |
| 7,115,095 B2 | 10/2006 | Eigler et al. |
| 7,118,600 B2 | 10/2006 | Dua et al. |
| 7,137,953 B2 | 11/2006 | Eigler et al. |
| 7,147,604 B1 | 12/2006 | Allen et al. |
| 7,149,587 B2 | 12/2006 | Wardle et al. |
| 7,169,160 B1 | 1/2007 | Middleman et al. |
| 7,169,172 B2 | 1/2007 | Levine et al. |
| 7,195,594 B2 | 3/2007 | Eigler et al. |
| 7,208,010 B2 | 4/2007 | Shanley et al. |
| 7,226,558 B2 | 6/2007 | Nieman et al. |
| 7,245,117 B1 | 7/2007 | Joy et al. |
| 7,294,115 B2 | 11/2007 | Wilk |
| 7,306,756 B2 | 12/2007 | Edwin et al. |
| 7,402,899 B1 | 7/2008 | Whiting et al. |
| 7,439,723 B2 | 10/2008 | Allen et al. |
| 7,468,071 B2 | 12/2008 | Edwin et al. |
| 7,483,743 B2 | 1/2009 | Mann et al. |
| 7,498,799 B2 | 3/2009 | Allen et al. |
| 7,509,169 B2 | 3/2009 | Eigler et al. |
| 7,550,978 B2 | 6/2009 | Joy et al. |
| 7,578,899 B2 | 8/2009 | Edwin et al. |
| 7,590,449 B2 | 9/2009 | Mann et al. |
| 7,615,010 B1 | 11/2009 | Najafi et al. |
| 7,621,879 B2 | 11/2009 | Eigler et al. |

(56) References Cited

U.S. PATENT DOCUMENTS

| | | |
|---|---|---|
| 7,679,355 B2 | 3/2010 | Allen et al. |
| 7,717,854 B2 | 5/2010 | Mann et al. |
| 7,794,473 B2 | 9/2010 | Tessmer et al. |
| 7,839,153 B2 | 11/2010 | Joy et al. |
| 7,842,083 B2 | 11/2010 | Shanley et al. |
| 7,854,172 B2 | 12/2010 | O'Brien et al. |
| 7,862,513 B2 | 1/2011 | Eigler et al. |
| 7,914,639 B2 | 3/2011 | Layne et al. |
| 7,939,000 B2 | 5/2011 | Edwin et al. |
| 7,988,724 B2 | 8/2011 | Salahieh et al. |
| 7,993,383 B2 | 8/2011 | Hartley et al. |
| 8,012,194 B2 | 9/2011 | Edwin et al. |
| 8,016,877 B2 | 9/2011 | Seguin et al. |
| 8,021,420 B2 | 9/2011 | Dolan |
| 8,025,625 B2 | 9/2011 | Allen |
| 8,025,668 B2 | 9/2011 | McCartney |
| 8,043,360 B2 | 10/2011 | McNamara et al. |
| 8,070,708 B2 | 12/2011 | Rottenberg et al. |
| 8,091,556 B2 | 1/2012 | Keren et al. |
| 8,096,959 B2 | 1/2012 | Stewart et al. |
| 8,137,605 B2 | 3/2012 | McCrea et al. |
| 8,142,363 B1 | 3/2012 | Eigler et al. |
| 8,147,545 B2 | 4/2012 | Avior |
| 8,157,852 B2 | 4/2012 | Bloom et al. |
| 8,157,860 B2 | 4/2012 | McNamara et al. |
| 8,157,940 B2 | 4/2012 | Edwin et al. |
| 8,158,041 B2 | 4/2012 | Colone |
| 8,187,321 B2 | 5/2012 | Shanley et al. |
| 8,202,313 B2 | 6/2012 | Shanley et al. |
| 8,206,435 B2 | 6/2012 | Shanley et al. |
| 8,216,398 B2 | 7/2012 | Bledsoe et al. |
| 8,235,916 B2 | 8/2012 | Whiting et al. |
| 8,235,933 B2 | 8/2012 | Keren et al. |
| 8,246,677 B2 | 8/2012 | Ryan |
| 8,287,589 B2 | 10/2012 | Otto et al. |
| 8,298,150 B2 | 10/2012 | Mann et al. |
| 8,298,244 B2 | 10/2012 | Garcia et al. |
| 8,303,511 B2 | 11/2012 | Eigler et al. |
| 8,313,524 B2 | 11/2012 | Edwin et al. |
| 8,328,751 B2 | 12/2012 | Keren et al. |
| 8,337,650 B2 | 12/2012 | Edwin et al. |
| 8,348,996 B2 | 1/2013 | Tuval et al. |
| 8,357,193 B2 | 1/2013 | Phan et al. |
| 8,398,708 B2 | 3/2013 | Meiri et al. |
| 8,460,366 B2 | 6/2013 | Rowe |
| 8,468,667 B2 | 6/2013 | Straubinger et al. |
| 8,480,594 B2 | 7/2013 | Eigler et al. |
| 8,579,966 B2 | 11/2013 | Seguin et al. |
| 8,597,225 B2 | 12/2013 | Kapadia |
| 8,617,337 B2 | 12/2013 | Layne et al. |
| 8,617,441 B2 | 12/2013 | Edwin et al. |
| 8,652,284 B2 | 2/2014 | Bogert et al. |
| 8,660,667 B1 | 2/2014 | Kusumoto |
| 8,665,086 B2 | 3/2014 | Miller et al. |
| 8,696,611 B2 | 4/2014 | Nitzan et al. |
| 8,790,241 B2 | 7/2014 | Edwin et al. |
| 8,882,697 B2 | 11/2014 | Celermajer et al. |
| 8,882,798 B2 | 11/2014 | Schwab et al. |
| 8,911,489 B2 | 12/2014 | Ben-Muvhar |
| 9,005,155 B2 | 4/2015 | Sugimoto |
| 9,034,034 B2 | 5/2015 | Nitzan et al. |
| 9,055,917 B2 | 6/2015 | Mann et al. |
| 9,060,696 B2 | 6/2015 | Eigler et al. |
| 9,067,050 B2 | 6/2015 | Gallagher et al. |
| 9,205,236 B2 | 12/2015 | McNamara et al. |
| 9,220,429 B2 | 12/2015 | Nabutovsky et al. |
| 9,232,997 B2 | 1/2016 | Sugimoto et al. |
| 9,358,371 B2 | 6/2016 | McNamara et al. |
| 9,393,115 B2 | 7/2016 | Tabor et al. |
| 9,456,812 B2 | 10/2016 | Finch et al. |
| 9,622,895 B2 | 4/2017 | Cohen et al. |
| 9,629,715 B2 | 4/2017 | Nitzan et al. |
| 9,681,948 B2 | 6/2017 | Levi et al. |
| 9,707,382 B2 | 7/2017 | Nitzan et al. |
| 9,713,696 B2 | 7/2017 | Yacoby et al. |
| 9,724,499 B2 | 8/2017 | Rottenberg et al. |
| 9,757,107 B2 | 9/2017 | McNamara et al. |
| 9,789,294 B2 | 10/2017 | Taft et al. |
| 9,918,677 B2 | 3/2018 | Eigler et al. |
| 9,943,670 B2 | 4/2018 | Keren et al. |
| 9,980,815 B2 | 5/2018 | Nitzan et al. |
| 10,045,766 B2 | 8/2018 | McNamara et al. |
| 10,047,421 B2 | 8/2018 | Khan et al. |
| 10,076,403 B1 | 9/2018 | Eigler et al. |
| 10,105,103 B2 | 10/2018 | Goldshtein et al. |
| 10,111,741 B2 | 10/2018 | Michalak |
| 10,207,087 B2 | 2/2019 | Keren et al. |
| 10,207,807 B2 | 2/2019 | Moran et al. |
| 10,251,740 B2 | 4/2019 | Eigler et al. |
| 10,251,750 B2 | 4/2019 | Alexander et al. |
| 10,265,169 B2 | 4/2019 | Desrosiers et al. |
| 10,299,687 B2 | 5/2019 | Nabutovsky et al. |
| 10,357,320 B2 | 7/2019 | Beira |
| 10,357,357 B2 | 7/2019 | Levi et al. |
| 10,368,981 B2 | 8/2019 | Nitzan et al. |
| 10,463,490 B2 | 11/2019 | Rottenberg et al. |
| 10,478,594 B2 | 11/2019 | Yacoby et al. |
| 10,542,994 B2 | 1/2020 | Ben-Muvhar et al. |
| 10,548,725 B2 | 2/2020 | Alkhatib et al. |
| 10,561,423 B2 | 2/2020 | Sharma |
| 10,583,002 B2 | 3/2020 | Lane et al. |
| 10,639,459 B2 | 5/2020 | Nitzan et al. |
| 10,828,151 B2 | 11/2020 | Nitzan et al. |
| 10,835,394 B2 | 11/2020 | Nae et al. |
| 10,898,698 B1 | 1/2021 | Eigler et al. |
| 10,912,645 B2 | 2/2021 | Rottenberg et al. |
| 10,925,706 B2 | 2/2021 | Eigler et al. |
| 10,940,296 B2 | 3/2021 | Keren |
| 11,109,988 B2 | 9/2021 | Rosen et al. |
| 11,135,054 B2 | 10/2021 | Nitzan et al. |
| 11,234,702 B1 | 2/2022 | Eigler et al. |
| 11,253,353 B2 | 2/2022 | Levi et al. |
| 11,255,379 B2 | 2/2022 | Baskin et al. |
| 11,291,807 B2 | 4/2022 | Eigler et al. |
| 11,304,831 B2 | 4/2022 | Nae et al. |
| 11,382,747 B2 | 7/2022 | Rottenberg et al. |
| 11,458,287 B2 | 10/2022 | Eigler et al. |
| 11,497,631 B2 | 11/2022 | Rosen et al. |
| 11,607,327 B2 | 3/2023 | Nae et al. |
| 11,612,385 B2 | 3/2023 | Nae et al. |
| 11,690,976 B2 | 7/2023 | Yacoby et al. |
| 11,813,386 B2 | 11/2023 | Nae et al. |
| 11,850,138 B2 | 12/2023 | Eigler et al. |
| 11,865,282 B2 | 1/2024 | Nae et al. |
| 12,115,328 B2 | 10/2024 | Nae et al. |
| 12,186,176 B2 | 1/2025 | Eigler et al. |
| 12,186,510 B2 | 1/2025 | Keren |
| 2001/0007956 A1 | 7/2001 | Letac et al. |
| 2001/0020154 A1 | 9/2001 | Bigus et al. |
| 2001/0021872 A1 | 9/2001 | Bailey et al. |
| 2002/0042565 A1 | 4/2002 | Cooper et al. |
| 2002/0051730 A1 | 5/2002 | Bodnar et al. |
| 2002/0099431 A1 | 7/2002 | Armstrong et al. |
| 2002/0120277 A1 | 8/2002 | Hauschild et al. |
| 2002/0165479 A1 | 11/2002 | Wilk |
| 2002/0165606 A1 | 11/2002 | Wolf et al. |
| 2002/0169371 A1 | 11/2002 | Gilderdale |
| 2002/0169377 A1 | 11/2002 | Khairkhahan et al. |
| 2002/0173742 A1 | 11/2002 | Keren et al. |
| 2002/0183628 A1 | 12/2002 | Reich et al. |
| 2003/0028213 A1 | 2/2003 | Thill et al. |
| 2003/0045902 A1 | 3/2003 | Weadock |
| 2003/0097172 A1 | 5/2003 | Shalev et al. |
| 2003/0100920 A1 | 5/2003 | Akin et al. |
| 2003/0125798 A1 | 7/2003 | Martin |
| 2003/0136417 A1 | 7/2003 | Fonseca et al. |
| 2003/0139819 A1 | 7/2003 | Beer et al. |
| 2003/0176914 A1 | 9/2003 | Rabkin et al. |
| 2003/0209835 A1 | 11/2003 | Chun et al. |
| 2003/0216679 A1 | 11/2003 | Wolf et al. |
| 2003/0216803 A1 | 11/2003 | Ledergerber |
| 2004/0010219 A1 | 1/2004 | McCusker et al. |
| 2004/0016514 A1 | 1/2004 | Nien |
| 2004/0073242 A1 | 4/2004 | Chanduszko |

(56) References Cited

U.S. PATENT DOCUMENTS

| | | |
|---|---|---|
| 2004/0077988 A1 | 4/2004 | Tweden et al. |
| 2004/0087984 A1 | 5/2004 | Kupiecki et al. |
| 2004/0088045 A1 | 5/2004 | Cox |
| 2004/0093075 A1 | 5/2004 | Kuehne |
| 2004/0102797 A1 | 5/2004 | Golden et al. |
| 2004/0116999 A1 | 6/2004 | Ledergerber |
| 2004/0138743 A1 | 7/2004 | Myers et al. |
| 2004/0147869 A1 | 7/2004 | Wolf et al. |
| 2004/0147871 A1 | 7/2004 | Burnett |
| 2004/0147886 A1 | 7/2004 | Bonni |
| 2004/0147969 A1 | 7/2004 | Mann et al. |
| 2004/0162514 A1 | 8/2004 | Alferness et al. |
| 2004/0193261 A1 | 9/2004 | Berreklouw |
| 2004/0210190 A1 | 10/2004 | Kohler et al. |
| 2004/0210307 A1 | 10/2004 | Khairkhahan |
| 2004/0225352 A1 | 11/2004 | Osborne et al. |
| 2005/0003327 A1 | 1/2005 | Elian et al. |
| 2005/0033327 A1 | 2/2005 | Gainor et al. |
| 2005/0033351 A1 | 2/2005 | Newton |
| 2005/0065589 A1 | 3/2005 | Schneider et al. |
| 2005/0125032 A1 | 6/2005 | Whisenant et al. |
| 2005/0137682 A1 | 6/2005 | Justino |
| 2005/0148925 A1 | 7/2005 | Rottenberg et al. |
| 2005/0149166 A1 | 7/2005 | Schaeffer et al. |
| 2005/0165344 A1 | 7/2005 | Dobak |
| 2005/0182486 A1 | 8/2005 | Gabbay |
| 2005/0228480 A1 | 10/2005 | Douglas et al. |
| 2005/0267524 A1 | 12/2005 | Chanduszko |
| 2005/0283231 A1 | 12/2005 | Haug et al. |
| 2005/0288596 A1 | 12/2005 | Eigler et al. |
| 2005/0288706 A1 | 12/2005 | Widomski et al. |
| 2005/0288786 A1 | 12/2005 | Chanduszko |
| 2006/0009800 A1 | 1/2006 | Christianson et al. |
| 2006/0025857 A1 | 2/2006 | Bergheim et al. |
| 2006/0052821 A1 | 3/2006 | Abbott et al. |
| 2006/0106449 A1 | 5/2006 | Ben Muvhar |
| 2006/0111660 A1 | 5/2006 | Wolf et al. |
| 2006/0111704 A1 | 5/2006 | Brenneman et al. |
| 2006/0116710 A1 | 6/2006 | Corcoran et al. |
| 2006/0122522 A1 | 6/2006 | Chavan et al. |
| 2006/0122647 A1 | 6/2006 | Callaghan et al. |
| 2006/0167541 A1 | 7/2006 | Lattouf |
| 2006/0184231 A1 | 8/2006 | Rucker |
| 2006/0212110 A1 | 9/2006 | Osborne et al. |
| 2006/0241745 A1 | 10/2006 | Solem |
| 2006/0256611 A1 | 11/2006 | Bednorz et al. |
| 2006/0282157 A1 | 12/2006 | Hill et al. |
| 2007/0010852 A1 | 1/2007 | Blaeser et al. |
| 2007/0021739 A1 | 1/2007 | Weber |
| 2007/0043435 A1 | 2/2007 | Seguin et al. |
| 2007/0073337 A1 | 3/2007 | Abbott et al. |
| 2007/0129756 A1 | 6/2007 | Abbott et al. |
| 2007/0191863 A1 | 8/2007 | De Juan, Jr. et al. |
| 2007/0213813 A1 | 9/2007 | Von Segesser et al. |
| 2007/0249985 A1 | 10/2007 | Brenneman et al. |
| 2007/0276413 A1 | 11/2007 | Nobles |
| 2007/0276414 A1 | 11/2007 | Nobles |
| 2007/0282157 A1 | 12/2007 | Rottenberg et al. |
| 2007/0299384 A1 | 12/2007 | Faul et al. |
| 2008/0034836 A1 | 2/2008 | Eigler et al. |
| 2008/0086205 A1 | 4/2008 | Gordy et al. |
| 2008/0125861 A1 | 5/2008 | Webler et al. |
| 2008/0171944 A1 | 7/2008 | Brenneman et al. |
| 2008/0177300 A1 | 7/2008 | Mas et al. |
| 2008/0221609 A1 | 9/2008 | McGuckin et al. |
| 2008/0243081 A1 | 10/2008 | Nance et al. |
| 2008/0262602 A1 | 10/2008 | Wilk et al. |
| 2008/0264102 A1 | 10/2008 | Berra |
| 2008/0319525 A1 | 12/2008 | Tieu et al. |
| 2009/0030499 A1 | 1/2009 | Bebb et al. |
| 2009/0054976 A1 | 2/2009 | Tuval et al. |
| 2009/0125104 A1 | 5/2009 | Hoffman |
| 2009/0149947 A1 | 6/2009 | Frohwitter |
| 2009/0198315 A1 | 8/2009 | Boudjemline |
| 2009/0248133 A1* | 10/2009 | Bloom ............ A61F 2/91 623/1.15 |
| 2009/0276040 A1 | 11/2009 | Rowe et al. |
| 2009/0319037 A1 | 12/2009 | Rowe et al. |
| 2010/0004740 A1 | 1/2010 | Seguin et al. |
| 2010/0022940 A1 | 1/2010 | Thompson |
| 2010/0023046 A1 | 1/2010 | Heidner et al. |
| 2010/0057192 A1 | 3/2010 | Celermajer |
| 2010/0069836 A1 | 3/2010 | Satake |
| 2010/0070022 A1 | 3/2010 | Kuehling |
| 2010/0081867 A1 | 4/2010 | Fishler et al. |
| 2010/0100167 A1 | 4/2010 | Bortlein et al. |
| 2010/0121434 A1 | 5/2010 | Paul et al. |
| 2010/0125288 A1 | 5/2010 | Gelfand et al. |
| 2010/0179590 A1 | 7/2010 | Fortson et al. |
| 2010/0191326 A1 | 7/2010 | Alkhatib |
| 2010/0249491 A1 | 9/2010 | Farnan et al. |
| 2010/0249909 A1 | 9/2010 | McNamara et al. |
| 2010/0249910 A1 | 9/2010 | McNamara et al. |
| 2010/0249915 A1 | 9/2010 | Zhang |
| 2010/0256548 A1 | 10/2010 | McNamara et al. |
| 2010/0256753 A1 | 10/2010 | McNamara et al. |
| 2010/0298632 A1 | 11/2010 | Levine et al. |
| 2010/0298755 A1 | 11/2010 | McNamara et al. |
| 2010/0324652 A1 | 12/2010 | Aurilia et al. |
| 2011/0022057 A1 | 1/2011 | Eigler et al. |
| 2011/0022157 A1 | 1/2011 | Essinger et al. |
| 2011/0054515 A1 | 3/2011 | Bridgeman et al. |
| 2011/0071623 A1 | 3/2011 | Finch et al. |
| 2011/0071624 A1 | 3/2011 | Finch et al. |
| 2011/0093059 A1 | 4/2011 | Fischell et al. |
| 2011/0106149 A1 | 5/2011 | Ryan et al. |
| 2011/0152923 A1 | 6/2011 | Fox |
| 2011/0190874 A1 | 8/2011 | Celermajer et al. |
| 2011/0218479 A1 | 9/2011 | Rottenberg et al. |
| 2011/0218480 A1 | 9/2011 | Rottenberg et al. |
| 2011/0218481 A1 | 9/2011 | Rottenberg et al. |
| 2011/0218613 A1 | 9/2011 | Leopold et al. |
| 2011/0251675 A1 | 10/2011 | Dwork |
| 2011/0257723 A1 | 10/2011 | McNamara |
| 2011/0264191 A1 | 10/2011 | Rothstein |
| 2011/0264203 A1 | 10/2011 | Dwork et al. |
| 2011/0276086 A1 | 11/2011 | Al-Qbandi et al. |
| 2011/0295182 A1 | 12/2011 | Finch et al. |
| 2011/0295183 A1 | 12/2011 | Finch et al. |
| 2011/0295362 A1 | 12/2011 | Finch et al. |
| 2011/0295366 A1 | 12/2011 | Finch et al. |
| 2011/0306916 A1 | 12/2011 | Nitzan et al. |
| 2011/0319806 A1 | 12/2011 | Wardle |
| 2012/0022507 A1 | 1/2012 | Najafi et al. |
| 2012/0022633 A1 | 1/2012 | Olson et al. |
| 2012/0035590 A1 | 2/2012 | Whiting et al. |
| 2012/0041422 A1 | 2/2012 | Whiting et al. |
| 2012/0046528 A1 | 2/2012 | Eigler et al. |
| 2012/0046739 A1 | 2/2012 | Von Oepen et al. |
| 2012/0053686 A1 | 3/2012 | McNamara et al. |
| 2012/0071918 A1 | 3/2012 | Amin et al. |
| 2012/0130301 A1 | 5/2012 | McNamara et al. |
| 2012/0165928 A1 | 6/2012 | Nitzan et al. |
| 2012/0179172 A1 | 7/2012 | Paul, Jr. et al. |
| 2012/0190991 A1 | 7/2012 | Bornzin et al. |
| 2012/0265296 A1 | 10/2012 | McNamara et al. |
| 2012/0271277 A1 | 10/2012 | Fischell et al. |
| 2012/0271398 A1 | 10/2012 | Essinger et al. |
| 2012/0289882 A1 | 11/2012 | McNamara et al. |
| 2012/0290062 A1 | 11/2012 | McNamara et al. |
| 2013/0030521 A1 | 1/2013 | Nitzan et al. |
| 2013/0046373 A1 | 2/2013 | Cartledge et al. |
| 2013/0096965 A1 | 4/2013 | Pappas et al. |
| 2013/0138145 A1 | 5/2013 | Von Oepen |
| 2013/0178783 A1 | 7/2013 | McNamara et al. |
| 2013/0178784 A1 | 7/2013 | McNamara et al. |
| 2013/0184633 A1 | 7/2013 | McNamara et al. |
| 2013/0184634 A1 | 7/2013 | McNamara et al. |
| 2013/0197423 A1 | 8/2013 | Keren et al. |
| 2013/0197547 A1 | 8/2013 | Fukuoka et al. |
| 2013/0197629 A1 | 8/2013 | Gainor et al. |
| 2013/0204175 A1 | 8/2013 | Sugimoto |
| 2013/0231737 A1 | 9/2013 | McNamara et al. |

(56) References Cited

U.S. PATENT DOCUMENTS

| | | |
|---|---|---|
| 2013/0253342 A1 | 9/2013 | Griswold et al. |
| 2013/0261531 A1 | 10/2013 | Gallagher et al. |
| 2013/0281988 A1 | 10/2013 | Magnin et al. |
| 2013/0304192 A1 | 11/2013 | Chanduszko |
| 2013/0331864 A1 | 12/2013 | Jelich et al. |
| 2014/0012181 A1 | 1/2014 | Sugimoto et al. |
| 2014/0012303 A1 | 1/2014 | Heipl |
| 2014/0012368 A1 | 1/2014 | Sugimoto et al. |
| 2014/0012369 A1 | 1/2014 | Murry, III et al. |
| 2014/0039599 A1 | 2/2014 | Berreklouw |
| 2014/0067037 A1 | 3/2014 | Fargahi |
| 2014/0094904 A1 | 4/2014 | Salahieh et al. |
| 2014/0128795 A1 | 5/2014 | Keren et al. |
| 2014/0128796 A1 | 5/2014 | Keren et al. |
| 2014/0163449 A1 | 6/2014 | Rottenberg et al. |
| 2014/0194971 A1 | 7/2014 | McNamara |
| 2014/0213959 A1 | 7/2014 | Nitzan et al. |
| 2014/0222144 A1 | 8/2014 | Eberhardt et al. |
| 2014/0249621 A1 | 9/2014 | Eidenschink |
| 2014/0257167 A1 | 9/2014 | Celermajer |
| 2014/0275916 A1 | 9/2014 | Nabutovsky et al. |
| 2014/0277045 A1 | 9/2014 | Fazio et al. |
| 2014/0277054 A1 | 9/2014 | McNamara et al. |
| 2014/0303710 A1 | 10/2014 | Zhang et al. |
| 2014/0350565 A1 | 11/2014 | Yacoby et al. |
| 2014/0350658 A1 | 11/2014 | Benary et al. |
| 2014/0350661 A1 | 11/2014 | Schaeffer |
| 2014/0350669 A1 | 11/2014 | Gillespie et al. |
| 2014/0357946 A1 | 12/2014 | Golden et al. |
| 2014/0364941 A1 | 12/2014 | Edmiston et al. |
| 2015/0005810 A1 | 1/2015 | Center et al. |
| 2015/0034217 A1 | 2/2015 | Vad |
| 2015/0039084 A1 | 2/2015 | Levi et al. |
| 2015/0066140 A1 | 3/2015 | Quadri et al. |
| 2015/0073539 A1 | 3/2015 | Geiger et al. |
| 2015/0112383 A1 | 4/2015 | Sherman et al. |
| 2015/0119796 A1 | 4/2015 | Finch |
| 2015/0127093 A1 | 5/2015 | Hosmer et al. |
| 2015/0142049 A1 | 5/2015 | Delgado et al. |
| 2015/0148731 A1 | 5/2015 | McNamara et al. |
| 2015/0148896 A1 | 5/2015 | Karapetian et al. |
| 2015/0157455 A1 | 6/2015 | Hoang et al. |
| 2015/0173897 A1 | 6/2015 | Raanani et al. |
| 2015/0182334 A1 | 7/2015 | Bourang et al. |
| 2015/0190229 A1 | 7/2015 | Seguin |
| 2015/0196383 A1 | 7/2015 | Johnson |
| 2015/0201998 A1 | 7/2015 | Roy et al. |
| 2015/0209143 A1 | 7/2015 | Duffy et al. |
| 2015/0230924 A1 | 8/2015 | Miller et al. |
| 2015/0238314 A1 | 8/2015 | Bortlein et al. |
| 2015/0245908 A1 | 9/2015 | Nitzan et al. |
| 2015/0272731 A1 | 10/2015 | Racchini et al. |
| 2015/0282790 A1 | 10/2015 | Quinn et al. |
| 2015/0282931 A1 | 10/2015 | Brunnett et al. |
| 2015/0294313 A1 | 10/2015 | Kamal et al. |
| 2015/0297346 A1 | 10/2015 | Duffy et al. |
| 2015/0313599 A1 | 11/2015 | Johnson et al. |
| 2015/0335801 A1 | 11/2015 | Farnan et al. |
| 2015/0359556 A1 | 12/2015 | Vardi |
| 2016/0007924 A1 | 1/2016 | Eigler et al. |
| 2016/0022423 A1 | 1/2016 | McNamara et al. |
| 2016/0022970 A1 | 1/2016 | Forcucci et al. |
| 2016/0045165 A1 | 2/2016 | Braido et al. |
| 2016/0045311 A1 | 2/2016 | McCann et al. |
| 2016/0073907 A1 | 3/2016 | Nabutovsky et al. |
| 2016/0120550 A1 | 5/2016 | McNamara et al. |
| 2016/0129260 A1 | 5/2016 | Mann et al. |
| 2016/0157862 A1 | 6/2016 | Hernandez et al. |
| 2016/0166381 A1 | 6/2016 | Sugimoto et al. |
| 2016/0184561 A9 | 6/2016 | McNamara et al. |
| 2016/0206423 A1 | 7/2016 | O'Connor et al. |
| 2016/0213467 A1 | 7/2016 | Backus et al. |
| 2016/0220360 A1 | 8/2016 | Lin et al. |
| 2016/0220365 A1 | 8/2016 | Backus et al. |
| 2016/0262878 A1 | 9/2016 | Backus et al. |
| 2016/0262879 A1 | 9/2016 | Meiri et al. |
| 2016/0287386 A1 | 10/2016 | Alon et al. |
| 2016/0296325 A1 | 10/2016 | Edelman et al. |
| 2016/0361167 A1 | 12/2016 | Tuval et al. |
| 2016/0361184 A1 | 12/2016 | Tabor et al. |
| 2017/0028176 A1 | 2/2017 | Dam et al. |
| 2017/0035435 A1 | 2/2017 | Amin et al. |
| 2017/0056171 A1 | 3/2017 | Cooper et al. |
| 2017/0072173 A1 | 3/2017 | Van Dam et al. |
| 2017/0106176 A1 | 4/2017 | Taft et al. |
| 2017/0112624 A1 | 4/2017 | Patel |
| 2017/0113026 A1 | 4/2017 | Finch |
| 2017/0128705 A1 | 5/2017 | Forcucci et al. |
| 2017/0135685 A9 | 5/2017 | McNamara et al. |
| 2017/0165062 A1 | 6/2017 | Rothstein |
| 2017/0165532 A1 | 6/2017 | Khan et al. |
| 2017/0216025 A1 | 8/2017 | Nitzan et al. |
| 2017/0224323 A1 | 8/2017 | Rowe et al. |
| 2017/0224444 A1 | 8/2017 | Viecilli et al. |
| 2017/0231766 A1 | 8/2017 | Hariton et al. |
| 2017/0273790 A1 | 9/2017 | Vettukattil et al. |
| 2017/0281339 A1 | 10/2017 | Levi et al. |
| 2017/0312486 A1 | 11/2017 | Nitzan et al. |
| 2017/0319823 A1 | 11/2017 | Yacoby et al. |
| 2017/0325956 A1 | 11/2017 | Rottenberg et al. |
| 2017/0340460 A1 | 11/2017 | Rosen et al. |
| 2017/0348100 A1 | 12/2017 | Lane et al. |
| 2018/0028314 A1 | 2/2018 | Ekvall et al. |
| 2018/0085128 A1 | 3/2018 | Bellomo et al. |
| 2018/0099128 A9 | 4/2018 | McNamara et al. |
| 2018/0104053 A1 | 4/2018 | Alkhatib et al. |
| 2018/0110609 A1 | 4/2018 | Ehnes et al. |
| 2018/0116843 A1 | 5/2018 | Schreck et al. |
| 2018/0125630 A1 | 5/2018 | Hynes et al. |
| 2018/0130988 A1 | 5/2018 | Nishikawa et al. |
| 2018/0153691 A1 | 6/2018 | Anderson et al. |
| 2018/0200496 A1 | 7/2018 | Kratzberg et al. |
| 2018/0243071 A1 | 8/2018 | Eigler et al. |
| 2018/0256865 A1 | 9/2018 | Finch et al. |
| 2018/0263766 A1 | 9/2018 | Nitzan et al. |
| 2018/0280667 A1 | 10/2018 | Keren |
| 2018/0280668 A1 | 10/2018 | Alaswad |
| 2018/0344994 A1 | 12/2018 | Karavany et al. |
| 2019/0000327 A1 | 1/2019 | Doan et al. |
| 2019/0008628 A1 | 1/2019 | Eigler et al. |
| 2019/0015103 A1 | 1/2019 | Sharma |
| 2019/0015188 A1 | 1/2019 | Eigler et al. |
| 2019/0021861 A1 | 1/2019 | Finch |
| 2019/0083076 A1 | 3/2019 | Alanbaei |
| 2019/0110911 A1 | 4/2019 | Nae et al. |
| 2019/0239754 A1 | 8/2019 | Nabutovsky et al. |
| 2019/0254814 A1 | 8/2019 | Nitzan et al. |
| 2019/0262118 A1 | 8/2019 | Eigler et al. |
| 2019/0328513 A1 | 10/2019 | Levi et al. |
| 2019/0336163 A1 | 11/2019 | McNamara et al. |
| 2020/0060825 A1 | 2/2020 | Rottenberg et al. |
| 2020/0078196 A1 | 3/2020 | Rosen et al. |
| 2020/0078558 A1 | 3/2020 | Yacoby et al. |
| 2020/0085600 A1 | 3/2020 | Schwartz et al. |
| 2020/0197178 A1* | 6/2020 | Vecchio .............. A61B 5/4839 |
| 2020/0261705 A1 | 8/2020 | Nitzan et al. |
| 2020/0315599 A1 | 10/2020 | Nae et al. |
| 2020/0368505 A1 | 11/2020 | Nae et al. |
| 2021/0022507 A1 | 1/2021 | Williams |
| 2021/0052378 A1 | 2/2021 | Nitzan et al. |
| 2021/0100665 A1 | 4/2021 | Nae et al. |
| 2021/0121179 A1 | 4/2021 | Ben-David et al. |
| 2021/0205590 A1 | 7/2021 | Fahey et al. |
| 2021/0338990 A1 | 11/2021 | Eigler et al. |
| 2022/0008014 A1 | 1/2022 | Rowe et al. |
| 2022/0151784 A1 | 5/2022 | Eigler et al. |
| 2022/0211361 A1 | 7/2022 | Rolando et al. |
| 2022/0304803 A1 | 9/2022 | Guyenot et al. |
| 2022/0346935 A1 | 11/2022 | Shermer et al. |

FOREIGN PATENT DOCUMENTS

| | | |
|---|---|---|
| CN | 101505680 A | 8/2009 |
| CN | 105555204 A | 5/2016 |

(56) References Cited

FOREIGN PATENT DOCUMENTS

| | | | |
|---|---|---|---|
| CN | 108451569 A | 8/2018 |
| CN | 113397762 A | 9/2021 |
| EP | 1987777 A2 | 11/2008 |
| EP | 2238933 A1 | 10/2010 |
| EP | 2305321 A1 | 4/2011 |
| EP | 1965842 B1 | 11/2011 |
| EP | 3400907 A1 | 11/2018 |
| FR | 2827153 A1 | 1/2003 |
| WO | WO-9531945 A1 | 11/1995 |
| WO | WO-9702850 A1 | 1/1997 |
| WO | WO-9727898 A1 | 8/1997 |
| WO | WO-9960941 A1 | 12/1999 |
| WO | WO-0044311 A2 | 8/2000 |
| WO | WO-0050100 A1 | 8/2000 |
| WO | WO-0110314 A2 | 2/2001 |
| WO | WO-0126585 A1 | 4/2001 |
| WO | WO-0191828 A2 | 12/2001 |
| WO | WO-0226281 A1 | 4/2002 |
| WO | WO-02071974 A2 | 9/2002 |
| WO | WO-02087473 A1 | 11/2002 |
| WO | WO-03053495 A2 | 7/2003 |
| WO | WO-2005027752 A1 | 3/2005 |
| WO | WO-2005074367 A2 | 8/2005 |
| WO | WO-2006127765 A1 | 11/2006 |
| WO | WO-2007083288 A2 | 7/2007 |
| WO | WO-2008055301 A1 | 5/2008 |
| WO | WO-2008070797 A2 | 6/2008 |
| WO | WO-2009029261 A1 | 3/2009 |
| WO | WO-2010128501 A1 | 11/2010 |
| WO | WO-2010129089 A2 | 11/2010 |
| WO | WO-2010139771 A2 | 12/2010 |
| WO | WO-2010139771 A3 | 1/2011 |
| WO | WO-2011062858 A1 | 5/2011 |
| WO | WO-2013096965 A1 | 6/2013 |
| WO | WO-2013172474 A1 | 11/2013 |
| WO | WO-2016178171 A1 | 11/2016 |
| WO | WO-2017118920 A1 | 7/2017 |
| WO | WO-2018158747 A1 | 9/2018 |
| WO | WO-2019015617 A1 | 1/2019 |
| WO | WO-2019085841 A1 | 5/2019 |
| WO | WO-2019109013 A1 | 6/2019 |
| WO | WO-2019142152 A1 | 7/2019 |
| WO | WO-2019179447 A1 | 9/2019 |
| WO | WO-2019212812 A1 | 11/2019 |
| WO | WO-2019218072 A1 | 11/2019 |
| WO | WO-2020123338 A1 | 6/2020 |
| WO | WO-2020163112 A1 | 8/2020 |
| WO | WO-2020206062 A1 | 10/2020 |
| WO | WO-2020257530 A1 | 12/2020 |
| WO | WO-2021050589 A1 | 3/2021 |
| WO | WO-2021113670 A1 | 6/2021 |
| WO | WO-2021212011 A2 | 10/2021 |
| WO | WO-2021224736 A1 | 11/2021 |
| WO | WO-2022046921 A1 | 3/2022 |
| WO | WO-2022076601 A1 | 4/2022 |
| WO | WO-2022091018 A1 | 5/2022 |
| WO | WO-2022091019 A1 | 5/2022 |
| WO | WO-2022103973 A1 | 5/2022 |
| WO | WO-2023079498 A1 | 5/2023 |

OTHER PUBLICATIONS

U.S. Appl. No. 10/597,666 / U.S. Pat. No. 8,070,708, filed Jun. 20, 2007 / Dec. 6, 2011.
U.S. Appl. No. 12/223,080 / U.S. Pat. No. 9,681,948, filed Jul. 16, 2014 / Jun. 20, 2017.
U.S. Appl. No. 13/107,832 / U.S. Pat. No. 8,235,933, filed May 13, 2011 / Aug. 7, 2012.
U.S. Appl. No. 13/107,843 / U.S. Pat. No. 8,328,751, filed May 13, 2011 / Dec. 11, 2012.
U.S. Appl. No. 13/108,672 / U.S. Pat. No. 9,724,499, filed May 16, 2011 / Aug. 8, 2017.
U.S. Appl. No. 13/108,698, filed Jun. 16, 2011.
U.S. Appl. No. 13/108,850, filed May 16, 2011.
U.S. Appl. No. 13/108,880 / U.S. Pat. No. 8,696,611, filed May 16, 2011 / Apr. 15, 2014.
U.S. Appl. No. 13/193,309 / U.S. Pat. No. 9,629,715, filed Jul. 28, 2011 / Apr. 25, 2017.
U.S. Appl. No. 13/193,335 / U.S. Pat. No. 9,034,034, filed Jul. 28, 2011 / May 19, 2015.
U.S. Appl. No. 13/708,794 / U.S. Pat. No. 9,943,670, filed Dec. 7, 2012 / Apr. 17, 2018.
U.S. Appl. No. 14/154,080 / U.S. Pat. No. 10,207,807, filed Jan. 13, 2014 / Feb. 19, 2019.
U.S. Appl. No. 14/154,088, filed Jan. 13, 2014.
U.S. Appl. No. 14/154,093, filed Jan. 13, 2014.
U.S. Appl. No. 14/227,982 / U.S. Pat. No. 9,707,382, filed Mar. 27, 2014 / Jul. 18, 2017.
U.S. Appl. No. 14/282,615 / U.S. Pat. No. 9,713,696, filed May 20, 2014 / Jul. 25, 2017.
U.S. Appl. No. 14/712,801 / U.S. Pat. No. 9,980,815, filed May 14, 2015 / May 29, 2018.
U.S. Appl. No. 15/449,834 / U.S. Pat. No. 10,076,403, filed Mar. 3, 2017 / Sep. 18, 2018.
U.S. Appl. No. 15/492,852 / U.S. Pat. No. 10,368,981, filed Apr. 20, 2017 / Aug. 6, 2019.
U.S. Appl. No. 15/570,752 / U.S. Pat. No. 10,940,296, filed Oct. 31, 2017 / Mar. 9, 2021.
U.S. Appl. No. 15/608,948, filed May 30, 2017.
U.S. Appl. No. 15/624,314 / U.S. Pat. No. 10,357,357, filed Jun. 15, 2017 / Jul. 23, 2019.
U.S. Appl. No. 15/650,783 / U.S. Pat. No. 10,639,459, filed Jul. 14, 2017 / May 5, 2020.
U.S. Appl. No. 15/656,936 / U.S. Pat. No. 10,478,594, filed Jul. 21, 2017 / Nov. 19, 2019.
U.S. Appl. No. 15/668,622 / U.S. Pat. No. 10,463,490, filed Aug. 3, 2017 / Nov. 5, 2019.
U.S. Appl. No. 15/798,250 / U.S. Pat. No. 11,109,988, filed Oct. 30, 2017 / Sep. 7, 2021.
U.S. Appl. No. 15/988,888 / U.S. Pat. No. 10,828,151, filed May 24, 2018 / Nov. 10, 2020.
U.S. Appl. No. 16/130,978 / U.S. Pat. No. 10,251,740, filed Sep. 13, 2018 / Apr. 9, 2019.
U.S. Appl. No. 16/130,988 / U.S. Pat. No. 10,925,706, filed Sep. 13, 2018 / Feb. 23, 2021.
U.S. Appl. No. 16/205,213 / U.S. Pat. No. 10,835,394, filed Nov. 29, 2018 / Nov. 17, 2020.
U.S. Appl. No. 16/374,698 / U.S. Pat. No. 11,612,385, filed Apr. 3, 2019 / Mar. 28, 2023.
U.S. Appl. No. 16/395,209 / U.S. Pat. No. 11,135,054, filed Apr. 25, 2019 / Oct. 5, 2021.
U.S. Appl. No. 16/408,419 / U.S. Pat. No. 11,291,807, filed May 9, 2019 / Apr. 5, 2022.
U.S. Appl. No. 16/505,624 / U.S. Pat. No. 11,253,353, filed Jul. 8, 2019 / Feb. 22, 2022.
U.S. Appl. No. 16/672,420 / U.S. Pat. No. 11,266,501, filed Nov. 1, 2019 / Mar. 8, 2022.
U.S. Appl. No. 16/686,013 / U.S. Pat. No. 11,690,976, filed Nov. 15, 2019 / Jul. 4, 2023.
U.S. Appl. No. 16/866,377, filed May 4, 2020.
U.S. Appl. No. 16/875,652 / U.S. Pat. No. 10,898,698, filed May 15, 2020 / Jan. 26, 2021.
U.S. Appl. No. 16/876,640 / U.S. Pat. No. 11,865,282, filed May 18, 2020 / Jan. 9, 2024.
U.S. Appl. No. 16/878,228 / U.S. Pat. No. 10,912,645, filed May 19, 2020 / Feb. 9, 2021.
U.S. Appl. No. 16/963,139 / U.S. Pat. No. 11,744,589, filed Jul. 17, 2020 / Sep. 5, 2023.
U.S. Appl. No. 17/092,063, filed Nov. 6, 2020.
U.S. Appl. No. 17/092,081 / U.S. Pat. No. 12,115,328, filed Nov. 6, 2020 / Oct. 15, 2024.
U.S. Appl. No. 17/095,615 / U.S. Pat. No. 11,304,831, filed Nov. 11, 2020 / Apr. 19, 2022.
U.S. Appl. No. 17/098,251 / U.S. Pat. No. 11,234,702, filed Nov. 13, 2020 / Feb. 1, 2022.
U.S. Appl. No. 17/166,771, filed Feb. 3, 2021.

(56) References Cited

OTHER PUBLICATIONS

U.S. Appl. No. 17/175,549, filed Feb. 12, 2021.
U.S. Appl. No. 17/192,612, filed Mar. 4, 2021.
U.S. Appl. No. 17/465,791 / U.S. Pat. No. 11,109,988, filed Sep. 2, 2021 / Nov. 15, 2022.
U.S. Appl. No. 17/490,510, filed Sep. 30, 2021.
U.S. Appl. No. 17/600,079, filed Sep. 29, 2021.
U.S. Appl. No. 17/649,176, filed Jan. 27, 2022.
U.S. Appl. No. 17/649,331, filed Jan. 28, 2022.
U.S. Appl. No. 17/651,409, filed Feb. 16, 2022.
U.S. Appl. No. 17/653,551 / U.S. Pat. No. 11,382,747, filed Mar. 4, 2022 / Jul. 12, 2022.
U.S. Appl. No. 17/656,521, filed Mar. 25, 2022.
U.S. Appl. No. 17/659,312 / U.S. Pat. No. 11,607,327, filed Apr. 14, 2022 / Mar. 21, 2023.
U.S. Appl. No. 17/660,384 / U.S. Pat. No. 11,458,237, filed Apr. 22, 2022 / Oct. 4, 2022.
U.S. Appl. No. 17/805,001, filed Jun. 1, 2022.
U.S. Appl. No. 17/811,476, filed Jul. 8, 2022.
U.S. Appl. No. 17/823,047 / U.S. Pat. No. 11,850,138, filed Aug. 29, 2022 / Dec. 26, 2023.
U.S. Appl. No. 17/997,902, filed Nov. 3, 2022.
U.S. Appl. No. 18/180,068, filed Mar. 7, 2023.
U.S. Appl. No. 18/300,092 / U.S. Pat. No. 11,813,386, filed Apr. 13, 2023 / Nov. 14, 2023.
U.S. Appl. No. 18/320,108, filed May 18, 2023.
U.S. Appl. No. 18/458,642, filed Aug. 30, 2023.
U.S. Appl. No. 18/506,977, filed Nov. 10, 2023.
U.S. Appl. No. 18/634,796, filed Apr. 12, 2024.
U.S. Appl. No. 18/651,630, filed Apr. 30, 2024.
Abraham et al., "Hemodynamic Monitoring in Advanced Heart Failure: Results from the LAPTOP-HF Trial," J Card Failure, 22:940 (2016) (Abstract Only).
Abraham et al., "Sustained efficacy of pulmonary artery pressure to guide adjustment of chronic heart failure therapy: complete follow-up results from the Champion randomised trial," The Lancet, doi.org/10.1016/S0140-6736(15)00723-0 (2015).
Abraham et al., "Wireless pulmonary artery haemodynamic monitoring in chronic heart failure: a randomised controlled trial," The Lancet, DOI:10.1016/S0140-6736(11)60101-3 (2011).
Abreu et al., "Doppler ultrasonography of the femoropopliteal segment in patients with venous ulcer," J Vasc Bras., 11(4):277-285 (2012).
Adamson et al., "Ongoing Right Ventricular Hemodynamics in Heart Failure Clinical Value of Measurements Derived From an Implantable Monitoring System," J Am Coll Cardiol., 41(4):565-571 (2003).
Adamson et al., "Wireless Pulmonary Artery Pressure Monitoring Guides Management to Reduce Decompensation in Heart Failure With Preserved Ejection Fraction," Circ Heart Fail., 7:935-944 (2014).
Ambrosy et al. "The Global Health and Economic Burden of Hospitalizations for Heart Failure," J Am Coll Cardiol., 63:1123-1133 (2014).
Aminde et al., "Current diagnostic and treatment strategies for Lutembacher syndrome: the pivotal role of echocardiography," Cardiovasc Diagn Ther., 5(2):122-132 (2015).
Anderas E. "Advanced MEMS Pressure Sensors Operating in Fluids," Digital Comprehensive Summaries of Uppsala Dissertation from the Faculty of Science and Technology 933. Uppsala ISBN 978-91-554-8369-2 (2014).
Anderas et al., "Tilted c-axis Thin-Film Bulk Wave Resonant Pressure Sensors with Improved Sensitivity," IEEE Sensors J., 12(8):2653-2654 (2012).
Ando, et al., Left ventricular decompression through a patent foramen ovale in a patient with hypertrophic cardiomyopathy: A case report, Cardiovascular Ultrasound, 2: 1-7 (2004).
Article 34 Amendments dated May 28, 2013 in Int'l PCT Patent Appl. Serial No. PCT/IB2012/001859 (0810).
Article 34 Amendments dated Nov. 27, 2012 in Int'l PCT Patent Appl. Serial No. PCT/IL2011/000958 (0710).
Ataya et al., "A Review of Targeted Pulmonary Arterial Hypertension-Specific Pharmacotherapy," J. Clin. Med., 5(12):114 (2016).
"Atrium Advanta V12, Balloon Expandable Covered Stent, Improving Patient Outcomes with An Endovascular Approach," Brochure, 8 pages, Getinge (2017).
Bannan et al., "Characteristics of Adult Patients with Atrial Septal Defects Presenting with Paradoxical Embolism.," Catheterization and Cardiovascular Interventions, 74:1066-1069 (2009).
Baumgartner et al., "ESC Guidelines for the management of grown-up congenital heart disease (new version 2010)—The Task Force on the Management of Grown-up Congenital Heart Disease of the European Society of Cardiology (ESC)," Eur Heart J., 31:2915-2957 (2010).
Beemath et al., "Pulmonary Embolism as a Cause of Death in Adults Who Died With Heart Failure," Am J Cardiol., 98:1073-1075 (2006).
Benza et al., "Monitoring Pulmonary Arterial Hypertension Using an Implantable Hemodynamic Sensor," Chest, 156(6):1176-1186 (2019).
Boehm, et al., "Balloon Atrial Septostomy: History and Technique," Images Paeditr. Cardiol., 8(1):8-14 (2006).
Borlaug, et al., Latent Pulmonary Vascular Disease May Alter The Response to Therapeutic Atrial Shunt Device in Heart Failure, Circulation (Mar. 2022).
Braunwald, Heart Disease, Chapter 6, pp. 186.
Bridges, et al., "The Society of Thoracic Surgeons Practice Guideline Series: Transmyocardial Laser Revascularization," Ann Thorac Surg., 77:1494-1502 (2004).
Bristow, et al., "Improvement in cardiac myocite function by biological effects of medical therapy: a new concept in the treatment of heart failure," European Heart Journal, 16 (Suppl.F): 20-31 (1995).
Bruch et al., "Fenestrated Occluders for Treatment of ASD in Elderly Patients with Pulmonary Hypertension and/or Right Heart Failure," J Interven Cardiol., 21(1):44-49 (2008).
Burkhoff et al., "Assessment of systolic and diastolic ventricular properties via pressure-volume analysis: a guide for clinical, translational, and basic researchers," Am J Physiol Heart Circ Physiol., 289:H501-H512 (2005).
Butler et al. "Recognizing Worsening Chronic Heart Failure as an Entity and an End Point in Clinical Trials," JAMA., 312(8):789-790 (2014).
Case, et al., "Relief of High Left-Atrial Pressure in Left-Ventricular Failure," Lancet, (pp. 841-842), Oct. 17, 1964.
Chakko et al., "Clinical, radiographic, and hemodynamic correlations in chronic congestive heart failure: conflicting results may lead to inappropriate care," Am J Medicine, 90:353-359 (1991) (Abstract Only).
Chang et al., "State-of-the-art and recent developments in micro/nanoscale pressure sensors for smart wearable devices and health monitoring systems," Nanotechnology and Precision Engineering, 3:43-52 (2020).
Chen et al., "Continuous wireless pressure monitoring and mapping with ultra-small passive sensors for health monitoring and critical care," Nature Communications, 5(1):1-10 (2014).
Chen et al., "National and Regional Trends in Heart Failure Hospitalization and Mortality Rates for Medicare Beneficiaries, 1998-2008," JAMA, 306(15):1669-1678 (2011).
Chiche et al., "Prevalence of patent foramen ovale and stroke in pulmonary embolism patients," Eur Heart J., 34:P1142 (2013) (Abstract Only).
Chin et al., "The right ventricle in pulmonary hypertension," Coron Artery Dis., 16(1):13-18 (2005) (Abstract Only).
Chun et al., "Lifetime Analysis of Hospitalizations and Survival of Patients Newly Admitted With Heart Failure," Circ Heart Fail., 5:414-421 (2012).
Ciarka et al., "Atrial Septostomy Decreases Sympathetic Overactivity in Pulmonary Arterial Hypertension," Chest, 131(6):P1831-1837 (2007) (Abstract Only).

(56) References Cited

OTHER PUBLICATIONS

Cleland et al., "The EuroHeart Failure survey programme—a survey on the quality of care among patients with heart failure in Europe—Part 1: patient characteristics and diagnosis," Eur Heart J., 24:442-463 (2003).
Clowes et al., "Mechanisms of Arterial Graft Healing—Rapid Transmural Capillary Ingrowth Provides a Source of Intimal Endothelium and Smooth Muscle in Porous PTFE Prostheses," Am J Pathol., 123:220-230 (1986).
Clowes, et al., Mechanisms of Arterial Graft Healing—Rapid Transmural Capillary Ingrowth Provides a Source of Intimal Endothelium and Smooth Muscle in Porous PTFE Prostheses, Am. J. Pathol., 123(2):220-230 (May 1986).
Coats, et al., "Controlled Trial of Physical Training in Chronic Heart Failure: Exercise Performance, Hemodynamics, Ventilation, and Autonomic Function," Circulation, 85: 2119-2131 (1992).
Davies et al., "Abnormal left heart function after operation for atrial septal defect," British Heart Journal, 32:747-753 (1970).
Davies, et al., "Reduced Contraction and Altered Frequency Response of Isolated Ventricular Myocytes From Patients With Heart Failure, Circulation," 92: 2540-2549 (1995).
Del Trigo et al., "Unidirectional Left-To-Right Interatrial Shunting for Treatment of Patients with Heart Failure with Reduced Ejection Fraction: a Safety and Proof-of-Principle Cohort Study," Lancet, 387:1290-1297 (2016).
Della Lucia et al., "Design, fabrication and characterization of SAW pressure sensors for offshore oil and gas exploration," Sensors and Actuators A: Physical, 222:322-328 (2015).
Drazner et al., "Prognostic Importance of Elevated Jugular Venous Pressure and a Third Heart Sound in Patients with Heart Failure," N Engl J Med., 345(8):574-81 (2001).
Drazner et al., "Relationship between Right and Left-Sided Filling Pressures in 1000 Patients with Advanced Heart Failure," Heart Lung Transplant, 18:1126-1132 (1999).
Drexel, et al., "The Effects of Cold Work and Heat Treatment on the Properties of Nitinol Wire, Proceedings of the International Conference on Shape Memory and Superelastic Technologies, SMST 2006," Pacific Grove, California, USA (pp. 447-454) May 7-11, 2006.
Eigler et al., "Cardiac Unloading with an Implantable Interatrial Shunt in Heart Failure: Serial Observations in an Ovine Model of Ischemic Cardiomyopathy," Structural Heart, 1:40-48 (2017).
Eigler, et al., Implantation and Recovery of Temporary Metallic Stents in Canine Coronary Arteries, JACC, 22(4):1207-1213 (1993).
Ennezat, et al., An unusual case of low-flow, low gradient severe aortic stenosis: Left-to-right shunt due to atrial septal defect, Cardiology, 113(2):146-148, (2009).
Eshaghian et al., "Relation of Loop Diuretic Dose to Mortality in Advanced Heart Failure," Am J Cardiol., 97:1759-1764 (2006).
Ewert, et al., Acute Left Heart Failure After Interventional Occlusion of An Artial Septal Defect, Z Kardiol, 90(5): 362-366 (May 2001).
Ewert, et al., Masked Left Ventricular Restriction in Elderly Patients With Atrial Septal Defects: A Contraindication for Closure?, Catheterization and Cardiovascular Intervention, 52:177-180 (2001).
Extended European Search Report dated Jan. 8, 2015 in EP Patent Appl No. 10772089.8. (0530).
Extended European Search Report dated Mar. 29, 2019 in EP Patent Appl. Serial No. EP16789391 (1830).
Extended European Search Report dated Sep. 19, 2016 in EP Patent Appl. No. 16170281.6 (0731).
Feldman et al., "Transcatheter Interatrial Shunt Device for the Treatment of Heart Failure with Preserved Ejection Fraction (Reduce LAP-HF I [Reduce Elevated Left Atrial Pressure in Patients With Heart Failure]), A Phase 2, Randomized, Sham-Controlled Trial," Circulation, 137:364-375 (2018).
Ferrari et al., "Impact of pulmonary arterial hypertension (PAH) on the lives of patients and carers: results from an international survey," Eur Respir J., 42:26312 (2013) (Abstract Only).

Flachskampf, et al., Influence of Orifice Geometry and Flow Rate on Effective Valve Area: An In Vitro Study, Journal of the American College of Cardiology, 15(5):1173-1180 (Apr. 1990).
Fonarow et al., "Characteristics, Treatments, and Outcomes of Patients With Preserved Systolic Function Hospitalized for Heart Failure," J Am Coll Cardiol., 50(8):768-777 (2007).
Fonarow et al., "Risk Stratification for In-Hospital Mortality in Acutely Decompensated Heart Failure: Classification and Regression Tree Analysis," JAMA, 293(5):572-580 (2005).
Fonarow, G., "The Treatment Targets in Acute Decompensated Heart Failure," Rev Cardiovasc Med., 2:(2):S7-S12 (2001).
Galie et al., "2015 ESC/ERS Guidelines for the diagnosis and treatment of pulmonary hypertension—The Joint Task Force for the Diagnosis and Treatment of Pulmonary Hypertension of the European Society of Cardiology (ESC) and the European Respiratory Society (ERS)," European Heart Journal, 37:67-119 (2016).
Galie et al., "Pulmonary arterial hypertension: from the kingdom of the near-dead to multiple clinical trial meta-analyses," Eur Heart J., 31:2080-2086 (2010).
Galipeau et al., "Surface acoustic wave microsensors and applications," Smart Materials and Structures, 6(6):658-667 (1997) (Abstract Only).
Geiran, et al., Changes in cardiac dynamics by opening an interventricular shunt in dogs, J. Surg. Res. 48(1):6-12 (1990).
Gelernter-Yaniv, et al., Transcatheter ClosureoOf Left-To-Right Interatrial Shunts to Resolve Hypoxemia, Congenit. Heart Dis. 31 (1): 47-53 (Jan. 2008).
Geva et al., "Atrial septal defects," Lancet, 383:1921-32 (2014).
Gewillig, et al., Creation with a stent of an unrestrictive lasting atrial communication, Cardio. Young 12(4): 404-407 (2002).
Gheorghiade et al., "Effects of Tolvaptan, a Vasopressin Antagonist, in Patients Hospitalized With Worsening Heart Failure A Randomized Controlled Trial," JAMA., 291:1963-1971 (2004).
Gheorghiade M., et al., "Acute Heart Failure Syndromes, Current State and Framework for Future Research," Circulation, 2005, vol. 112, pp. 3958-3968.
Go et al. "Heart Disease and Stroke Statistics—2014 Update—A Report From the American Heart Association," Circulation, 128:1-267 (2014).
Greitz, et al., Pulsatile Brain Movement and Associated Hydrodynamics Studied by Magnetic Resonance Phase Imaging, Diagnostic Neuroradiology, 34(5): 370-380 (1992).
Guillevin et al., "Understanding the impact of pulmonary arterial hypertension on patients' and carers' lives," Eur Respir Rev., 22:535-542 (2013).
Guyton et al., "Effect of Elevated Left Atrial Pressure and Decreased Plasma Protein Concentration on the Development of Pulmonary Edema," Circulation Research, 7:643-657 (1959).
Hasenfub, et al., A Transcatheter Intracardiac Shunt Device for Heart Failure with Preserved Ejection Fraction (Reduce LAP-HF): A Multicentre, Open-Label, Single-Arm, Phase 1 Trial, www.thelancet.com, 387:1298-1304 (2016).
Hoeper et al., "Definitions and Diagnosis of Pulmonary Hypertension," J Am Coll Cardiol., 62(5):D42-D50 (2013).
Hogg et al., "Heart Failure With Preserved Left Ventricular Systolic Function. Epidemiology, Clinical Characteristics, and Prognosis," J Am Coll Cardiol., 43(3):317-327 (2004).
Howell et al., "Congestive heart failure and outpatient risk of venous thromboembolism: A retrospective, case-control study," Journal of Clinical Epidemiology, 54:810-816 (2001).
Huang et al., "Remodeling of the chronic severely failing ischemic sheep heart after coronary microembolization: functional, energetic, structural, and cellular responses," Am J Physiol Heart Circ Physiol., 286:H2141-H2150 (2004).
Humbert et al., "Pulmonary Arterial Hypertension in France—Results from a National Registry," Am J Respir Crit Care Med., 173:1023-1030 (2006).
International Search Report & Written Opinion dated Nov. 7, 2016 in Int'l PCT Patent Appl. Serial No. PCT/IB2016/052561 (1810).
International Search Report & Written Opinion dated May 29, 2018 in Int'l PCT Patent Appl. Serial No. PCT/IB2018/051385 (1310).
International Search Report & Written Opinion dated Feb. 3, 2023 in Int'l PCT Patent Appl. Serial No. PCT/IB2022/060621 (2210).

(56) References Cited

OTHER PUBLICATIONS

International Search Report & Written Opinion dated Feb. 6, 2013 in Int'l PCT Patent Appl. No. PCT/IB2012/001859, 12 pages (0810).
International Search Report & Written Opinion dated Feb. 7, 2020 in Int'l PCT Patent Appl. Serial No. PCT/IB2019/060257 (1410).
International Search Report & Written Opinion dated Feb. 9, 2022 in Int'l PCT Patent Appl. Serial No. PCT/IB2021/060473 (2010).
International Search Report & Written Opinion dated Mar. 29, 2023 in Int'l PCT Patent Appl. Serial No. PCT/IB2023/050743 (2410).
International Search Report & Written Opinion dated May 13, 2019 in Int'l PCT Patent Appl. No. PCT/IB2019/050452 (1610).
International Search Report & Written Opinion dated May 17, 2022 in Int'l PCT Patent Appl. Serial No. PCT/IB2022/051177 (2310).
International Search Report & Written Opinion dated May 29, 2018 in Int'l PCT Patent Appl. Serial No. PCTIB2018/051355 (1310).
International Search Report & Written Opinion dated Jul. 14, 2020 in Int'l PCT Patent Appl. Serial No. PCT/IB2020/053832 (1210).
International Search Report & Written Opinion dated Jul. 20, 2020 in Int'l PCT Patent Appl. Serial No. PCT/IB2020/054699 (1710).
International Search Report & Written Opinion dated Jul. 23, 2021 in Int'l PCT Patent Appl. Serial No. PCT/IB2021/053594 (1910).
International Search Report & Written Opinion dated Aug. 12, 2020 in Int'l PCT Patent Appl. Serial No. PCT/IB2020/053118 (1010).
International Search Report & Written Opinion dated Aug. 28, 2012 in Int'l PCT Patent Appl. No. PCT/IL2011/000958 (0710).
International Search Report & Written Opinion dated Sep. 21, 2020 in Int'l PCT Patent Appl. Serial No. PCT/IB2020/054306 (1510).
International Search Report & Written Opinion dated Oct. 11, 2017 in Int'l PCT Patent Appl. Serial No. PCT/IB2017/053188 (1110).
International Search Report & Written Opinion dated Oct. 26, 2007 in Int'l PCT Patent Appl. Serial No. PCT/IB07/50234 (0610).
International Search Report dated Apr. 7, 2008 in Int'l PCT Patent Appl. Serial No. PCT/IL05/00131 (0410).
International Search Report dated Aug. 25, 2010 in Intl PCT Patent Appl. Serial No. PCT/IL2010/000354 (0510).
ISR & Written Opinion dated Feb. 16, 2015 in Int'l PCT Patent Appl. Serial No. PCT/IB2014/001771 (0910).
Jessup et al. "2009Focused Update: ACC/AHA Guidelines for the Diagnosis and Management of Heart Failure in Adults: A Report of the American College of Cardiology Foundation/American Heart Association Task Force on Practice Guidelines: Developed in Collaboration With the International Society for Heart and Lung Transplantation," J. Am. Coll. Cardiol., 53:1343-1382 (2009).
Jiang, G., "Design challenges of implantable pressure monitoring system," Frontiers in Neuroscience, 4(29):1-4 (2010).
Kane et al., "Integration of clinical and hemodynamic parameters in the prediction of long-term survival in patients with pulmonary arterial hypertension," Chest, 139(6):1285-1293 (2011) (Abstract Only).
Kaye et al., "Effects of an Interatrial Shunt on Rest and Exercise Hemodynamics: Results of a Computer Simulation in Heart Failure," Journal of Cardiac Failure, 20(3): 212-221 (2014).
Kaye et al., "One-Year Outcomes After Transcatheter Insertion of an Interatrial Shunt Device for the Management of Heart Failure With Preserved Ejection Fraction," Circulation: Heart Failure, 9(12):e003662 (2016).
Kaye, et al., One-Year Outcomes After Transcatheter Insertion of an Interatrial Shunt Device for the Management of Heart Failure with Preserved Ejection Fraction, Circulation: Heart Failure, 9(12):e003662 (Dec. 2016).
Keogh et al., "Interventional and Surgical Modalities of Treatment in Pulmonary Hypertension," J Am Coll Cardiol., 54:S67-77 (2009).
Khositseth et al., Transcatheter Amplatzer Device Closure of Atrial Septal Defect and Patent Foramen Ovale in Patients With Presumed Paradoxical Embolism, Mayo Clinic Proc., 79:35-41 (2004).
Kramer, et al., Controlled Trial of Captopril in Chronic Heart Failure: A Rest and Exercise Hemodynamic Study, Circulation, 67(4): 807-816, 1983.

Kretschmar et al., "Shunt Reduction With a Fenestrated Amplatzer Device," Catheterization and Cardiovascular Interventions, 76:564-571 (2010).
Kropelnicki et al., "CMOS-compatible ruggedized high-temperature Lamb wave pressure sensor," J. Micromech. Microeng., 23:085018 pp. 1-9 (2013).
Krumholz et al., "Patterns of Hospital Performance in Acute Myocardial Infarction and Heart Failure 30-Day Mortality and Readmission," Circ Cardiovasc Qual Outcomes, 2:407-413 (2009).
Kulkarni et al., "Lutembacher's syndrome," J Cardiovasc Did Res., 3(2):179-181 (2012).
Kurzyna et al., "Atrial Septostomy in Treatment of End-Stage Right Heart Failure in Patients With Pulmonary Hypertension," Chest, 131:977-983 (2007).
Lai et al., Bidirectional Shunt Through a Residual Atrial Septal Defect After Percutaneous Transvenous Mitral Commissurotomy, Cadiology, 83(3): 205-207 (1993).
Lammers et al., "Efficacy and Long-Term Patency of Fenerstrated Amplatzer Devices in Children," Catheter Cardiovasc Interv., 70:578-584 (2007).
Lemmer, et al., Surgical Implications of Atrial Septal Defect Complicating Aortic Balloon Valvuloplasty, Ann. thorac. Surg, 48(2):295-297 (Aug. 1989).
Lindenfeld et al. "Executive Summary: HFSA 2010 Comprehensive Heart Failure Practice Guideline," J. Cardiac Failure, 16(6):475-539 (2010).
Luo, Yi, *Selective and Regulated RF Heating of Stent Toward Endohyperthermia Treatment of In-Stent Restenosis*, A Thesis Submitted in Partial Fulfillment of The Requirements For The Degree of Master of Applied Science in The Faculty of Graduate and Postdoctoral Studies (Electrical and Computer Engineering), The University of British Columbia, Vancouver, Dec. 2014.
MacDonald et al., "Emboli Enter Penetrating Arteries of Monkey Brain in Relation to Their Size," Stroke, 26:1247-1251 (1995).
Maluli et al., "Atrial Septostomy: A Contemporary Review," Clin. Cardiol., 38(6):395-400 (2015).
Maurer et al., "Rationale and Design of the Left Atrial Pressure Monitoring to Optimize Heart Failure Therapy Study (LAPTOP-HF)," Journal of Cardiac Failure., 21(6): 479-488 (2015).
McClean et al., "Noninvasive Calibration of Cardiac Pressure Transducers in Patients With Heart Failure: An Aid to Implantable Hemodynamic Monitoring and Therapeutic Guidance," J Cardiac Failure, 12(7):568-576 (2006).
McLaughlin et al., "Management of Pulmonary Arterial Hypertension," J Am Coll Cardiol., 65(18):1976-1997 (2015).
McLaughlin et al., "Survival in Primary Pulmonary Hypertension—The Impact of Epoprostenol Therapy.," Circulation, 106:1477-1482 (2002).
Merriam- Webster OnLine Dictionary, Definition of "chamber", printed Dec. 20, 2004.
Mu et al., "Dual mode acoustic wave sensor for precise pressure reading," Applied Physics Letters, 105:113507-1-113507-5 (2014).
Nagaraju et al., "A 400 µW Differential FBAR Sensor Interface IC with digital readout," IEEE., pp. 218-221 (2015).
Noordegraaf et al., "The role of the right ventricle in pulmonary arterial hypertension," Eur Respir Rev., 20(122):243-253 (2011).
O'Byrne et al., "The effect of atrial septostomy on the concentration of brain-type natriuretic peptide in patients with idiopathic pulmonary arterial hypertension," Cardiology in the Young, 17(5):557-559 (2007) (Abstract Only).
Oktay et al., "The Emerging Epidemic of Heart Failure with Preserved Ejection Fraction," Curr Heart Fail Rep., 10(4):1-17 (2013).
Owan et al., "Trends in Prevalence and Outcome of Heart Failure with Preserved Ejection Fraction," N Engl J Med., 355:251-259 (2006).
Paitazoglou et al., "Title: The AFR-Prelieve Trial: A prospective, non-randomized, pilot study to assess the Atrial Flow Regulator (AFR) in Heart Failure Patients with either preserved or reduced ejection fraction," EuroIntervention, 28:2539-50 (2019).
Park Blade Septostomy Catheter Instructions for Use, Cook Medical, 28 pages, Oct. 2015.

(56) References Cited

OTHER PUBLICATIONS

Park, et al., Blade Atrial Septostomy: Collaborative Study, Circulation, 66(2):258-266 (1982).
Partial Supplemental European Search Report dated Dec. 11, 2018 in EP Patent Appl. Serial No. 16789391.6 (1830).
Peters et al., "Self-fabricated fenestrated Amplatzer occluders for transcatheter closure of atrial septal defect in patients with left ventricular restriction: midterm results," Clin Res Cardiol., 95:88-92 (2006).
Pfeiffer, In vivo fluid dynamics of the Ventura interatrial shunt device in patients with heart failure, ESC Heart Failure, DOI: 10.1002/ehf2.14859 (May 22, 2024).
Ponikowski et al., "2016 ESC Guidelines for the diagnosis and treatment of acute and chronic heart failure. The Task Force for the diagnosis and treatment of acute and chronic heart failure of the European Society of Cardiology (ESC)," Eur Heart J., doi:10.1093/eurheartj/ehw128 (2016).
Potkay, J. A., "Long term, implantable blood pressure monitoring systems," Biomed Microdevices, 10:379-392 (2008).
Pretorious et al., "An Implantable Left Atrial Pressure Sensor Lead Designed for Percutaneous Extraction Using Standard Techniques," Pace, 00:1-8 (2013).
Rajeshkumar et al., "Atrial septostomy with a predefined diameter using a novel occlutech atrial flow regulator improves symptoms and cardiac index in patients with severe pulmonary arterial hypertension," Catheter Cardiovasc Interv., 1-9 (2017).
Rich et al., "Atrial Septostomy as Palliative Therapy for Refractory Primary Pulmonary Hypertension," Am J Cardiol., 51:1560-1561 (1983).
Ritzema et al., "Direct Left Atrial Pressure Monitoring in Ambulatory Heart Failure Patients—Initial Experience With a New Permanent Implantable Device," Circulation, 116:2952-2959 (2007).
Ritzema et al., "Physician-Directed Patient Self-Management of Left Atrial Pressure in Advanced Chronic Heart Failure," Circulation, 121:1086-1095 (2010).
Roberts et al., "Integrated microscopy techniques for comprehensive pathology evaluation of an implantable left atrial pressure sensor," J Histotechnology, 36(1):17-24 (2013).
Rodes-Cabau, et al., Interatrial shunt therapy in advanced heart failure: Outcomes from the open-label cohort of the Relieve-HF trial, Eur. J. Heart. Fail., 26(4):1078-1089 (Apr. 2024).
Rodes-Cabau et al., "Interatrial Shunting for Heart Failure Early and Late Results From the First-in-Human Experience With the V-Wave System," J Am Coll Cardiol Intv., 11:2300-2310.doi:10.1016/j.cin. 2018.07.001 (2018).
Rosenquist et al., Atrial Septal Thickness and Area in Normal Heart Specimens and in Those With Ostium Secundum Atrial Septal Defects, J. Clin. Ultrasound, 7:345-348 (1979).
Ross et al., "Interatrial Communication and Left Atrial Hypertension—A Cause of Continuous Murmur," Circulation, 28:853-860 (1963).
Rossignol, et al., Left-to-Right Atrial Shunting: New Hope for Heart Failure, www.thelancet.com, 387:1253-1255 (2016).
Roven, Effect of Compromising Right Ventricular Function in Left Ventricular Failure by Means of Interatrial and Other Shunts 24:209-219 (Aug. 1969).
Salehian, et al., Improvements in Cardiac Form and Function After Transcatheter Closure of Secundum Atrial Septal Defects, Journal of the American College of Cardiology, 45(4):499-504 (2005).
Sandoval et al., "Effect of atrial septostomy on the survival of patients with severe pulmonary arterial hypertension," Eur Respir J., 38:1343-1348 (2011).
Sandoval et al., "Graded Balloon Dilation Atrial Septostomy in Severe Primary Pulmonary Hypertension—A Therapeutic Alternative for Patients Nonresponsive to Vasodilator Treatment," JACC, 32(2):297-304 (1998).
Schiff et al., "Decompensated heart failure: symptoms, patterns of onset, and contributing factors," Am J. Med., 114(8):625-630 (2003) (Abstract Only).

Schmitto, et al., Chronic Heart Failure Induced by Multiple Sequential Coronary Microembolization in sheep, The International Journal of Artificial Organs, 31(4):348-353 (2008).
Schneider et al., "Fate of a Modified Fenestration of Atrial Septal Occluder Device after Transcatheter Closure of Atrial Septal Defects in Elderly Patients," J Interven Cardiol., 24:485-490 (2011).
Scholl et al., "Surface Acoustic Wave Devices for Sensor Applications," Phys Status Solidi Appl Res., 185(1):47-58 (2001) (Abstract Only).
Schubert, et al., Left ventricular Conditioning in the Elderly Patient to Prevent Congestive Heart Failure After Transcatheter Closure of the Atrial Septal Defect, Catheterization and Cardiovascular Interventions, 64(3): 333-337 (2005).
Setoguchi et al., "Repeated hospitalizations predict mortality in the community population with heart failure," Am Heart J., 154:260-266 (2007).
Shah, et al., Atrial Shunt Device For Heart Failure With Preserved And Mildly Reduced Ejection Fraction (Reduce LAP-HF II): A Randomised, Multicentre, Blinded, Sham-Controlled Trial, The Lancet, 399(10330):1130-1140 (Mar. 2022).
Shah et al., "Heart Failure With Preserved, Borderline, and Reduced Ejection Fraction—5-Year Outcomes," J Am Coll Cardiol., https://doi.org/10.1016/j.jacc.2017.08.074 (2017).
Shah et al., "One-Year Safety and Clinical Outcomes of a Transcatheter Interatrial Shunt Device for the Treatment of Heart Failure With Preserved Ejection Fraction in the Reduce Elevated Left Atrial Pressure in Patients With Heart Failure (Reduce LAP-HF I) Trial—A Randomized Clinical Trial," JAMA Cardiol. doi:10.1001/jamacardio. 2018.2936 (2018).
Sitbon et al., "Selexipag for the Treatment of Pulmonary Arterial Hypertension.," N Engl J Med., 373(26):2522-2533 (2015).
Sitbon et al., "Epoprostenol and pulmonary arterial hypertension: 20 years of clinical experience," Eur Respir Rev., 26:160055:1-14 (2017).
Steimle et al., "Sustained Hemodynamic Efficacy of Therapy Tailored to Reduce Filling Pressures in Survivors With Advanced Heart Failure," Circulation, 96:1165-1172 (1997).
Stevenson et al., "The Limited Reliability of Physical Signs for Estimating Hemodynamics in Chronic Heart Failure," JAMA, 261(6):884-888 (1989) (Abstract Only).
Stone, Gregg, A Double-blind, Randomized Placebo-Procedure-Controlled Trial of an Interatrial Shunt in Patients with HFrEF and HFpEF: Principal Results from the Relieve-HF Trial, American College of Cardiology (ACC) (Apr. 6, 2024).
Stormer, et al., Comparative Study of in Vitro Flow Characteristics Between a Human Aortic Valve and a Designed Aortic Valve and Six Corresponding Types of Prosthetic Heart Valves, European Surgical Research 8(2):117-131 (1976).
Stumper, et al., Modified Technique of Stent Fenestration of the Atrial Septum, Heart, 89:1227-1230, (2003).
Su et al., "A film bulk acoustic resonator pressure sensor based on lateral field excitation," International Journal of Distributed Sensor Networks, 14(11):1-8 (2018).
Supplementary European Search Report dated Nov. 13, 2009 in EP Patent Appl. Serial No. 05703174.2 (0430).
Thenappan et al., "Evolving Epidemiology of Pulmonary Arterial Hypertension," Am J Resp Critical Care Med., 186:707-709 (2012).
Tomai et al., "Acute Left Ventricular Failure After Transcatheter Closure of a Secundum Atrial Septal Defect in a Patient With Coronary Artery Disease: A Critical Reappraisal," Catheterization and Cardiovascular Interventions, 55:97-99 (2002).
Torbicki et al., "Atrial Septostomy," The Right Heart, 305-316 (2014).
Trainor, et al., Comparative Pathology of an Implantable Left Atrial Pressure Sensor, ASAIO Journal, Clinical Cardiovascular/Cardiopulmonary Bypass, 59(5):486-492 (2013).
Troost et al., "A Modified Technique of Stent Fenestration of the Interatrial Septum Improves Patients With Pulmonary Hypertension," Catheterization and Cardiovascular Interventions, 73:173179 (2009).
Troughton et al., "Direct Left Atrial Pressure Monitoring in Severe Heart Failure: Long-Term Sensor Performance," J. of Cardiovasc. Trans. Res., 4:3-13 (2011).

(56) References Cited

OTHER PUBLICATIONS

Vank-Noordegraaf et al., "Right Heart Adaptation to Pulmonary Arterial Hypertension—Physiology and Pathobiology," J Am Coll Cardiol., 62(25):D22-33 (2013).

Verel et al., "Comparison of left atrial pressure and wedge pulmonary capillary pressure—Pressure gradients between left atrium and left ventricle," British Heart J., 32:99-102 (1970).

Viaene et al., "Pulmonary oedema after percutaneous ASD-closure," Acta Cardiol., 65(2):257-260 (2010).

Wang et al., "A Low Temperature Drifting Acoustic Wave Pressure Sensor with an Integrated Vacuum Cavity for Absolute Pressure Sensing," Sensors, 20(1788):1-13 (2020).

Warnes et al., "ACC/AHA 2008 Guidelines for the Management of Adults With Congenital Heart Disease—A Report of the American College of Cardiology/American Heart Association Task Force on Practice Guidelines (Writing Committee to Develop Guidelines on the Management of Adults With Congenital Heart Disease)," JACC, 52(23):e143-e263 (2008).

Webb et al., "Atrial Septal Defects in the Adult Recent Progress and Overview," Circulation, 114:1645-1653 (2006).

Wiedemann, H.R., "Earliest description by Johann Friedrich Meckel, Senior (1750) of what is known today as Lutembacher syndrome (1916)," Am J Med Genet., 53(1):59-64 (1994) (Abstract Only).

Written Opinion of the International Searching Authority dated Apr. 7, 2008 in Int'l PCT Patent Appl. Serial No. PCT/IL05/00131 (0410).

Yantchev et al., "Thin Film Lamb Wave Resonators in Frequency Control and Sensing Applications: A Review," Journal of Micromechanics and Microengineering, 23(4):043001 (2013).

Zhang et al., "Acute left ventricular failure after transcatheter closure of a secundum atrial septal defect in a patient with hypertrophic cardiomyopathy," Chin Med J., 124(4):618-621 (2011).

Zhang et al., "Film bulk acoustic resonator-based high-performance pressure sensor integrated with temperature control system," J Micromech Microeng., 27(4):1-10 (2017).

Zhou, et al., Unidirectional Valve Patch for Repair of Cardiac Septal Defects with Pulmonary Hypertension, Annals of Thoracic Surgeons, 60:1245-1249, (1995).

International Search Report & Written Opinion dated Jan. 15, 2025 in Int'l PCT Patent Appl. Serial No. PCT/IB2024/060159.

Stone, Interatrial Shunt Treatment for Heart Failure: The Randomized Relieve-HF Trial, Circulation. 2024; 150:1931-1943. DOI: 10.1161/CIRCULATIONAHA.124.070870 (Dec. 10, 2024).

\* cited by examiner

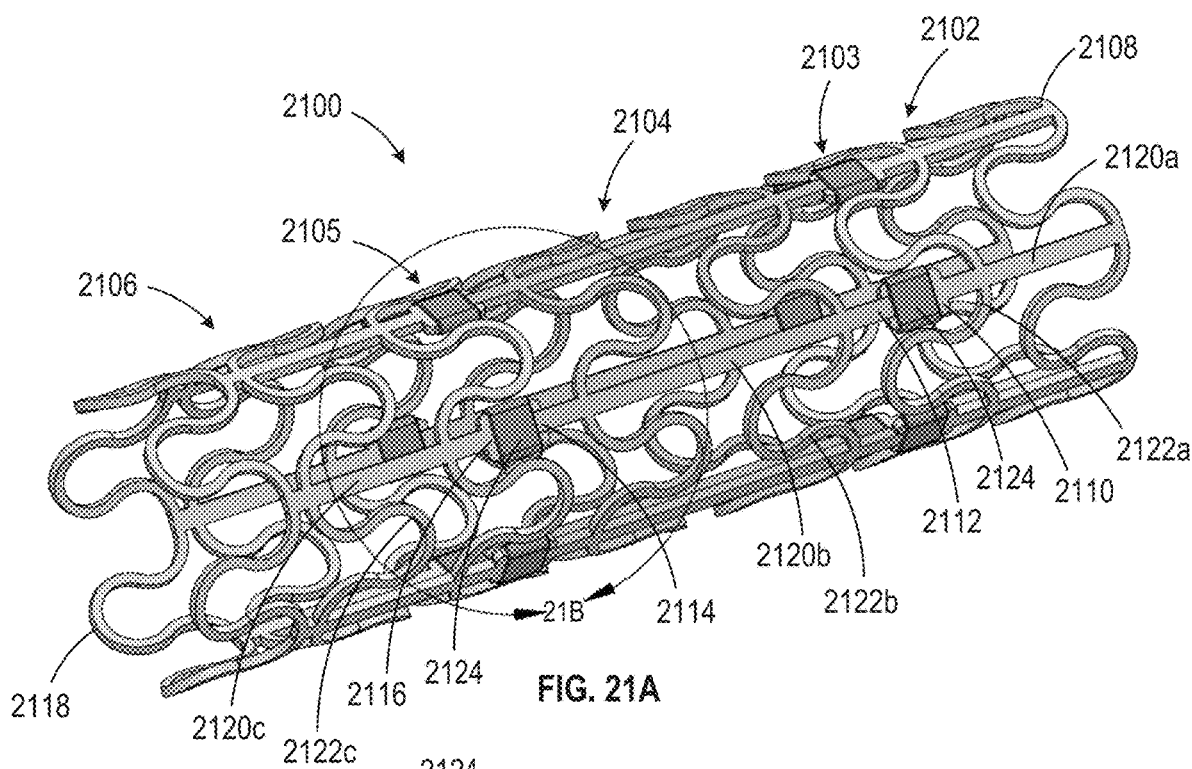
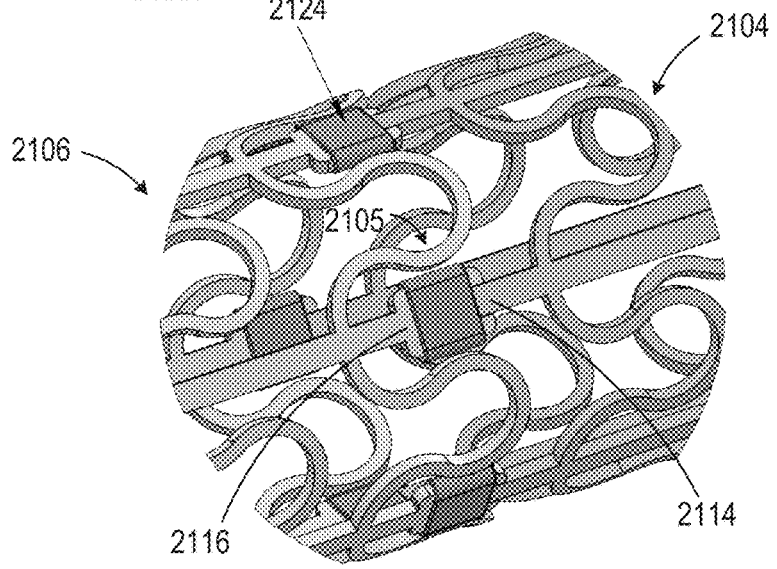
FIG. 21A
FIG. 21B

HYBRID DEVICES WITH DIMENSIONS THAT CAN BE ADJUSTED IN VIVO AND METHODS OF MANUFACTURING THEREOF

CROSS-REFERENCE TO RELATED APPLICATIONS

This application claims priority to U.S. Patent Provisional Application No. 63/591,428, filed Oct. 18, 2023, the entire contents of which are incorporated herein by reference.

TECHNICAL FIELD

This technology generally relates to devices for use in the human body, such as percutaneously implanted devices and methods for adjusting the flow of fluid, such as blood, within the human body.

BACKGROUND

For a number of medical conditions, there is benefit in adjusting the flow of fluid within the human body, for example, through a passage between two body cavities. Such a passage is typically used in catheterization procedures where the catheter is delivered through a patient's vasculature. In some catheterization procedures, there is a benefit in moving from one cavity to another cavity by creating a passage. For example, such a passage may be formed between the right side of the heart and the left side of the heart, e.g., between the right atrium toward the left atrium, where clinical procedures are done on the left side of the heart using an entry from the right side of the heart. Such clinical procedures include, e.g., arrhythmia ablation procedures in the left atrium and mitral valve repair activities.

In addition, a passage may be created and maintained in a heart wall between two heart chambers for housing a shunt for redistributing blood from one heart chamber to another to address pathologies such as heart failure (HF), myocardial infarction (MI), and pulmonary arterial hypertension (PAH). HF is the physiological state in which cardiac output is insufficient to meet the needs of the body or to do so only at a higher filling pressure. There are many underlying causes of HF, including MI, coronary artery disease, valvular disease, hypertension (such as PAH), and myocarditis. Chronic heart failure is associated with neurohormonal activation and alterations in autonomic control. Although these compensatory neurohormonal mechanisms provide valuable support for the heart under normal physiological circumstances, they also play a fundamental role in the development and subsequent progression of HF.

HF is generally classified as either systolic heart failure ("SHF") or diastolic heart failure ("DHF"). In SHF, the pumping action of the heart is reduced or weakened. A common clinical measurement is the ejection fraction, which is a function of the blood ejected out of the left ventricle (stroke volume) divided by the maximum volume in the left ventricle at the end of diastole or relaxation phase. A normal ejection fraction is greater than 50%. Systolic heart failure generally causes a decreased ejection fraction of less than 40%. Such patients have heart failure with reduced ejection fraction ("HFrEF"). A patient with HFrEF may usually have a larger left ventricle because of a phenomenon called "cardiac remodeling" that occurs secondarily to the higher ventricular pressures.

In DHF, the heart generally contracts well, with a normal ejection fraction, but is stiffer, or less compliant, than a healthy heart would be when relaxing and filling with blood. Such patients are said to have heart failure with preserved ejection fraction ("HFpEF"). This stiffness may impede blood from filling the heart and produce backup into the lungs, which may result in pulmonary venous hypertension and lung edema. HFpEF is more common in patients older than 75 years, especially in women with high blood pressure.

Both variants of HF have been treated using pharmacological approaches, which typically involve the use of vasodilators for reducing the workload of the heart by reducing systemic vascular resistance, as well as diuretics, which inhibit fluid accumulation and edema formation, and reduce cardiac filling pressure. No pharmacological therapies have been shown to improve morbidity or mortality in HFpEF whereas several classes of drugs have made an important impact on the management of patients with HFrEF, including renin-angiotensin antagonists, neprilysin inhibitors, beta blockers, mineralocorticoid antagonists and sodium-glucose co-transporter-2 (SGLT2) inhibitors. Nonetheless, in general, HF remains a progressive disease and most patients have deteriorating cardiac function and symptoms over time. In the U.S., there are over 1 million hospitalizations annually for acutely worsening HF and mortality is higher than for most forms of cancer.

In more severe cases of HFrEF, mechanical circulatory support (MCS) devices such as mechanical pumps are used to reduce the load on the heart by performing all or part of the pumping function normally done by the heart. Chronic left ventricular assist devices ("LVAD"), the total artificial heart, and cardiac transplantation are used as measures of last resort. However, such assist devices typically are intended to improve the pumping capacity of the heart, to increase cardiac output to levels compatible with normal life, and to sustain the patient until a donor heart for transplantation becomes available. This usage of MCS is also known as "bridge to transplant" therapy". As the supply of donor hearts for transplantation is insufficient for the demand, more often MCS is the only therapeutic option— also known as "destination therapy." Such mechanical devices enable propulsion of significant volumes of blood (liters/min) but are limited by a need for a power supply, relatively large pumps, and pose a risk of hemolysis, thrombus formation, and infection. Temporary assist devices, intra-aortic balloons, and pacing devices have also been used.

Various devices have been developed using stents to modify blood pressure and flow within a given vessel, or between chambers of the heart. For example, U.S. Pat. No. 6,120,534 to Ruiz is directed to an endoluminal stent for regulating the flow of fluids through a body vessel or organ, for example, for regulating blood flow through the pulmonary artery to treat congenital heart defects. The stent may include an expandable mesh having balloon-expandable lobed or conical portions joined by a shape-memory constricted region, which limits flow through the stent. The constricted region may be adjusted in vivo, and in addition may be heated to recover a maximum degree of constriction. Ruiz is silent on the treatment of HF or the reduction of left atrial pressure.

U.S. Patent Publication No. 2013/0178784 to McNamara describes an adjustable pressure relief shunt that may be expanded, e.g., via an inflation balloon. A tubular body of the shunt may be plastically deformed in vivo, such that the size of the shunt may be repeatedly adjusted by a variety of mechanisms, for example, elastically wound springs or a series of pawls and one-way mechanical ramps, responsive to measurements of the patient's physiological parameters. A key drawback to the approach described in that patent is the hysteresis effect, i.e., non-reversible changes in the underlying crystalline structure that occur when the shunt is permanently deformed. Importantly, such plastic deformation may lead to stress and fatigue-related fracture of the device.

U.S. Pat. No. 6,468,303 to Amplatz et al. describes a collapsible medical device and associated method for shunting selected organs and vessels. Amplatz describes that the device may be suitable to shunt a septal defect of a patient's heart, for example, by creating a shunt in the atrial septum of a neonate with hypoplastic left heart syndrome ("HLHS"). That patent also describes that increasing mixing of pulmonary and systemic venous blood improves oxygen saturation, and that the shunt may later be closed with an occluding device. Amplatz is silent on the treatment of HF or the reduction of left atrial pressure, as well as on means for regulating the rate of blood flow through the device.

Implantable interatrial shunt devices have been successfully used in patients with severe symptomatic heart failure. By diverting or shunting blood from the left atrium ("LA") to the right atrium ("RA"), the pressure in the left atrium is lowered or prevented from elevating as high as it would otherwise (left atrial decompression). Such an accomplishment would be expected to prevent, relieve, or limit the symptoms, signs, and syndromes associated of pulmonary congestion. These include severe shortness of breath, pulmonary edema, hypoxia, the need for acute hospitalization, mechanical ventilation, and death.

Shunt flow is generally governed by the pressure gradient between the atria and the fluid mechanical properties of the shunt device. The latter are typically affected by the shunt's geometry and material composition. For example, the general flow properties of similar shunt designs have been shown to be related to the mean interatrial pressure gradient and the effective orifice diameter.

Percutaneous implantation of interatrial shunts generally requires transseptal catheterization immediately preceding shunt device insertion. The transseptal catheterization system is generally placed from an entrance site in the femoral vein, across the interatrial septum in the region of fossa ovalis ("FO"), which is the central and thinnest region of the interatrial septum. The FO in adults is typically 15-20 mm in its major axis dimension and <3 mm in thickness, but in certain circumstances may be up to 10 mm thick. LA chamber access may be achieved using a host of different techniques familiar to those skilled in the art, including but not limited to: needle puncture, stylet puncture, screw needle puncture, and radiofrequency ablation. The passageway between the two atria is dilated to facilitate passage of a shunt device having a desired orifice size. Dilation generally is accomplished by advancing a tapered sheath/dilator catheter system or inflation of an angioplasty type balloon across the FO. This is the same general location where a congenital *secundum* atrial septal defect ("ASD") would be located.

U.S. Patent Publication No. 2005/0165344 to Dobak, III describes apparatus for treating heart failure that includes a tubular conduit having an emboli filter or valve, the device configured to be positioned in an opening in the atrial septum of the heart to allow flow from the left atrium into the right atrium. Dobak discloses that shunting of blood may reduce left atrial pressures, thereby preventing pulmonary edema and progressive left ventricular dysfunction, and reducing LVEDP. Dobak describes that the device may include deployable retention struts, such as metallic arms that exert a slight force on the atrial septum on both sides and pinch or clamp the device to the septum.

In addition, following implantation of a shunt device within a heart wall, tissue ingrowth including an endothelial layer or neointima layer typically forms on the device, thereby inhibiting thrombogenicity of the shunt device, and narrowing the size of the passage through the device.

SUMMARY

The present disclosure overcomes the drawbacks of previously-known systems and methods by providing devices with dimensions that not only may be increased, but also may be reduced in vivo, and methods of making and using the same. In particular, the present disclosure overcomes the limitations of previously known devices and methods by providing an implantable device with a composite structure exhibiting both superelastic and shape-memory properties at body temperature. Dimensions that may affect blood flow or other intended interactions between the implanted device and its biological host can be repeatedly altered in either direction by mechanical deformation of one crystalline phase of the shape-memory component in one direction and reversing the direction by temperature induction of a crystalline phase change of the shape-memory component material to its original dimension, greatly simplifying catheter related manipulations.

In accordance with one aspect, a hybrid shunt comprising shape-memory material for placement at an atrial septum of a patient's heart is provided. The hybrid shunt may comprise a neck region configured to be malleable at body temperature, a first end region configured to be superelastic at body temperature, a distal end of the first end region configured to be permanently fixed to a proximal end of the neck region at a first connection, a second end region configured to be superelastic at body temperature, a proximal end of the second end region configured to be permanently fixed to with a distal end of the neck region at a second connection, and a passageway extending through the first end region, the neck region, and the second end region for blood to flow across the atrial septum. The flow area of the passageway through the neck region may be configured to be adjustable in vivo. Preferably, the first and second end regions are not formed integrally with the neck region.

The proximal and distal ends of the neck region may comprise a shape configured to interlock with a complementary shape of the distal end of the first end region and the proximal end of the second end region, respectively. For example, the complementary shapes of the proximal and distal ends of the neck region and the distal end of the first end region and the proximal end of the second end region may comprise a tab element and a socket element. The tab element may be configured to be thermally contracted or the socket element may be configured to be thermally expanded such that the tab element fits within the socket element, and when the tab and socket elements are brought to a same temperature while the tab element is received within the socket element, the tab element and the socket element may form a rigid connection. For example, the tab element may be configured to be thermally contracted from a first size to a second size, such that the second size may be configured to fit within the socket element, and when the tab and socket elements are brought to a same temperature while the tab element is fitted within the socket element, the tab element and the socket element may form a rigid connection. Alternatively, the socket element may be configured to be thermally expanded from a first size to a second size, such that the second size may be configured to receive the tab element therein, and when the tab and socket elements are brought to a same temperature while the tab element is received within the socket element, the tab element and the socket element may form a rigid connection.

The hybrid shunt further may comprise a retaining ring configured to be disposed over the tab and socket elements when the tab element is fitted within the socket element to maintain a rigid connection between the tab and socket elements. Moreover, an outer surface of the socket element may comprise one or more protrusions, such that the retaining ring maintains the rigid connection between the tab and socket elements via interference fit between the one or more protrusions and an inner surface of the retaining ring. In addition, the hybrid shunt further may comprise a physiological sensor disposed on the tab element, such that the physiological sensor is enclosed within the retaining ring when the retaining ring is disposed over the tab and socket elements. In some embodiments, the shape of the proximal and distal ends of the neck region may comprise the tab element, and the shape of the distal end of the first end region and the shape of the proximal end of the second end region may comprise the socket element. Alternatively, the shape of the proximal and distal ends of the neck region may comprise the socket element, and wherein the shape of the distal end of the first end region and the shape of the proximal end of the second end region may comprise the tab element.

The first and second end regions may be configured to self-expand from a collapsed delivery state to an expanded deployed state at body temperature. Accordingly, in the expanded deployed state, a proximal end of the first end region may flare outwardly from the distal end of the first end region at the first connection, and a distal end of the second end region may flare outwardly from the proximal end of the second end region at the second connection. In addition, in the expanded deployed state, the first connection may comprise a smooth, continuous transition from the neck region to the first end region, and the second connection may comprise a smooth, continuous transition from the neck region to the second end region.

In some embodiments, the distal end of the first end region may comprise a plurality of circumferentially spaced apart connectors configured to be permanently fixed to a corresponding plurality of circumferentially spaced apart connectors of the proximal end of the neck region at the first connection, and the proximal end of the second end region may comprise a plurality of circumferentially spaced apart connectors configured to be permanently fixed to a corresponding plurality of circumferentially spaced apart connectors of the distal end of the neck region at the second connection. For example, the plurality of circumferentially spaced apart connectors of the distal end of the first end region and the proximal end of the neck region may be permanently fixed along a single plane at the first connection, or alternatively, the plurality of circumferentially spaced apart connectors of the distal end of the first end region and the proximal end of the neck region may be permanently fixed in a staggered manner at the first connection, such that the connections do not all lie in a single plane. Additionally, the plurality of circumferentially spaced apart connectors of the proximal end of the second end region and the distal end of the neck region may be permanently fixed along a single plane at the second connection, or alternatively, the plurality of circumferentially spaced apart connectors of the proximal end of the second end region and the distal end of the neck region are permanently fixed in a staggered manner at the second connection, such that the connections do not all lie in a single plane.

The neck region may comprise NITINOL having an austenitic finish temperature (Af) between 45-60° C. In addition, the neck region may be configured to be mechanically expandable in vivo such that the passageway expands from a first cross-sectional area to a second cross-sectional area larger than the first cross-sectional area. Further, the neck region may be configured to be thermally contractible in vivo. Moreover, the first and second end regions may comprise NITINOL having an austenitic finish temperature (Af) between 5-20° C. Additionally, the first and second end regions and the neck region may comprise a diabolo-shaped shunt. The first and second end regions and the neck region may be at least partially encapsulated with a biocompatible material. In addition, the hybrid shunt further may comprise one or more physiological sensors disposed at the first and/or second connections. For example, the one or more physiological sensors may be configured to measure at least one of pressure, flow, velocity, temperature, or pH.

The hybrid shunt further may comprise a bridge extending from a first outer surface of the first end region to a second outer surface of the second end region. The bridge may be formed of biocompatible material and may be configured to engage the patient's atrial septum. For example, the first and second end regions and the neck region may be at least partially encapsulated with a biocompatible material integrally formed with the bridge. Alternatively, the first and second end regions and the neck region may be at least partially encapsulated with a biocompatible material different from the biocompatible material of the bridge. For example, the biocompatible material of the bridge may be configured to permit tissue ingrowth and the biocompatible material of the encapsulation may be configured to inhibit tissue ingrowth. Moreover, the biocompatible material of the bridge may have an internodal distance greater than the internodal distance of the biocompatible material of the encapsulation. For example, the internodal distance of the bridge material may be selected to permit tissue ingrowth while the internodal distance of the encapsulation material may be selected to inhibit tissue ingrowth. The biocompatible material of the bridge and the biocompatible material of the encapsulation may be expanded polytetrafluoroethylene (ePTFE). Moreover, the biocompatible material of the bridge may comprise a porosity selected to permit tissue ingrowth. Additionally, the bridge may be configured to remain engaged with the patient's atrial septum when the neck region is contracted.

BRIEF DESCRIPTION OF THE DRAWINGS

FIGS. 21A and 21B illustrate another example device with an internal dimension that can be reduced and increased in vivo having interlocking components and a retaining ring in an assembled configuration.

DETAILED DESCRIPTION

Figure 1A:
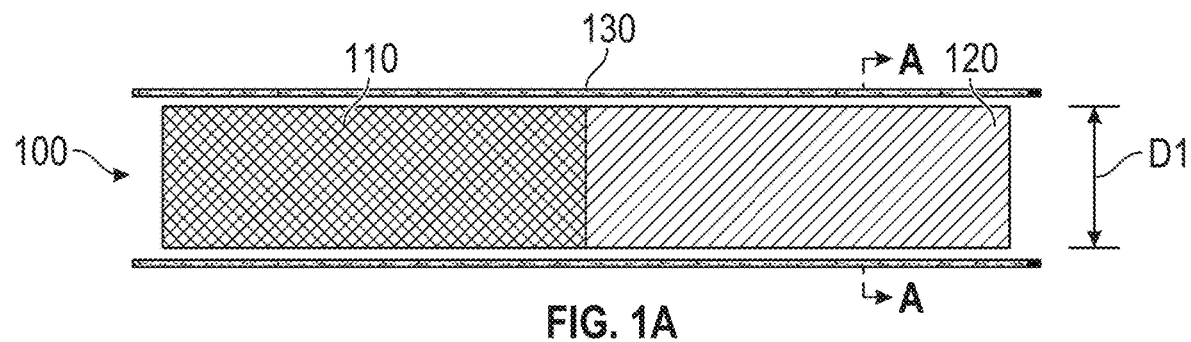
FIGS. 1A-1E schematically illustrate an example device with an internal dimension that can be reduced and increased in vivo.

The present disclosure provides devices with dimensions that can be reduced and increased in vivo, and methods of making and using the same. Described herein are apparatus and methods for making and using improved interatrial shunts to improve treatment and outcomes for patients with cardiovascular and cardiopulmonary disorders, such as pulmonary artery hypertension (PAH) or heart failure (HF). In some aspects, the devices have dimensions that can be reduced and increased in vivo.

For example, the present devices may be permanently or temporarily implantable in a human body and include one or more components which can be adjusted for size, larger or smaller, after implantation. The need for such adjustable devices may arise, for example, in the treatment of pulmonary artery hypertension (PAH) or heart failure (HF). In PAH, placing a shunt in the interatrial septum allows excessive blood pressure in the right atrium to be relieved by allowing some blood to flow from the right atrium to the left atrium through an orifice. In HF, placing a shunt in the interatrial septum allows excessive blood pressure in the left atrium to be relieved by allowing some blood to flow from the left atrium into the right atrium through an orifice. In both PAH and HF, interatrial shunting has been shown to effectively reduce symptoms and increase exercise tolerance. Interatrial shunting also may reduce the need for hospitalization and even improve life expectancy.

However, if the orifice of the interatrial shunt is too small, too little blood may be transferred and the shunt may be relatively ineffective and provide little or no clinical benefit. In contradistinction, shunting too much blood ("over-shunting") through too large of an orifice may lead to severe or even fatal complications over time. For example, in PAH patients, over-shunting may result in systemic oxygen desaturation and its sequalae including cyanosis, polycythemia with increased blood viscosity, end organ ischemia, and potentially death. In HF patients, over-shunting may result in pulmonary hypertension, right ventricular failure, and potentially death.

At present, there is no known way to predict the response of a given patient to a particular shunt orifice size. As is previously known, a shunt orifice may be increased in vivo, for example by dilating a suitably designed shunt by expanding an inflatable balloon catheter or other similar mechanically expansive means within the shunt, providing however, that the shunt is made from a malleable material and will remain expanded due to plastic deformation or some other physical property, whereby when the balloon or other expansive means is removed, the amount of elastic spring back or recoil will be low enough so that the desired increment in orifice size is achieved. One drawback of this approach is that the orifice size can only be increased. If the shunt starts out too large or if is made too large by balloon dilatation but the patient needs a smaller shunt, there is no way to go back to a smaller size orifice except by providing another, smaller shunt or placing a smaller shunt within the lumen of original shunt. This technique is known as "shunt-in-shunt." As such, finding a suitable shunt orifice size for a given patient has been a trial and error process in which the shunt orifice size is selected according to the patient's response, which may be observed for a period of time which may be as short as a few minutes or as long as many months, and the shunt orifice size increased (e.g., by balloon dilatation) or reduced (by providing a new, smaller shunt) depending on the patient's response. As such, opportunities to increase or reduce the size of the shunt are very limited and may not be repeatable. Furthermore, the extent to which an inflatable balloon catheter can expand a shunt orifice may be limited by the maximum size of the balloon. Thus, what is needed is a means to repeatedly and non-traumatically adjust the orifice size of shunts, and other implantable devices, in vivo, and in both directions, bigger or smaller.

Provided herein are devices with cross sectional areas that may be easily reduced in vivo, and expanded in vivo, in any order, as clinically necessary. In some examples, the devices provided herein may incorporate technology with adjustable cross-sectional flow areas that may be easily reduced in vivo and/or expanded in vivo, in any order, as clinically necessary. Examples of interatrial shunts with adjustable cross-sectional flow areas are described in U.S. Pat. No. 9,724,499 to Rottenberg, U.S. Pat. No. 10,898,698 to Eigler, WO 2021/224736, and U.S. Pat. No. 11,744,589 to Ben-David, each assigned to the assignee of the present application, the entire contents of each of which are incorporated herein by reference. In particular, some examples of the present devices include a self-expanding superelastic (austenitic phase) material as well as a malleable shape-memory (martensitic phase) material. When the device is implanted in the human body, e.g., by transporting the device in a compressed state within a sheath to a desired location and then removing the sheath, the self-expanding superelastic material may automatically deploy to its desired size, while the malleable shape-memory material initially may remain in a reduced size state. The cross sectional area of the malleable shape-memory material then may be expanded and reduced in vivo as desired so as to obtain a cross sectional area that is suitable for treating the patient, e.g., by providing a suitable fluid flow rate therethrough, or so as to appropriately fixate the device within the patient while allowing for repositioning to improve effectiveness of the treatment. A wide variety of devices may be prepared using components respectively including self-expanding superelastic materials and malleable shape-memory materials, such as exemplified herein.

In some examples, the present devices may be or include hourglass or "diabolo" shaped shunts, which optionally are encapsulated with biocompatible material, and which may be used for treating subjects suffering from disorders for which regulating fluid flow may be useful, such as CHF or PAH. In some examples, the hourglass shaped shunts may be specifically configured to be lodged securely in the atrial septum, for example in an opening through the fossa ovalis, to allow blood flow from the left atrium to the right when blood pressure in the left atrium exceeds that of the right atrium, or blood flow from the right atrium to the left when blood pressure in the right atrium exceeds that of the left atrium. As provided herein and described in greater detail in the above-incorporated PCT application WO 2021/224736, the internal dimension of the hourglass shaped shunt suitably may be adjusted in vivo, for example, so as to adjust the flow of fluid therethrough, e.g., so as to adjust the flow of fluid between the left atrium and the right atrium through the atrial septum.

FIGS. 1A-1E schematically illustrate an example device with an internal dimension that can be reduced and increased in vivo. Device 100 illustrated in FIGS. 1A-1E includes first component 110 and second component 120 coupled, e.g., fluidically coupled, to first component 110. First component 110 may include a self-expanding superelastic material, and second component 120 may include a malleable shape-memory material. The malleable shape-memory material of second component 120 may have a first cross sectional area permitting a first rate of fluid flow through the second component, may be expandable to a second cross sectional area permitting a second rate of fluid flow through the second component, and may be contractible to a third cross sectional area permitting a third rate of fluid flow through the second component. Note that the overall rate of fluid flow through device 100 also may depend on the cross sectional area of first component 110.

Figure 1B:
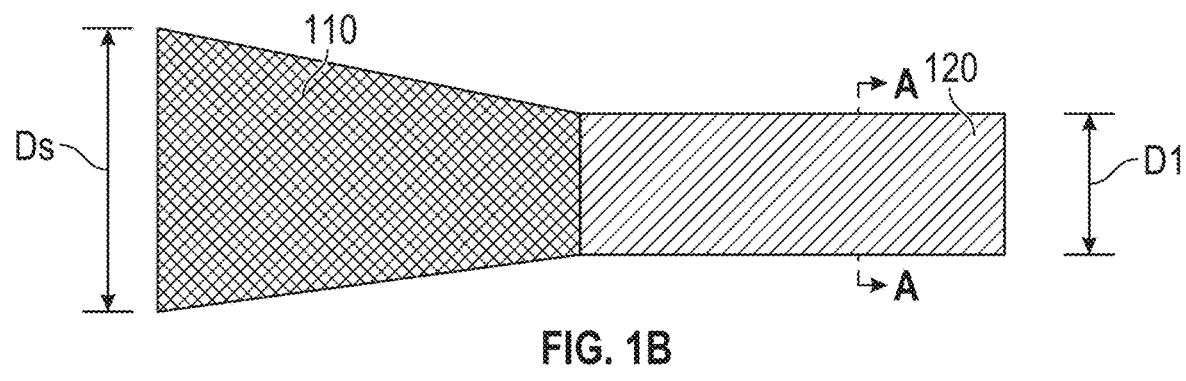
Figure 1C:
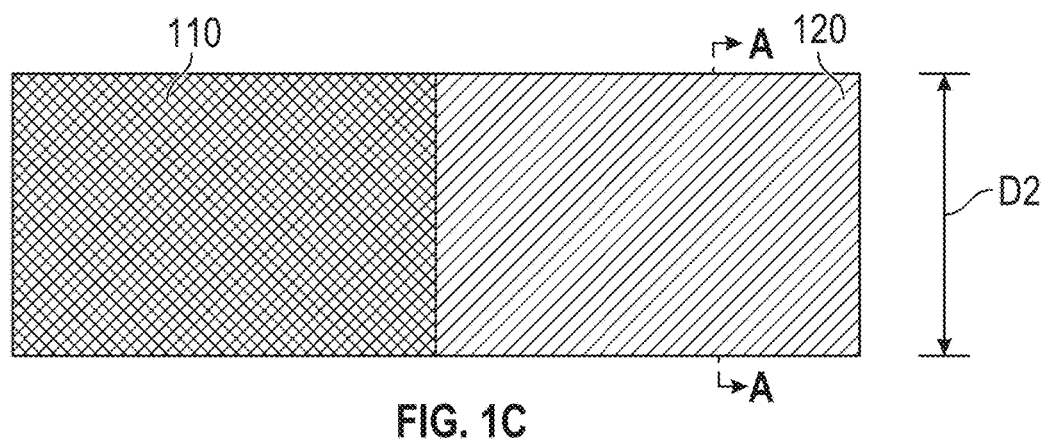
Figure 1D:
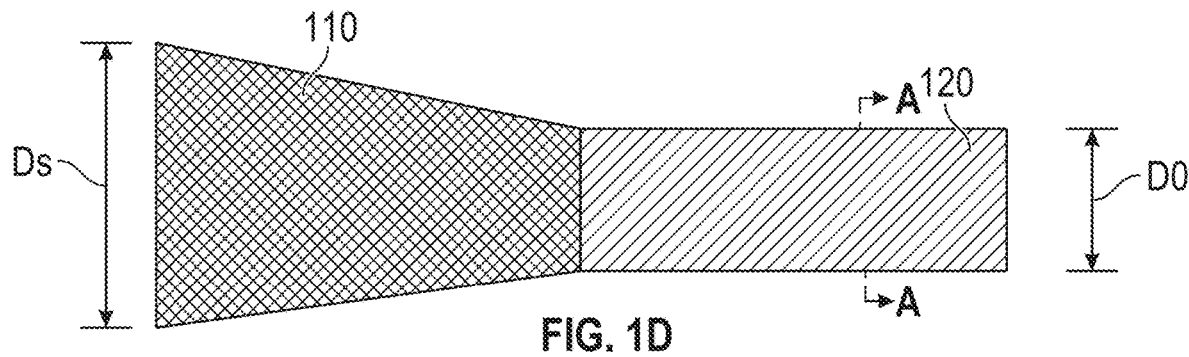
Figure 1E:
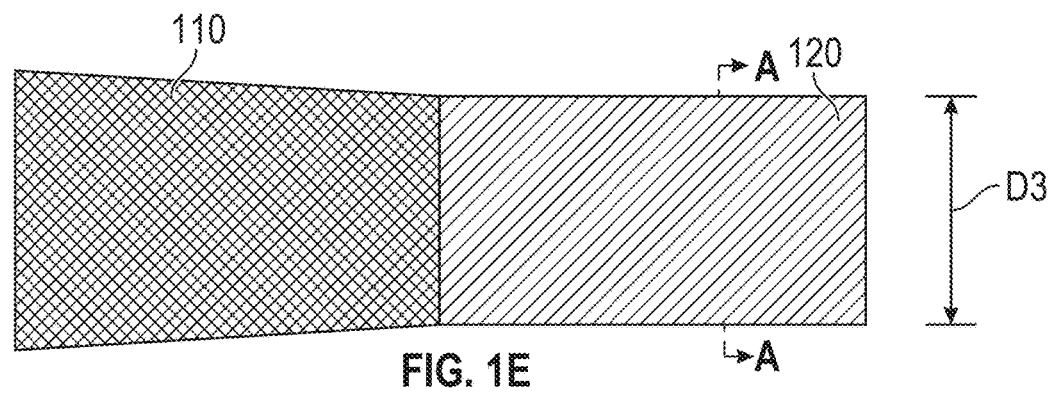

For example, FIG. 1A schematically illustrates device 100 in a compressed or crimped state and loaded into sheath 130 for percutaneous implantation within the human body. In the crimped state, both first component 110 and second component 120 may have a dimension D1 (corresponding to a first cross sectional area). Once device 100 is delivered to the desired location, sheath 130 may be retracted so as to percutaneously implant the device. As illustrated in FIG. 1B, following removal of sheath 130 the self-expanding superelastic material of first component 110 may automatically expand to its heat-set superelastic configuration, in this example with dimension Ds, while the malleable shape-memory material of second component 120 may remain in the crimped state (e.g., at the first dimension, D1, corresponding to a first cross sectional area) until it is further adjusted. Second component 120 may be expanded by any suitable amount, for example such as shown in FIG. 1C, to dimension D2 (corresponding to a second cross sectional area). Second component 120 may be reduced by any suitable amount, for example such as shown in FIGS. 1D and 1E, by first using the shape-memory property to contract component 120 to its annealed configuration dimension D0, then expanding (e.g., by balloon dilation) to dimension D3 (corresponding to a third cross sectional area). Based on the particular dimension (and cross sectional areas) to which second component 120 is adjusted by expansion or contraction, different rates of fluid flow may be permitted through that component, thus providing an adjustable orifice for controlling the flow of fluid within the location of the human body in which device 100 is deployed.

In some examples, reducing the dimension of a shape memory material-based component herein always returns that component to its heat-set (annealed) dimension, D0, determined at the time of manufacture by heat setting within a jig. Once the dimension is thus reduced it may be then expanded, for example by balloon dilation, to an intermediate dimension. Additionally, note that although in some examples D0 and D1 may be approximately the same as one another, in other examples D0 may be smaller than D1, while in still other examples D0 may be larger than D1. Although FIGS. 1A-1E illustrate only four exemplary dimensions D0, D1, D2, D3 of second component 120, it should be appreciated that any suitable dimension above a minimum set by the annealed configuration, D0, may be obtained by balloon expanding as desired. For example, D2 may be smaller than D3. Alternatively, D2 may be larger than D3, and D3 may be achieved by reducing second component 120 to its heat-set dimension, D0, as shown in FIG. 1D, and then expanding second component 120 to dimension D3 as shown in FIG. 1E. In some examples, the second component may be heated with a hot balloon and the balloon then deflated to a desired dimension, followed by cooling of the second component. As heating creates a crystalline phase change, the dimension of the second component is never plastically deformed by balloon inflation and therefore, the shunt can be repeatedly cycled from one dimension to another, bigger or smaller through any number of cycles the patient requires to optimize shunt size.

Note that as used herein, "inner dimension" refers to the transverse dimension between inner walls of a device component, e.g., along line A-A indicated in FIGS. 1A-1E. As used herein, "outer dimension" refers to the transverse dimension between outer walls of a device component, e.g., along line A-A indicated in FIGS. 1A-1E. As used herein, "cross sectional area" refers to the area of the transected plane within the walls of the device in a plane running through that dimension, e.g., in a plane parallel to line A-A indicated in FIGS. 1A-1E and crossing through second component 120. The expansion or contraction of a dimension may be with reference to the distance between walls of the device component at a particular location within that component, e.g., along line A-A indicated in FIGS. 1A-1E. The expansion or contraction of a cross sectional area may be with reference to area within the walls of the device in a plane running through the corresponding dimension of the device component at a particular location within that component, e.g., along line A-A indicated in FIGS. 1A-1E. The present devices may have any suitable cross sectional shape and may include, but are not limited to, circular, or uniform, cross sections.

In the nonlimiting examples shown in FIGS. 1B and 1D, the interface between the crimped state of second component 120 and expanded first component 110 may apply a force that inhibits first component 110 from fully expanding; it should be appreciated that such interface instead may apply a force that causes second component 120 to partially expand. As described in greater detail below, the particular manner in which first component 110 and second component 120 are joined to one another may be selected so as to control the force(s) applied to such components and thus the shapes and dimensions of such components.

In some examples, the self-expanding superelastic material of first component 110 and the malleable shape-memory material of second component 120 may include different materials than one another, or may include the same material as one another but having different phases than one another. For example, first component 110 and second component 120 independently may include one or more materials selected from the group consisting of nickel titanium (NiTi), also known as NITINOL, other shape memory alloys, self-expanding materials, superelastic materials, polymers, and the like. For example, first component 110 may include a NITINOL alloy having an austenitic finish temperature (Af) that is sufficiently below body temperature that the material is in an austenitic, superelastic phase while in the human body. In one non-limiting example, the self-expanding superelastic material of first component 110 includes NITINOL having an Af of less than 37° C. For example, the Af of the NITINOL of the self-expanding superelastic material may be between 5-20° C. First component 110 and second component 120 optionally may be integrally formed from a common frame with one another. For example, first component 110 and second component 120 may be initially cut and processed as a single unit from the same tubing, sheet, or other suitable configuration of frame as one another. Portions of that common frame may be heat treated differently than one another so as to define first component 110 and second component 120, e.g., in a manner similar to that described with reference to FIGS. 10A-10C.

Second component 120 may include a NITINOL alloy having an austenitic phase transition temperature Af that is slightly above body temperature such that the material remains in its martensitic, shape-memory phase while in the body unless and until it is heated to or above its Af, for example by the injection of warm or hot saline (or other fluid) into the fluid within or flowing through second component 120, or by applying heat through electrical energy such as with an RF energy source. In one nonlimiting example, the malleable shape-memory material of second component 120 includes NITINOL having an austenitic finish temperature (Af) of greater than 37° C. For example, the Af of the NITINOL of the malleable shape-memory material of second component 120 may be between 40-60° C., e.g., from 45-60° or 50-55° C. In some examples, the warm or hot saline (or other fluid) may be injected sufficiently close to second component 120 to heat that component to or above its Af, using a side-hole catheter positioned through device 100. In other examples, a pair of RF electrodes may be brought into contact with device 100, e.g., via a catheter, and actuated at a sufficient voltage and frequency to heat component 120 to or above its Af. In still other examples, any other suitable means of locally applying heat to device 100, such as a laser, magnetic inductance, electrical resistance, or the like, may be used. Heating device 100 using electrical resistance may include contacting the device with a pair of electrodes, e.g., via a catheter, and passing a current through the device that causes heating of the device. Heating device 100 using a laser may include irradiating the device with light from a laser that may be introduced by a catheter. Heating device 100 using magnetic inductance may include passing an alternating magnetic field through the device that induces eddy currents inside the device which heat the device. Note that in blood vessels having a particularly high rate of blood flow (e.g., 2-5 L/min), such as the aorta or internal iliac artery, it may be useful to heat device 100 using direct heating methods, such as using RF energy, a laser, magnetic inductance, or electrical resistance, instead of saline which may be washed away by the high blood flow rate before sufficiently heating the device.

Alternatively, device 100 may include a single NITINOL alloy (common frame) that has been heat treated to produce a lower Af in a region corresponding to first component 110, and that has been heat treated to produce a higher Af in a region corresponding to second component 120, such that first component 110 and second component 120 are integrally formed with one another. The malleable shape-memory material of second component 120 may be expandable and contractible using any suitable technique. For example, the malleable shape-memory material of second component 120 may be mechanically expanded, e.g., using balloon dilatation such as known in the art. Additionally, or alternatively, malleable shape-memory material of second component 120 may be thermally contracted, e.g., using saline at a temperature at or above the Af of that material, or otherwise heated such as with RF energy or the use of a laser, magnetic inductance, electrical resistance, or the like in a manner such as described above.

Optionally, first component 110 may be configured to engage a lumen in the body, for example in a manner such as described in U.S. Pat. No. 10,898,698 to Eigler, entitled "Devices with dimensions that can be reduced and increased in vivo, and methods of making and using the same," the entire contents of which are incorporated by reference herein. For example, the lumen may include a blood vessel, and the first component may be configured to engage the blood vessel.

It will be appreciated that the present devices may include any suitable number of components including a self-expanding superelastic material, and any suitable number of components including a malleable shape-memory material. For example, FIGS. 2A-2E schematically illustrate another example device with an internal dimension that can be reduced and increased in vivo. Device 200 illustrated in FIGS. 2A-2E includes first component 210, second component 220, and third component 211 which is coupled, e.g., fluidically coupled, to first component 210 and second component 220. First component 210 may include a first self-expanding superelastic material, second component 220 may include a malleable shape-memory material, and third component 211 may include a second self-expanding superelastic material. The malleable shape-memory material of second component 220 may have a first cross sectional area permitting a first rate of fluid flow through the second component, may be expandable to a second cross sectional area permitting a second rate of fluid flow through the second component, and may be contractible to a third cross sectional area permitting a third rate of fluid flow through the second component.

Figure 2A:
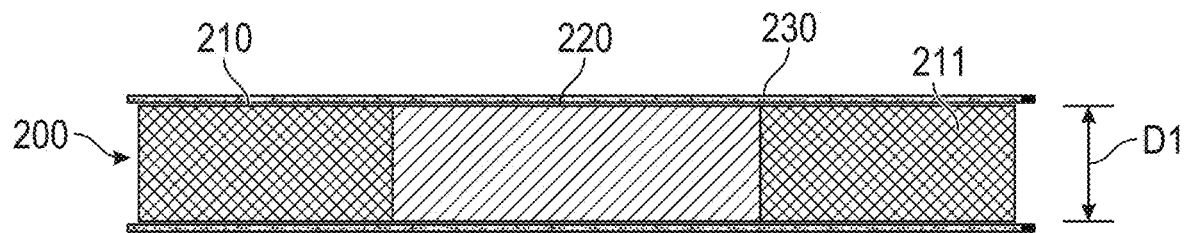
FIGS. 2A-2E schematically illustrate another example device with an internal dimension that can be reduced and increased in vivo.
Figure 2B:
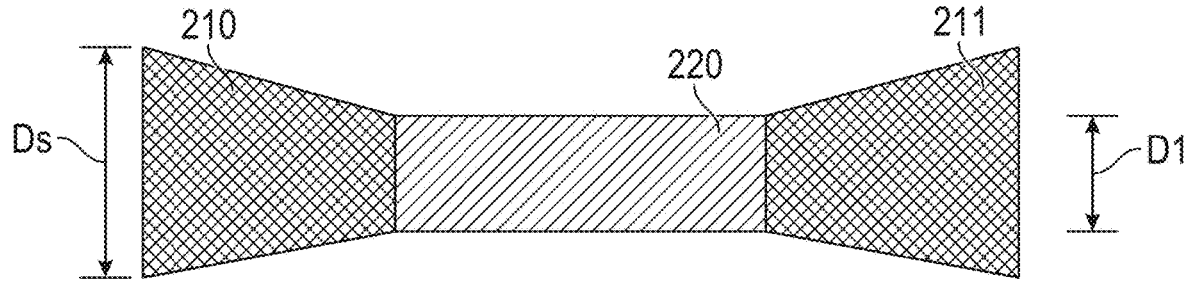
Figure 2C:
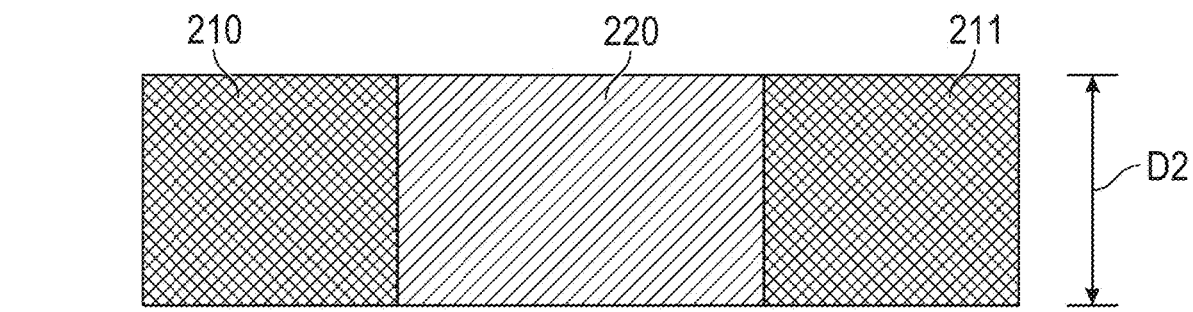
Figure 2D:
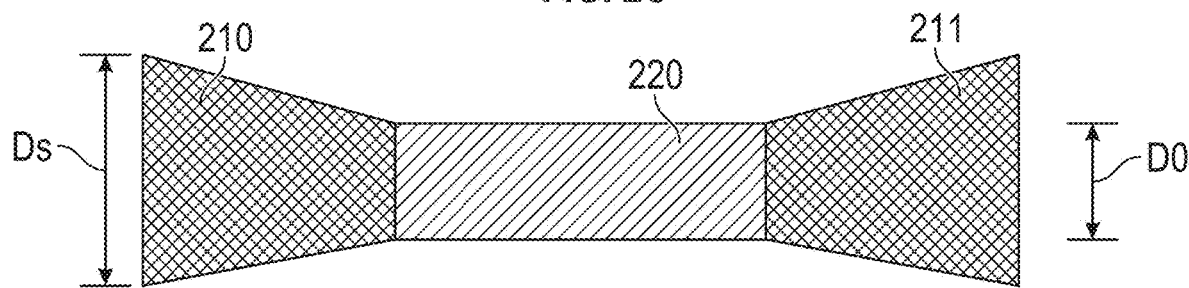
Figure 2E:
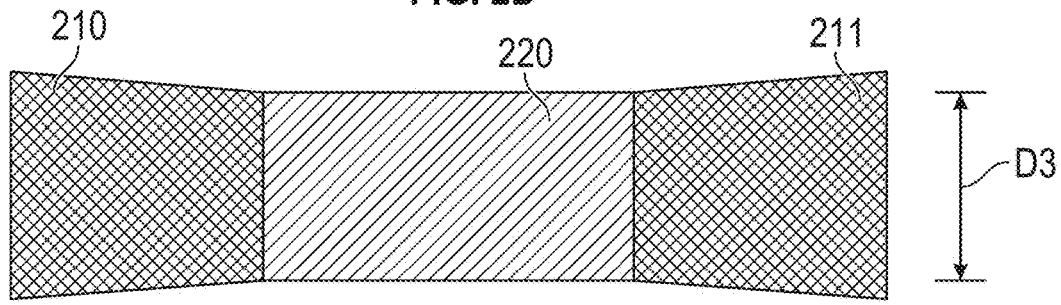

For example, FIG. 2A schematically illustrates device 200 in a crimped state and loaded into sheath 230 for percutaneous implantation within the human body. In the crimped state, first component 210, second component 220, and third component 211 may have a dimension D1 (corresponding to a first cross sectional area). Once device 200 is delivered to the desired location, sheath 230 may be retracted so as to percutaneously implant the device. As illustrated in FIG. 2B, following removal of sheath 230 the respective self-expanding superelastic materials of first component 210 and third component 211 may automatically expand to a heat-set dimension Ds, while the malleable shape-memory material of second component 220 may remain in the crimped state (e.g., at the first cross sectional area) until it is further adjusted. Second component 220 may be expanded by any suitable amount, for example such as shown in FIG. 2C, to dimension D2 (corresponding to a second cross sectional area). Second component 220 may be reduced by any suitable amount in the same manner as described above in relation to FIG. 1, for example such as shown in FIG. 2E, to dimension D3 (corresponding to a third cross sectional area), by first heating the shape-memory component 220 above its Af temperature, returning it so its annealed configuration, D0, as shown in FIG. 2D, then expanding it (e.g. by balloon dilation) to a third dimension D3 (corresponding to a third cross sectional area). Based on the particular dimension (and cross sectional areas) to which second component 220 is adjusted by expansion or contraction, different rates of fluid flow may be permitted through that component, thus providing an adjustable orifice for controlling the flow of fluid within the location of the human body in which device 200 is deployed. Note that the overall rate of fluid flow through device 200 also may depend on the cross sectional areas of first component 210 and second component 211.

Although FIGS. 2A-2E illustrate only three exemplary dimensions D1, D2, D3 of second component 220, it should be appreciated that any suitable dimension may be obtained by expanding or contracting the second component as desired. Note that although in some examples D0 and D1 may be approximately the same as one another, in other examples D0 may be smaller than D1, while in still other examples D0 may be larger than D1. Furthermore, it should be appreciated that a shape-memory component may be formed and heat set into other geometries besides the circular cylindrical shape illustrated here, and that its shape may be modified in other ways besides the radial expansion illustrated here, and that the shape-memory component may be returned to its original, heat-set, geometry by heating it above its Af temperature. Additionally, with regards to each of the examples described herein, it should be appreciated that the components need not necessarily have circular cross sections, but may have any suitable shape of cross section.

In the nonlimiting examples shown in FIGS. 2B and 2D, the respective interfaces between the crimped state of second component 220 and expanded first component 210 and expanded third component 211 may apply a force that inhibits first component 210 and third component 211 from fully expanding; it should be appreciated that such interface(s) instead may apply a force that causes second component 220 to partially expand. As described in greater detail below, the particular manner in which first component 210, second component 220, and third component 211 respectively are joined to one another may be selected so as to control the force(s) applied to such components and thus the shapes and dimensions of such components. First component 210 and third component 211 may be, but need not necessarily be, the same dimension, shape, and size as one another.

In some examples, the first self-expanding superelastic material of first component 210, the malleable shape-memory material of second component 220, and the second self-expanding superelastic material of third component 211 may include different materials than one another, or may include the same material as one another but having different phases than one another. For example, first component 210, second component 220, and third component 211 independently may include one or more materials selected from the group consisting of nickel titanium (NiTi), also known as NITINOL, other shape memory alloys, self-expanding materials, superelastic materials, polymers, and the like. In one nonlimiting example, first component 210 and third component 211 each may include a NITINOL alloy having an Af that is sufficiently below body temperature that the material is in an austenitic, superelastic phase while in the human body in a manner such as described with reference to FIGS. 1A-1E. Second component 220 may include a NITINOL alloy having an austenitic phase transition temperature Af that is slightly above body temperature such that the material remains in its martensitic, shape-memory phase while in the body unless and until it is heated to its Af, for example by the injection of warm or hot saline into the fluid within or flowing through second component 220 or the application of RF energy, or the use of a laser, magnetic inductance, electrical resistance, or the like in a manner such as described with reference to FIGS. 1A-1E. Alternatively, device 200 may include a single NITINOL alloy that has been heat treated to produce a lower Af in regions respectively corresponding to first component 210 and third component 211, and that has been heat treated to produce a higher Af in a region corresponding to second component 220. The malleable shape-memory material of second component 220 may be expandable and contractible using any suitable technique, e.g., such as described with reference to FIGS. 1A-1E. First component 210, second component 220, and third component 211 optionally may be integrally formed from a common frame with one another in a manner such as described with reference to FIGS. 1A-1E.

In a manner such as described in greater detail with reference to FIGS. 7-10C, first component 210 may provide an inlet, second component 220 may provide a neck, and third component 211 may provide an outlet coupled, e.g., fluidically coupled, to the inlet via the neck. As used herein, "inlet" means component with ingress of blood flow, and "outlet" means component with outgress (egress) of blood flow. The particular components that respectively may be used to provide ingress and outgress (egress) of blood flow may be selected based on the condition being treated. For example, in HF, the inlet may be on the left atrial (LA) side, where blood flow from LA to right atrium (RA), and LA decompression, are desirable. In contradistinction, in PAH, the interatrial pressure gradient is reversed causing R to L flow and RA decompression, and the inlet is on the RA side. The cross sectional area of the neck may be smaller than the cross sectional areas of at least one of the inlet and the outlet, for example as described in greater detail with reference to FIGS. 7-10C. Third component 211 may be configured to engage an opening in the human body, for example in a manner such as described with reference to FIGS. 7-10C. As described in U.S. Pat. No. 10,898,698 to Eigler, the cross sectional area of the neck may be larger than respective cross sectional areas of at least one of the inlet and the outlet, first component 210 and/or third component 211 may be configured to engage a lumen in the body, e.g., a blood vessel, and/or the neck, if present, optionally may be configured to be disposed adjacent to an ostium of the blood vessel.

FIGS. 3A-3D schematically illustrate an example device with multiple internal dimensions that can be reduced and increased in vivo. Device 300 illustrated in FIGS. 3A-3D includes first component 310, second component 320, and third component 321 which is coupled, e.g., fluidically coupled, to first component 310 and second component 320. First component 310 may include a self-expanding superelastic material, second component 320 may include a first malleable shape-memory material, and third component 321 may include a second malleable shape-memory material. The respective malleable shape-memory materials of second component 320 and third component 321 may have a first cross sectional area permitting a first rate of fluid flow through the second component, may be expandable to a second cross sectional area permitting a second rate of fluid flow through the second component, and may be contractible to a third cross sectional area permitting a third rate of fluid flow through the second component. Note that the cross sectional areas, sizes, and shapes of second component 320 and third component 321 may be, but need not necessarily be, the same as one another. Note that the overall rate of fluid flow through device 200 also may depend on the cross sectional areas of first component 210 and second component 211. Illustratively, in examples where the cross sectional area of second component 320 is smaller than that of third component 321, or where the cross sectional area of second component 320 is larger than that of third component 321, the smaller of the cross sectional areas may define the rate of fluid flow through device 300.

Figure 14A:
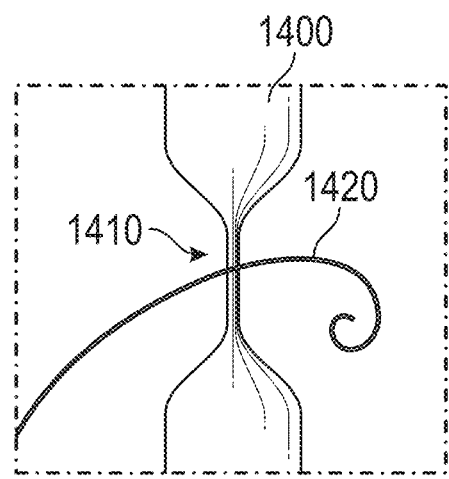
FIGS. 14A-14I schematically illustrate use of the delivery device of FIGS. 13A-13D in the human body.

In addition to defining the rate of fluid flow through device 300, examples such as described with reference to FIGS. 3A-3D may allow for controllably adjusting apposition for anchoring or fixating the device to the wall of a body space by balloon expansion of apposing components 320, 321, e.g., in a manner such as described with reference to FIGS. 14A-14C, while allowing these apposing components to be contracted so that the device may be repositioned after deployment. Additionally, or alternatively, examples such as described with reference to FIGS. 3A-3D may provide for a relatively safe method of implantation as compared, for example, to expanding the first, second, and third components 310, 320, 321 all together with one another. For example, in an implementation such as described in U.S. Pat. No. 10,898,698 to Eigler, expanding the first, second, and third components 310, 320, 321 all together with one another may cause blockage of the branch arteries. Allowing for selective expansion of specific segments in a more gradual manner can be safer.

Figure 3A:
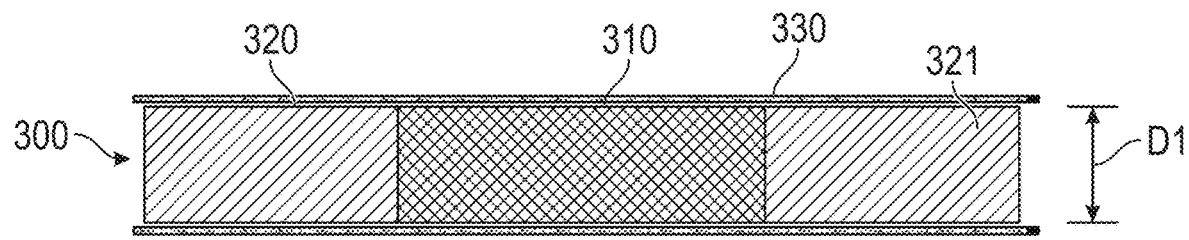
FIGS. 3A-3D schematically illustrate an example device with multiple internal dimensions that can be reduced and increased in vivo.
Figure 3B:
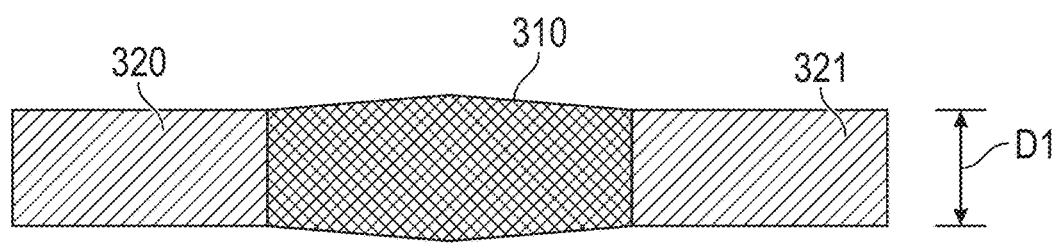
Figure 3C:
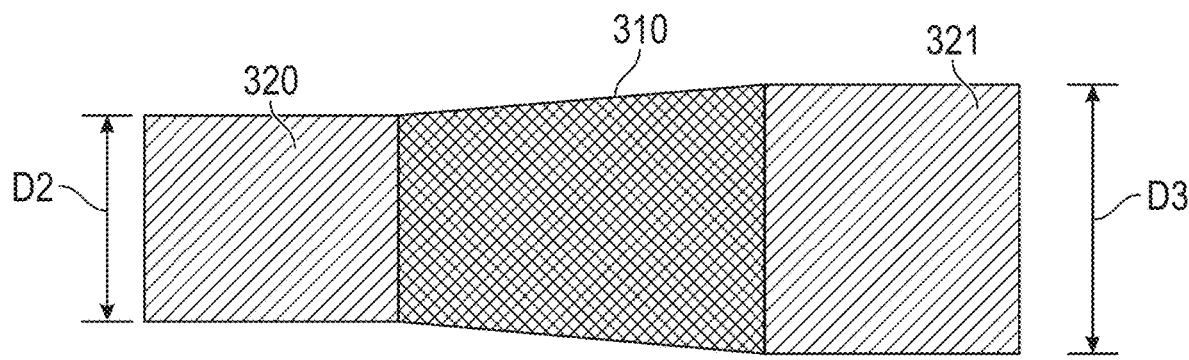

FIG. 3A schematically illustrates device 300 in a crimped state and loaded into sheath 330 for percutaneous implantation within the human body. In the crimped state, first component 310, second component 320, and third component 321 may have a dimension D1 (corresponding to a first cross sectional area). Once device 300 is delivered to the desired location, sheath 330 may be retracted so as to percutaneously implant the device. As illustrated in FIG. 3B, following removal of sheath 330 the self-expanding superelastic material of first component 310 may automatically expand, while the first malleable shape-memory material of second component 320 and the second malleable shape-memory material of third component 321 may remain in the crimped state (e.g., at the first cross sectional area) until they are further adjusted. Second component 320 and third component 321 independently may be expanded by any suitable amount, for example such as shown in FIG. 3C, to respective dimensions D2 (corresponding to a second cross sectional area) and D3. Second component 320 and third component 321 independently may be reduced to their respective heat-set dimensions and then expanded by any suitable amount, for example such as shown in FIG. 3D, to respective dimensions D4 (corresponding to a third cross sectional area) and D5.

Based on the particular dimensions (and cross sectional areas) to which second component 320 and third component 321 independently are adjusted by expansion or contraction, different rates of fluid flow may be permitted through such components, thus providing an adjustable orifice for controlling the flow of fluid within the location of the human body in which device 300 is deployed. Although FIGS. 3A-3D illustrate exemplary dimensions D1, D2, D3, D4, and D5 to which second component 320 and third component 321 independently may be set, it should be appreciated that any suitable dimension(s) may be obtained by independently expanding or contracting the second component and third components as desired. For example, second component 320 and third component 321 may have respective heat-set dimensions D0 that may be the same as, or different than, one another, and may be crimped to dimension D1 which is smaller than DO. Second component 320 and third component 321 respectively may be expanded to any suitable dimension(s), reset to D0, and subsequently re-expanded to any suitable dimension(s) any suitable number of times.

Figure 3D:
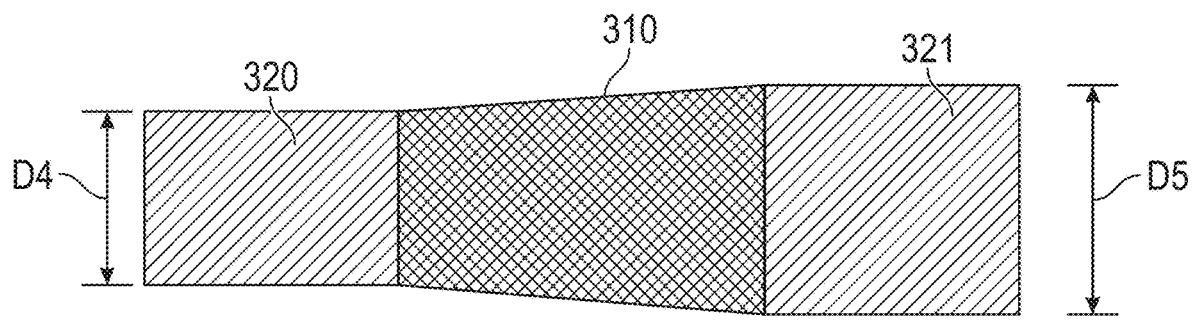

In the nonlimiting examples shown in FIGS. 3B and 3D, the respective interfaces between the crimped state of second component 320 and third component 321 and expanded first component 310 may apply forces that inhibit first component 310 from fully expanding; it should be appreciated that such interfaces instead may apply respective forces that cause second component 320 or third component 321 to partially expand. As described in greater detail below, the particular manner in which first component 310, second component 320, and third component 321 respectively are joined to one another may be selected so as to control the force(s) applied to such components and thus the shapes and dimensions of such components.

In some examples, the self-expanding superelastic material of first component 310, the first malleable shape-memory material of second component 320, and the second malleable shape-memory material of third component 321 may include different materials than one another, or may include the same material as one another but having different phases than one another. For example, first component 310, second component 320, and third component 321 independently may include one or more materials selected from the group consisting of nickel titanium (NiTi), also known as NITINOL, other shape memory alloys, self-expanding materials, superelastic materials, polymers, and the like. In one nonlimiting example, first component 310 may include a NITINOL alloy having an Af that is sufficiently below body temperature that the material is in an austenitic, superelastic phase while in the human body in a manner such as described with reference to FIGS. 1A-1E. Second component 320 and third component 321 each may include a NITINOL alloy having an austenitic phase transition temperature Af that is slightly above body temperature such that the material remains in its martensitic, shape-memory phase while in the body unless and until it is heated to its Af, for example by the respective injection of warm or hot saline into the fluid within or flowing through second component 320 or third component 321 or the application of RF energy, or the use of a laser, magnetic inductance, electrical resistance, or the like in a manner such as described with reference to FIGS. 1A-1E. Alternatively, device 300 may include a single NITINOL alloy that has been heat treated to produce a lower Af in a region corresponding to first component 310, and that has been heat treated to produce a higher Af in regions respectively corresponding to second component 320 and third component 321. Second component 320 and third component 321 may, but need not necessarily, have the same material or the same Af as one another. The respective malleable shape-memory materials of second component 320 and third component 321 may be independently expandable relative to one another using any suitable technique, e.g., such as described with reference to FIGS. 1A-1E, may be reset to their respective heat-set dimensions, and then independently re-expanded to respective dimensions. First component 310, second component 320, and third component 321 optionally may be integrally formed from a common frame with one another in a manner such as described with reference to FIGS. 1A-1E.

In a manner such as described in U.S. Pat. No. 10,898,698 to Eigler, the cross sectional areas of second component 320 and third component 321 may be expanded independently from one another so as to fixate the device within the lumen while allowing for repositioning. Moreover, second component 320 may be configured as an inlet, and third component 321 may be configured as an outlet fluidically coupled to the inlet via first component 310. Additionally, the inlet 320 may be configured to engage a blood vessel in the human body, and the outlet 321 may be configured to extend into an ostium of the blood vessel. A fourth component may be fluidically coupled to first component 310 and configured to extend into another ostium of the blood vessel. In some example, first component 310 may be configured to provide a fluidic pathway for blood flow, for example, to channel blood flow past the weak segment of an aneurism, such as an aortic aneurism. In order to effectively protect the aneurism from the stress of aortic pressure, the inlet 320, outlet 321, and fourth component may be expanded so as to form sufficiently tight seals with their respective blood vessel(s).

In the present devices, such as exemplified by devices 100, 200, 300 respectively described with reference to FIGS. 1A-1E, 2A-2E, and 3A-3D, the first, second, and (if present) third components may be coupled, e.g., fluidically coupled, to one another using any suitable manner(s) of joining. For example, any malleable shape-memory material (such as in component 120, 220, 320, or 321) optionally and independently may be joined to any self-expanding superelastic material (such as in component 110, 210, 211, or 310) by welding. Additionally, or alternatively, any malleable shape-memory material (such as in component 120, 220, 320, or 321) optionally and independently may be joined to any self-expanding superelastic material (such as in component 110, 210, 211, or 310) using an encapsulant which may cover at least a portion of at least one of the components, and which may join such components to one another. Additionally, or alternatively, any shape-memory material and any self-expanding superelastic material may be integrally formed from a common frame with one another.

Figure 4A:
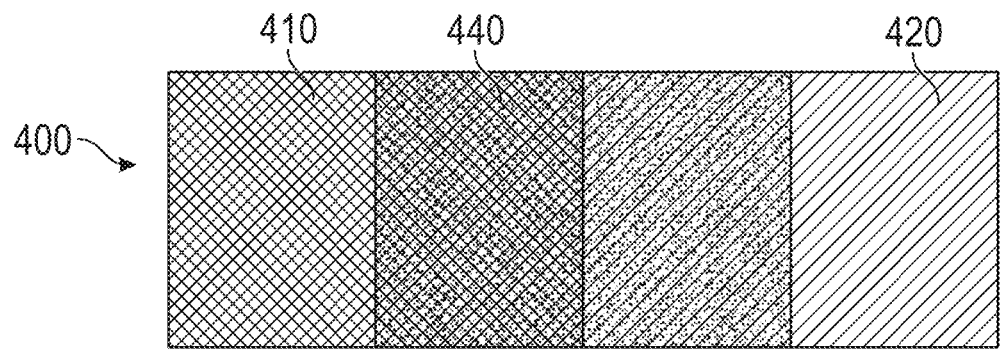
FIGS. 4A-4B schematically illustrate example encapsulants that may be provided in a device with an internal dimension that can be reduced and increased in vivo.
Figure 4B:
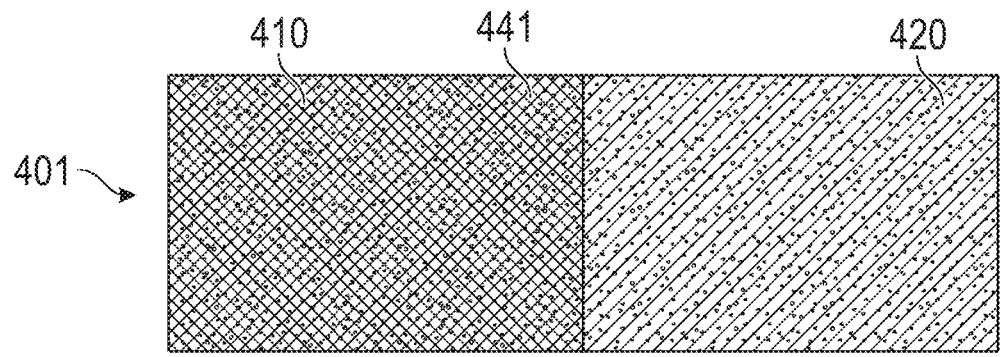

For example, FIGS. 4A-4B schematically illustrate example encapsulants that may be provided in a device with an internal dimension that can be reduced and increased in vivo. In example device 400 illustrated in FIG. 4A, which may include any suitable number of components (only two components illustrated for simplicity), encapsulant 440 covers a portion of each of first component 410 and second component 420, which components may be configured similarly as described with reference to FIGS. 1A-1E, 2A-2E, or 3A-3D. Encapsulant 440 may fluidically join the malleable shape-memory material (e.g., of component 420) to the self-expanding superelastic material (e.g., of component 410). Optionally, encapsulant 440 indirectly and elastically joins the malleable shape-memory material to the self-expanding superelastic material. In example device 401 illustrated in FIG. 4B, which may include any suitable number of components (only two components illustrated for simplicity), encapsulant 441 covers the entirety of each of first component 410 and second component 420, which components may be configured similarly as described with reference to FIGS. 1A-1E, 2A-2E, or 3A-3D. Encapsulants 440 or 441 may fluidically join the malleable shape-memory material (e.g., of component 420) to the self-expanding superelastic material (e.g., of component 410). It will be appreciated that in other examples (not specifically illustrated), an encapsulant may entirely cover one or more components, and may only partially cover one or more other components. The encapsulant may indirectly couple one or more components to one another. A combination of encapsulation and mechanically engaging, e.g., welding or mechanical interference, may be used to both directly and indirectly couple the present components to one another.

Encapsulants 440, 441 may include any suitable biocompatible material, such as a polymer or a natural material. Examples of polymers suitable for use as an encapsulant include expanded polytetrafluoroethylene (ePTFE), silicone, polycarbonate urethane, DACRON (polyethylene terephthalate), Ultra High Molecular Weight Polyethylene (UHMWPE), and polyurethane. Examples of natural materials suitable for use as an encapsulant include pericardial tissue, e.g., from an equine, bovine, or porcine source, or human tissue such as human placenta or other human tissues. The biocompatible material is preferably smooth so as to inhibit thrombus formation, and optionally may be impregnated with carbon so as to promote tissue ingrowth. Alternatively, to promote tissue ingrowth and endothelization, the biocompatible material may form a mesh-like structure. The present devices may be encapsulated with a biocompatible material in a manner similar to that described in U.S. Pat. Nos. 11,304,831 and 10,835,394 to Nac, U.S. Pat. No. 11,109,988 to Rosen, U.S. Pat. Nos. 9,034,034 and 9,980,815 to Nitzan, and U.S. Pat. No. 10,076,403 to Eigler, the entire contents of each of which are incorporated by reference herein. For example, an inner surface of one of the present devices may be covered with a first graft layer, and an outer surface of the device may be covered with a second graft layer. The graft layers may be securely bonded together to form a monolithic layer of biocompatible material, e.g., may be sintered together to form a strong, smooth, substantially continuous coating that covers the inner and outer surfaces of the device. Portions of the coating then may be removed as desired from selected portions of the device using laser-cutting or mechanical cutting, for example.

In one example, the device is encapsulated with ePTFE. It will be understood by those skilled in the art that ePTFE materials have a characteristic microstructure consisting of nodes and fibrils, with the fibrils orientation being substantially parallel to the axis of longitudinal expansion. Expanded polytetrafluoroethylene materials may be made by ram extruding a compressed billet of particulate polytetrafluoroethylene and extrusion lubricant through an extrusion die to form sheet or tubular extrudates. The extrudate is then longitudinally expanded to form the node-fibril microstructure and heated to a temperature at or above the crystalline melt point of polytetrafluoroethylene, i.e., 327° C., for a period of time sufficient to sinter the ePTFE material. Heating may take place in a vacuum chamber to prevent or inhibit oxidation of the device. Alternatively, heating may take place in a nitrogen rich environment. A furnace may be used to heat the encapsulated device. Alternatively, or additionally, a mandrel upon which the encapsulated device rests may be used to heat the encapsulated device.

Figure 5A:
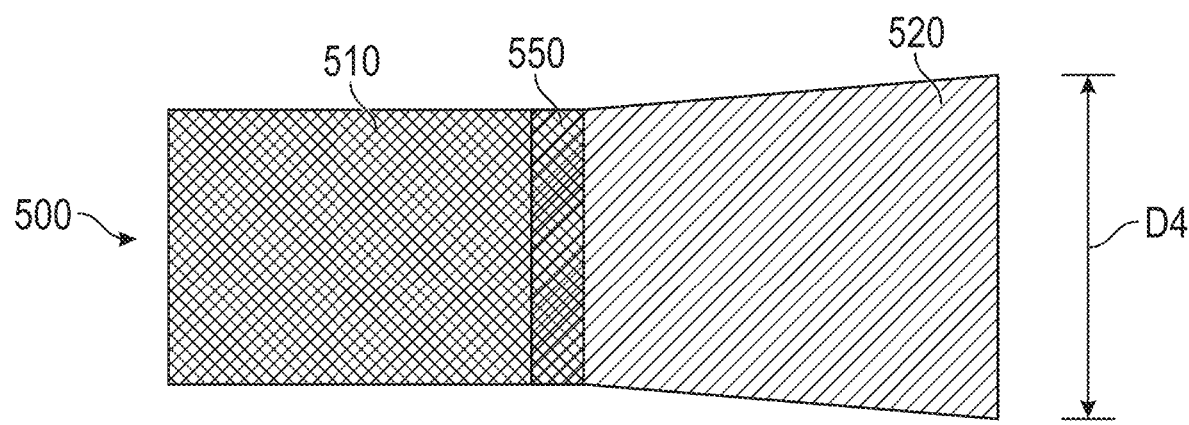
FIGS. 5A-5B schematically illustrate example arrangements of components in a device with an internal dimension that can be reduced and increased in vivo.
Figure 5B:
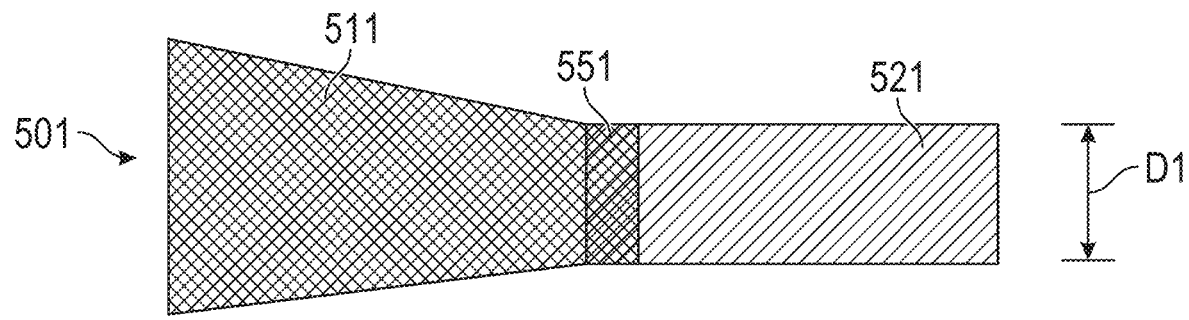

In addition to, or as an alternative to, any other method of joining components of the present device to one another, one or more of the components may be fully or partially inserted into another one or more of the components. For example, FIGS. 5A-5B schematically illustrate example arrangements of components in a device with an internal dimension that can be reduced and increased in vivo. In example device 500 illustrated in FIG. 5A, which may include any suitable number of components (only two components illustrated for simplicity), second component 520 is at least partially located inside of first component 510, which components may be configured similarly as described with reference to FIGS. 1A-1E, 2A-2E, or 3A-3D. Overlap region 550 between first component 510 and second component 520, which region optionally may extend for the entire length of one or both of first component 510 and second component 520, may join the malleable shape-memory material (e.g., of component 520) to the self-expanding superelastic material (e.g., of component 510). For example, the outer surface of second component 520 may engage with (e.g., mechanically interfere with) the inner surface of first component 510 in such a manner as to inhibit lateral motion of the two components relative to one another. Additionally, the dimension of first component 510 may constrain expansion of second component 520 beyond that dimension within overlap region 550, e.g., may apply a force that inhibits second component 520 from fully expanding. As such, even if second component 520 is expanded (e.g., mechanically), the dimension of first component 510 may inhibit the second component from entirely expanding to a larger dimension.

In example device 501 illustrated in FIG. 5B, which may include any suitable number of components (only two components illustrated for simplicity), first component 511 is at least partially located inside of second component 521, which components may be configured similarly as described with reference to FIGS. 1A-1E, 2A-2E, or 3A-3D. Overlap region 551 between first component 511 and second component 521, which region optionally may extend for the entire length of one or both of first component 511 and second component 521, may join the malleable shape-memory material (e.g., of component 521) to the self-expanding superelastic material (e.g., of component 511). For example, the inner surface of second component 521 may engage with (e.g., mechanically interfere with) the outer surface of first component 511 in such a manner as to inhibit lateral motion of the two components relative to one another. Additionally, the dimension of second component 521 may constrain expansion of first component 511 beyond that dimension within overlap region 551, e.g., may apply a force that inhibits first component 511 from fully expanding. As such, even if first component 511 is expanded (e.g., self-expands), the dimension of second component 521 may inhibit the first component from entirely expanding to a larger dimension.

Mechanical interference between components, e.g., such as described with reference to FIGS. 5A-5B, may inhibit recoil of the shape memory component. For example, a known problem with martensitic NITINOL stents is recoil, in which about 10-15% diameter shrinkage may make apposition to a vascular wall challenging. Mechanical interference between device components, e.g., concentric coupling such as illustrated in FIGS. 5A-5B, may reduce or inhibit such recoil. For example, in the configuration described with reference to FIG. 5B, first component 511 may physically inhibit second component 521 from recoiling. In some configurations, the respective hoop strengths of the first and second components may be approximately balanced with one another, optionally with the shape-memory martensitic component being slightly stronger, so as to reduce or minimize recoil.

Figure 6:
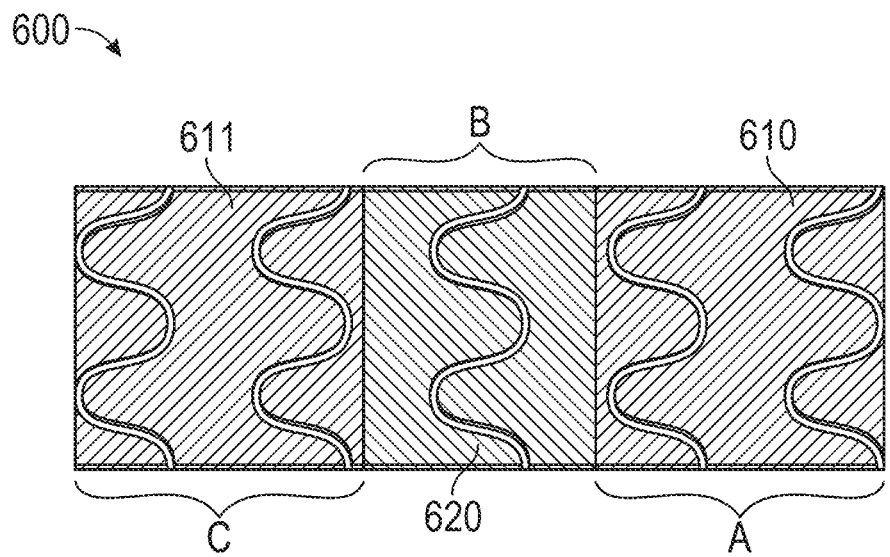
FIG. 6 schematically illustrates another example device with an internal dimension that can be reduced and increased in vivo.

It will be appreciated that devices such as described with reference to FIGS. 1A-1E, 2A-2E, 3A-3D, and options thereof such as described with reference to FIGS. 4A-4B and 5A-5B, may have any suitable configuration. For example, FIG. 6 schematically illustrates another example device 600 with an internal dimension that can be reduced and increased in vivo. Device 600 includes first component 610 (also designated "A"), second component 620 (also designated "B"), and third component 611 (also designated "C"). Device 600 optionally may include a tube of material that is laser-cut to define a plurality of struts and connecting members, e.g., a plurality of sinusoidal rings connected by longitudinally extending struts (struts not specifically illustrated). The sinusoidal rings illustrated in FIG. 6 may be laser cut to form an integral piece of unitary construction, and different regions of the piece may be heat treated differently than one another to produce components having different Afs than one another in a manner such as described elsewhere herein. Alternatively, the sinusoidal rings of first component 610, second component 620, and third component 611 may be separately defined to form different pieces of material with suitable Afs that are subsequently coupled together to form device 600. Device 600 may also be electropolished to reduce thrombogenicity.

Optionally, the Af of first component 610 and the Af of third component 611 each may be greater than the Af of second component 620. For example, first component 610 may correspond to first component 210 described with reference to FIGS. 2A-2E and may include a first self-expanding superelastic material, second component 620 may correspond to second component 220 and may include a malleable shape-memory material, and third component 611 may correspond to third component 211 and may include a second self-expanding superelastic material. As another option, the Af of first component 610 and the Af of third component 611 may be less than the Af of second component 620. For example, first component 610 may correspond to first component 310 described with reference to FIGS. 3A-3D and may include a self-expanding superelastic material, second component 620 may correspond to second component 320 and may include a first malleable shape-memory material, and third component 611 may correspond to third component 321 and may include a second malleable shape-memory material. Optionally, the Af of first component 610 and the Af of third component 611 may be the same as one another.

It will be appreciated that the present devices may be percutaneously implanted within any suitable portion of the human body, such as a body lumen (e.g., a blood vessel) or the heart. Similarly, it will be appreciated that the present devices suitably may be adjusted in vivo, after implantation, in such a manner as to adjust the flow of fluid in such a manner as to treat or ameliorate any suitable condition such as HF, PAH, aneurism, aortic valve stenosis, mitral valve stenosis, or to improve outcomes following cardiac valve repair (e.g., mitral valve repair) or following cardiac ablation (e.g., for treating atrial fibrillation). Some nonlimiting examples of devices for implantation at selected locations are described with reference to FIGS. 7-10C.

In some examples, the present devices may be or include hourglass or "diabolo" shaped shunts, which optionally are encapsulated with biocompatible material, and which may be used for treating subjects suffering from disorders for which regulating fluid flow may be useful, such as CHF or PAH. In some examples, the hourglass shaped shunts may be specifically configured to be lodged securely in the atrial septum, for example in an opening through the fossa ovalis, to allow blood flow from the left atrium to the right when blood pressure in the left atrium exceeds that of the right atrium, or blood flow from the right atrium to the left when blood pressure in the right atrium exceeds that of the left atrium. As provided herein and described in greater detail with reference to FIGS. 7-10C, the internal dimension of the hourglass shaped shunt suitably may be adjusted in vivo, for example, so as to adjust the flow of fluid therethrough, e.g., so as to adjust the flow of fluid between the left atrium and the right atrium through the atrial septum.

Figure 7:
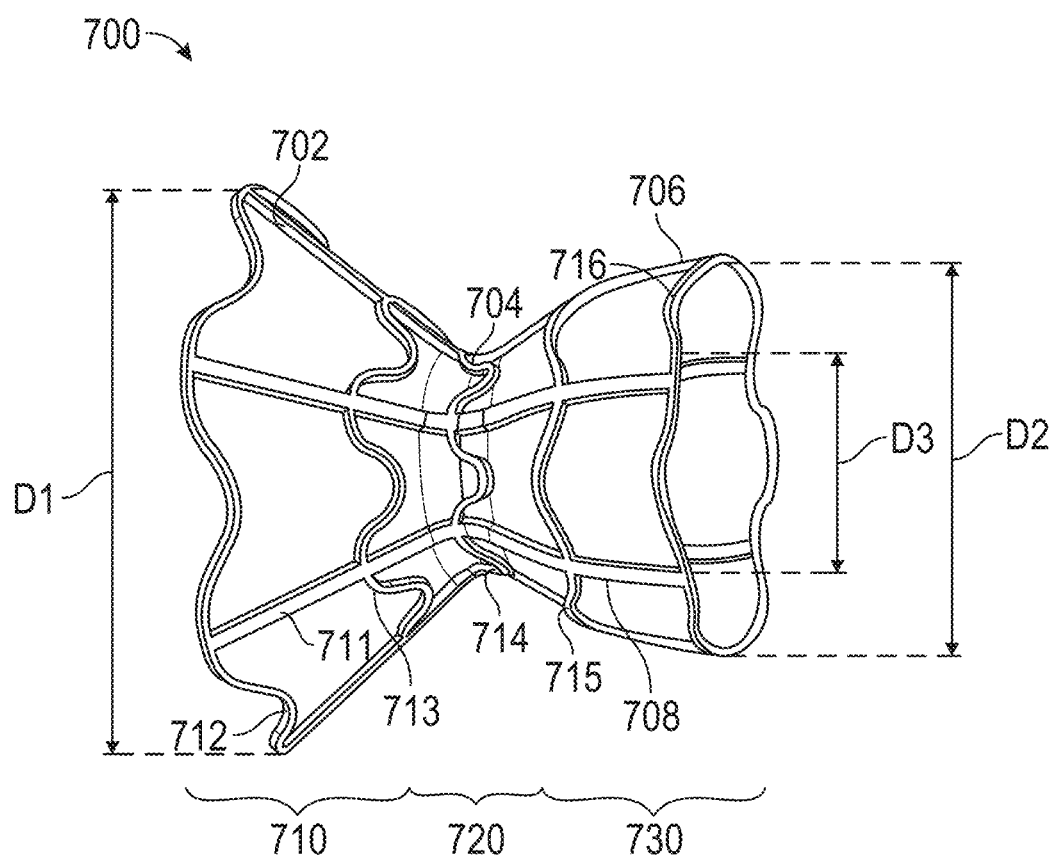
FIG. 7 schematically illustrates another example device with an internal dimension that can be reduced and increased in vivo.

Referring now to FIG. 7, shunt 700 is illustrated that has an internal dimension that can be reduced and increased in vivo. Shunt 700 is hourglass or "diabolo" shaped and may include first component 710, second component 720, and third component 730 which are fluidically coupled to one another. First component 710 may include a first self-expanding superelastic material, second component 720 may include a malleable shape-memory material, and third component 730 may include a second self-expanding superelastic material, in a manner similar to that described with reference to FIGS. 2A-2E. First component 710 may include any suitable number of rings, e.g., rings 712, 713, which are formed of or include the first self-expanding material, and which optionally may be sinusoidal. Second component 720 may include any suitable number of rings, e.g., ring 714, which is formed of or includes the malleable shape-memory material, and which optionally may be sinusoidal. Third component 730 may include any suitable number of rings, e.g., rings 715, 716, which are formed of or include the third self-expanding material, and which optionally may be sinusoidal. Struts 711, 708 may join the rings of first component 710, second component 720, and third component 730 to one another.

First component 710 may provide a first flared end region 702, third component 730 may provide a second end flared region 706, and second component 720 may provide a neck region 704 disposed between the first and second flared end regions. The inlet and outlet of device 700 may include flanges 702, 706, and the neck 704 may include flexible longitudinal bars 711, 708 and a sinusoidal ring 714. The flexible longitudinal bars 711, 708 may allow the flanges to fully expand upon deployment; and the sinusoidal ring may have sufficient strength to maintain its diameter when balloon dilated or heat contracted.

In the nonlimiting example shown in FIG. 7, first flared end region 702 has first end region dimension D1, second flared end region 706 has second end region dimension D2, and neck region 704 has neck dimension D3 which may be increased or reduced in a manner such as described with reference to second component 220 illustrated in FIGS. 2A-2E. As shown in FIG. 7, neck region 704 of shunt 700 may be significantly narrower than flared end regions 702 and 706, e.g., may have a smaller cross sectional area and a smaller dimension than do flared end regions 702 and 706.

Also shown in FIG. 7, shunt 700 may be asymmetric. For example, shunt 700 may be asymmetric to take advantage of the natural features of the atrial septum of the heart as well as the left and right atrium cavities. Alternatively, hourglass shaped shunt 700 may be symmetric with the first end region dimension D1 being equal to the second end region dimension D2. First flared end region 702 and second flared end region 706 also may have either straight or curved profiles or both. For example, strut 711 has a straight profile and strut 708 has a curved profile. Additionally, first flared end region 702 and second flared end region 706 may assume any angular position consistent with the hour-glass configuration.

Shunt 700 suitably may be formed in a manner such as described elsewhere herein. For example, in some configurations, shunt 700 is laser-cut from a single tube of NITINOL in a manner such as described with reference to device 600 illustrated in FIG. 6, and different regions of the NITINOL are heat treated differently than one another so as respectively to define self-expanding superelastic material(s) and malleable shape-memory materials. As such, the first, second, and third components 710, 720, 730 of device 700 optionally may be unitary with one another. The first and third self-expanding materials optionally may be the same material as one another. In other configurations, the first, second, and third components 710, 720, 730 of device 700 may be formed independently of one another and assembled together, e.g., in a manner such as described with reference to FIGS. 5A-5B and as further exemplified with reference to FIGS. 20A-22I, described below.

Figure 8A:
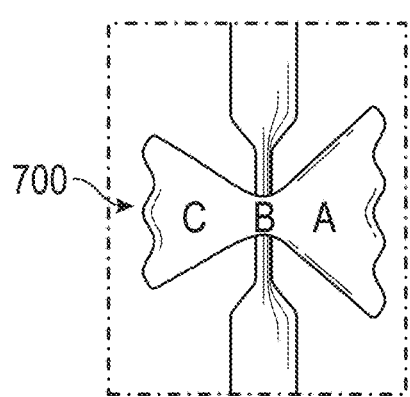
FIGS. 8A-8D schematically illustrate example steps for using the device of FIG. 7 in the human body.

FIGS. 8A-8D schematically illustrate example steps for using the device of FIG. 7 in the human body. Shunt 700 may be crimped to a cylindrical shape, for example by pushing it through a conical loading device. In one nonlimiting example, shunt 700 may be crimped to an outer dimension of about 4.6 mm, the inside dimension of a 14F Cook sheath. The sheath may be percutaneously placed through a blood vessel to a desired location in the human body, and the crimped shunt may be placed in the sheath in a manner similar to that illustrated in FIG. 2A. As the crimped shunt is pushed out of the sheath, the self-expanding superelastic flared end regions spring open to their set configuration, while the malleable shape-memory central neck region remains constrained at or near its crimped dimension, e.g., in a manner such as illustrated in FIG. 8A in which the neck region (designated "B" and corresponding to second component 220) engages an opening in the human body. Depending on the desired direction of blood flow through device 700, one of the flared ends (designated "A" or "C" and corresponding to first component 210 or third component 211) provides an inlet and the other of the flared ends (designated "C" or "A" and corresponding to third component 211 or first component 210) provides an outlet. For example, the neck region may engage an opening created through a fossa ovalis of an interatrial septum between a right atrium and a left atrium, one of the flared ends extends into the right atrium, and the other flared end extends into the left atrium. In some configurations, the flared end in the right atrium is an inlet and the flared end in the left atrium is an outlet, whereas in other configurations, the flared end in the left atrium is an inlet and the flared end in the right atrium is an outlet.

Figure 8B:
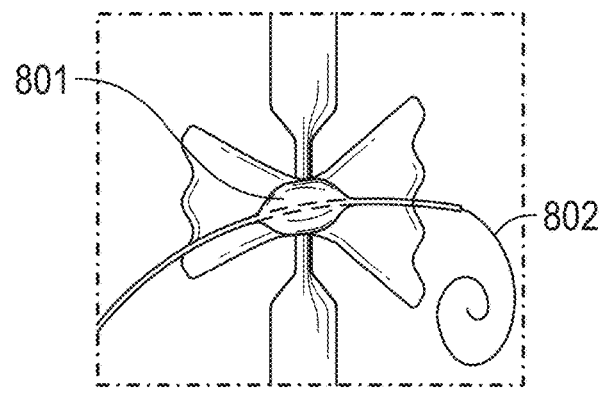
Figure 8C:
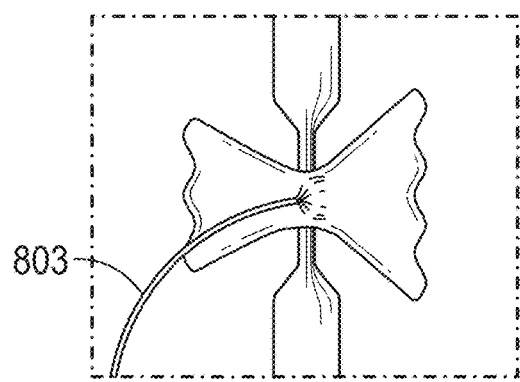
Figure 8D:
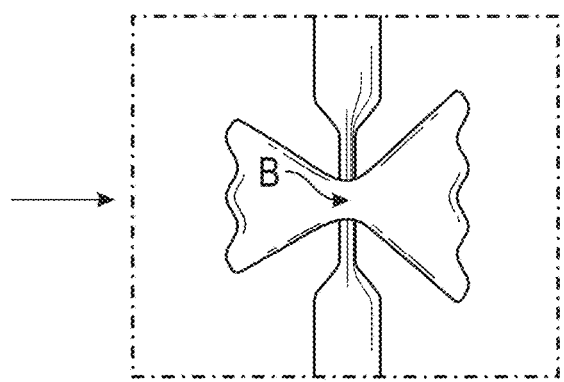

The cross sectional area (and dimension) of the orifice provided by the malleable shape-memory central neck region may be increased or reduced so as to adjust the flow of fluid through shunt 700. For example, in a manner such as illustrated in FIG. 8B, the neck region may be expanded by balloon dilatation using a balloon 801, which may be fed through the orifice using a wire 802. Additionally, in a manner such as illustrated in FIG. 8C, the neck region may be contracted by injecting, via catheter 803, a bolus of hot saline having a temperature above the Af of the malleable shape-memory material (e.g., at 40-60° C.), which may cause the neck region to return to its heat-set dimension, which may be different from its crimped dimension, in a manner such as illustrated in FIG. 8D.

For example, heat from the saline may cause the malleable shape-memory material to transition to an austenitic phase, compressing the neck region back to its crimped (or otherwise heat set) dimension, following which the neck region cools to body temperature and transitions back to its martensitic phase. The saline may be delivered in any suitable manner, for example by a flexible catheter having one or more apertures (e.g., one side hole or multiple side-holes) through which hot saline may flow and that may be placed within the neck region, for example, over a guidewire through the neck region. In one nonlimiting example, the neck region may have its crimped inner dimension, typically 1-2 mm, at a first time, such as when initially deployed in a manner such as illustrated in FIG. 8A. The neck region then may be expanded using balloon dilatation to any desired larger dimension between the crimped dimension and 7 mm at a second time. The neck region then may be contracted using hot saline to its heat-set dimension, D0, at a third time. Dimension D0 is determined by the size of the jig used in a heat-setting step during manufacture. D0 may be greater than the dimension of the catheter used to deliver hot saline, and greater than the deflated dimension of the dilation balloon, but smaller than or equal to the smallest anticipated desired final shunt dimension, for example 4 mm. The neck region then again may be expanded using balloon dilatation to any desired larger dimension between 4 mm and 7 mm at a second time. Any suitable number of expansions and contractions may be applied to the neck region, at any desired time or at separate times than one another, so as to provide a suitable, and customized, flow of fluid through the device for each given patient. It will be appreciated that what constitutes a suitable flow of fluid for a given patient also may change over time, and that the present devices suitably may be adjusted—so as to provide that flow of fluid as appropriate, or so as to suitably fixate the devices within a lumen. It will also be appreciated that the self-expanding superelastic components are not affected by the injection of hot saline, and so will retain their initial full expanded dimension while the shape-memory component (in this example the neck region) is being adjusted. Furthermore, any suitable method for heating the shape memory materials may be used besides or in addition to hot saline, e.g., RF heating or the use of a laser, magnetic inductance, electrical resistance, or the like in a manner such as described with reference to FIGS. 1A-1E.

Figure 9A:
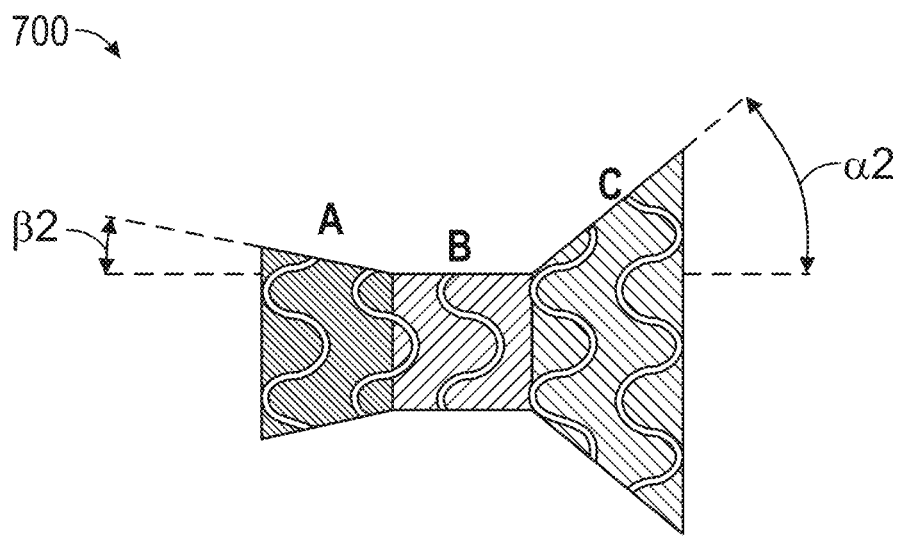
FIGS. 9A-9B schematically illustrate example configurations of the device of FIG. 7.
Figure 9B:
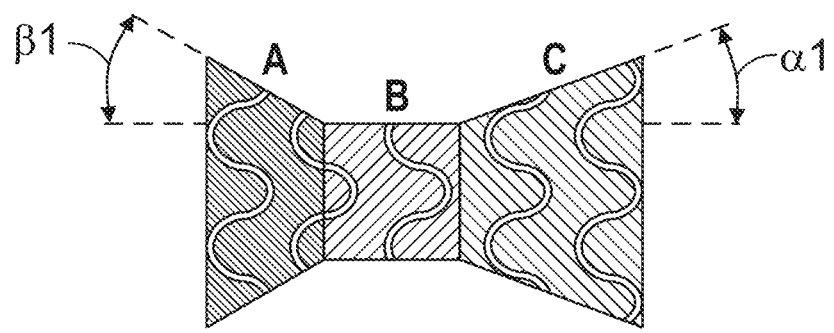

The particular configuration of shunt 700 may be selected so as to provide desired flow dynamics therethrough. For example, FIGS. 9A-9B schematically illustrate example configurations of the device of FIG. 7. In FIGS. 9A-9B, the geometry of the inlet and outlet inner dimensions (e.g., the inlet and outlet angles α and β) may be selected so as to adjust the flow dynamics through shunt 700. Apart from adjusting the flow dynamics so as to treat a specific clinical condition, the capability to narrow the inlet or outlet, or both, may reduce the risk of passage of thrombus into or through the device lumen.

Figure 10A:
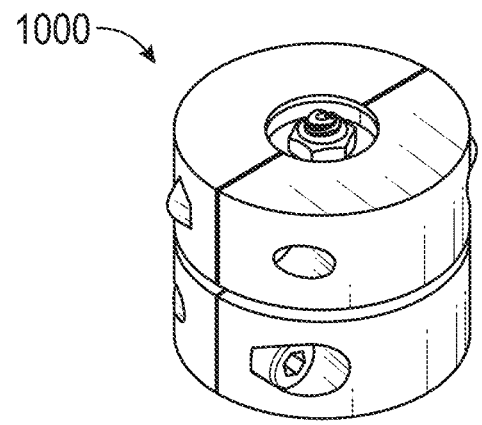
FIGS. 10A-10C schematically illustrate example uses of tooling for preparing the device of FIG. 7.
Figure 10B:
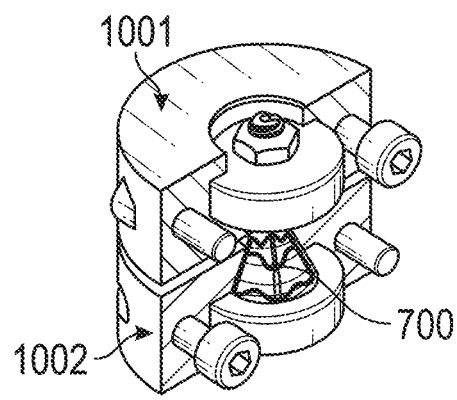
Figure 10C:
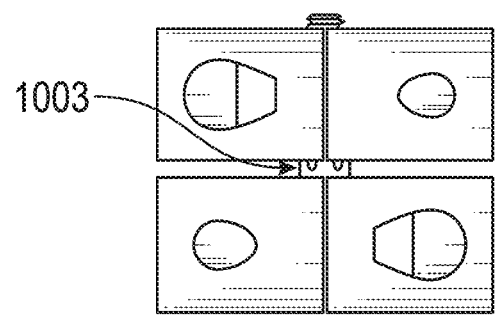

Shunt 700 (or any other device provided herein) may be made using any suitable combination of techniques. FIGS. 10A-10C schematically illustrate example uses of tooling for preparing the device of FIG. 7. As shown in FIGS. 10A-10C, the shunt 700 (or any other device provided herein) may be heat treated within tooling 1000 which allows for the component(s) which are to be substantially self-expanding superelastic material to be maintained at a cooler temperature (e.g., individually insulated or heat-sinked by dies 1001, 1002 within the tooling) than the component(s) which are to be substantially malleable shape-memory material, e.g., which may be exposed such as at region 1003 illustrated in FIG. 10C. As such, the exposed component(s) may receive a greater heat flux during the heat treatment which may result in a predetermined higher Af temperature as compared to component(s) that are insulated or kept cooler by contact with a heat sink. The temperature gradient between the heated and cooled regions may result in a transition zone between a region that is substantially martensitic at body temperature (37° C.) and a region that is substantially austenitic at body temperature. In addition, the transition zone may provide a smooth, continuous transition between the neck region and flared end regions during dilatation or contraction of the neck region. The heat treatment may be implemented by a furnace, induction heating, an electrical current, or any other suitable and controllable energy source. The difference in heat flux (which may result in a higher Af for the component(s) which are to be substantially malleable shape-memory material) also may be achieved by providing that component with a different (lower) wall thickness, e.g., as may be achieved by material removal from a NITINOL tube prior to laser cutting or using an additive manufacturing process to manufacture the device.

It will be appreciated that tooling 1000 is optional, and that any of the devices herein (illustratively, device 200 described with reference to FIGS. 2A-2E; device 700 described with reference to FIGS. 7, 8A-8D, 9A-9B, and 10A-10C; or device 28 described with reference to FIGS. 15A-15E) suitably may be formed using localized heat-treating of one or more portions of each such device to produce a different Af from un-heated portion(s) of the device. Such localized heating of portion(s) of the device may be performed, for example, using induction heating, optionally with active cooling of adjacent areas. Additionally, or alternatively, such localized heating of portion(s) of the device may be performed using localized laser heating, optionally with active cooling of adjacent areas. Furthermore, it is known that the effect of heat treatment on NITINOL Af is cumulative, such that the same effect can be produced by a plurality of short duration heat treatments to a given temperature as by a single longer duration treatment at that temperature. Thus it is contemplated that a series short, intense, localized laser heating pulses, the intensity and duration of each pulse chosen to raise to the area in the laser beam to the desired heat treatment temperature, combined with active cooling, such as by a flow of cold Argon or other suitable gas, may allow highly localized increase of Af while maintaining a lower Af at adjacent areas.

It will further be appreciated that wires of different Af temperatures may be used to prepare the present devices. For example, in a manner such as described in U.S. Pat. No. 10,898,698 to Eigler, wires having different Af temperatures than one another, and/or wires having different Af temperatures along the length of the wire, may be used to prepare the present devices. Such wires may be used to manufacture devices having multiple Af temperatures (e.g., multiple phases of NITINOL), illustratively using wire-wrap techniques, wire-mesh techniques, or any suitable combination thereof.

It will further be appreciated that any suitable combination of superelastic and shape memory NITINOL components may be used within the present devices.

Additionally, or alternatively, shunt 700 (or any other device provided herein) may be made using a multi-material additive manufacturing process. For example, the higher Af component(s) which are to be malleable shape-memory material may be provided by using selective laser melting or an electron beam melting powder bed machine which has two or more powder-bins between which the machine could switch during the print process. The Af of a given component may be manipulated by the powder's chemical composition, e.g., different fractions of nickel titanium or of any other element(s) that may be present. For example, the higher the nickel percentage, the higher the Af. The Af of a given component also or alternatively may be manipulated by the powder's physical composition, e.g., particle sizes. For example, the smaller the powder dimension, the lower the Af. For further details of manipulating the Af of materials during a multi-material additive manufacturing process, see Horvay and Schade, "Development of nitinol alloys for additive manufacturing," the entire contents of which are incorporated by reference herein. As another option, the multi-material may be achieved by liquid dispersion methodology (material jetting). For example, a 3-D printer may include two or more cartridges with different powder-liquid compositions in each, in a manner similar to that described for the powder-based example.

Figure 11:
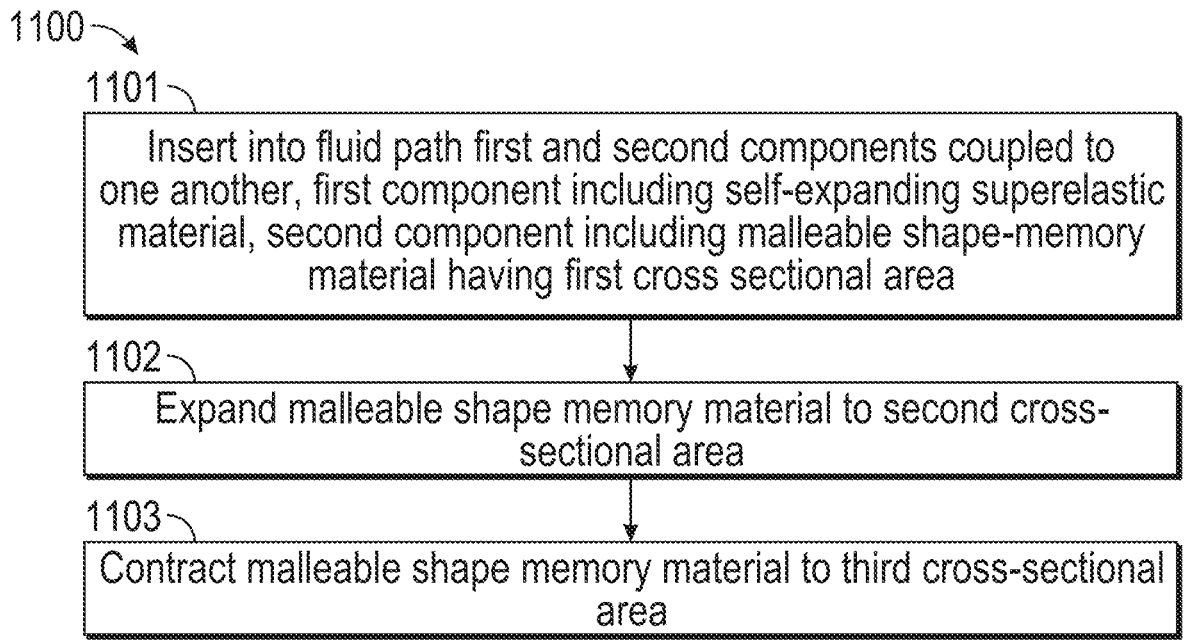
FIG. 11 illustrates a flow of operations in an example method for reducing and increasing an internal dimension of a device in vivo.

It will be appreciated that any of the devices provided herein, not necessarily limited to the particularly illustrated examples, may be used in a method for adjustably regulating fluid flow. For example, FIG. 11 illustrates a flow of operations in an example method 1100 for reducing and increasing dimension of a device in vivo. Method 1100 may include inserting into a fluid path first and second components coupled to one another (1101). The first component may include a self-expanding superelastic material, and the second component may include a malleable shape-memory material having a first cross sectional area. Nonlimiting examples of such first components and second components, and optional configurations thereof, are described with reference to FIGS. 1A-1E, 2A-2E, 3A-3D, 4A-4B, 5A-5B, 6, 7, 8A-8D, 9A-9B, 15A-15E, 17A-17E, 20A-20F, and 21A-22I.

Method 1100 illustrated in FIG. 11 also may include expanding the malleable shape-memory material to a second cross sectional area (operation 1102). For example, as described elsewhere herein, the malleable shape-memory material may be expanded using balloon dilatation.

Method 1100 illustrated in FIG. 11 contracting the malleable shape-memory material to a third cross sectional area (operation 1103). For example, as described elsewhere herein, the malleable shape-memory material may be contracted using heat, for example as applied using saline heated to above Af of the shape-memory material, or using another suitable energy source such as radio frequency electrical current (RF).

Accordingly, in examples provided herein, a fluid flow path through an implantable device may be both increased and reduced following implantation, allowing for repositioning of the device or a customized fluid flow that is appropriate to the particular patient's needs. In comparison, for previously known devices repositioning may not be possible, and the size of the fluid flow path either is selected prior to implantation or may be increased using balloon dilatation, providing limited options for achieving a desired hemodynamic result in a patient. In examples such as provided herein, the component(s) including self-expanding superelastic material(s) may assume their shape immediately upon implantation within the body, which may inhibit device migration and ensure accurate positioning. The component(s) including malleable shape-memory material(s) may be plastically deformable (e.g., expandable) at body temperature and may be returned to a heat-set dimension upon application of heat. The heat-set dimension of a malleable shape-memory component optionally may be larger than a crimped dimension of the component. Accordingly, in some examples a malleable shape-memory component may be expanded by suitably applying heat, e.g., as an alternative to an initial balloon dilatation after delivery of the crimped device. The malleable shape-memory component(s) repeatedly may be expanded and contracted, which may allow for adjustment of fluid flow through the device, or for the device to be repositioned, or a combination of such features.

For example, certain of the devices provided herein may be repositionable for fixation within a body lumen. As described above, the devices may include a first component including a self-expanding superelastic material, and a second component coupled to the first component and comprising a malleable shape-memory material, in a manner such as described with reference to FIGS. 1A-1E, 2A-2E, 3A-3D, 4A-4B, 5A-5B, 6, 7, 8A-8D, 9A-9B, 11A-11B, 15A-15E, 17A-17E, 20A-20F, and 21A-22I. The self-expanding superelastic material may have a predetermined fully expanded dimension (e.g., that may be heat set during manufacture). The second component may have a first dimension suitable for deployment through a catheter (e.g., may be crimped to that dimension). The malleable shape-memory material may be expandable to a second dimension for fixation within a body lumen (e.g., via balloon dilatation), and may be thermally transitionable to a third dimension (e.g., via application of heat within the body as described elsewhere herein). The malleable shape-memory material may be mechanically re-expandable to a fourth dimension (e.g., via balloon dilatation).

Figure 12:
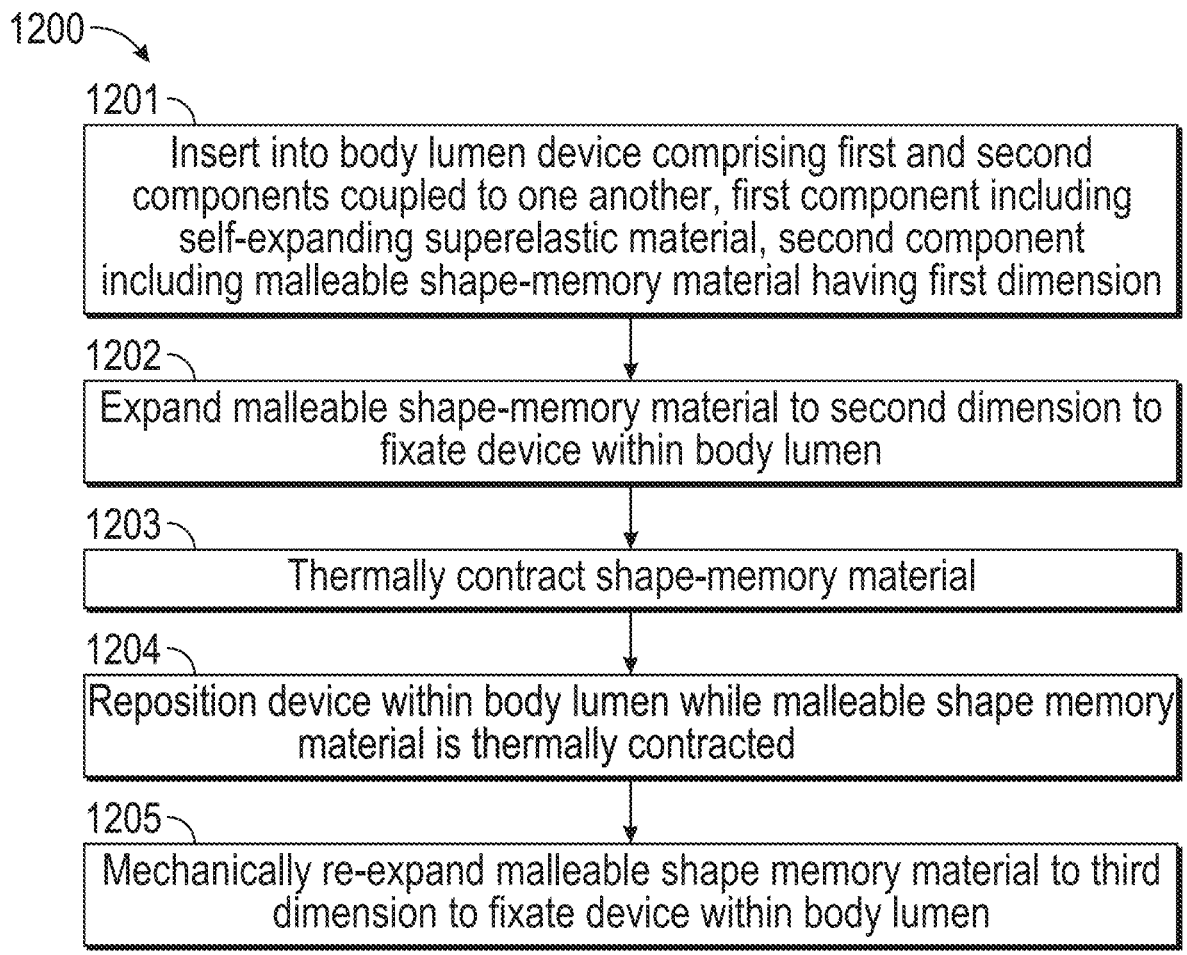
FIG. 12 illustrates a flow of operations in an example method for fixating a device in a body lumen.

Accordingly, it will be appreciated that certain of the devices provided herein, not necessarily limited to the particularly illustrated examples, may be used in a method for adjustably fixating a device within a body lumen. For example, FIG. 12 illustrates a flow of operations in an example method 1200 for repositioning a device. Method 1200 includes inserting into a body lumen a device comprising first and second components coupled to one another (operation 1201). The first component may include a self-expanding superelastic material, and the second component may include a malleable shape-memory material having a first dimension, in a manner such as described with reference to FIGS. 1A-1E, 2A-2E, 3A-3D, 4A-4B, 5A-5B, 6, 7, 8A-8D, 9A-9B, 11A-11B, 15A-15E, 17A-17E, 20A-20F, and 21A-22I.

Method 1200 also includes expanding the malleable shape-memory material to a second dimension to fixate the device within a body lumen (operation 1202), for example via balloon dilatation. Method 1200 also includes thermally contracting the malleable shape-memory material (operation 1203), for example via application of heat. Method 1200 also includes repositioning the device within the body lumen while the malleable shape-memory material is thermally contracted (operation 1204), for example by moving the device along a guidewire. Method 1200 also includes mechanically re-expanding the malleable shape-memory material to a third dimension to fixate the device within the body lumen (operation 1205), for example via balloon dilatation.

Although certain examples provided herein relate to permanently implantable devices for use in the human body, it should be appreciated that other examples relate to devices that are used only temporarily in the human body. Additionally, although certain examples herein primarily relate to changing the internal dimension of a device, it should be appreciated that other examples primarily relate to changing the external dimension of a device. For example, FIGS. 13A-13D schematically illustrate an example dilator device 1300 with an external dimension that can be reduced and increased in vivo. Device 1300 may be used, for example, in a "sheathless" method for delivering a permanently implantable device to a suitable location in the human body using an over-the-wire (OTW) approach, e.g., in a manner such as described with reference to FIGS. 14A-14I.

Figure 13A:
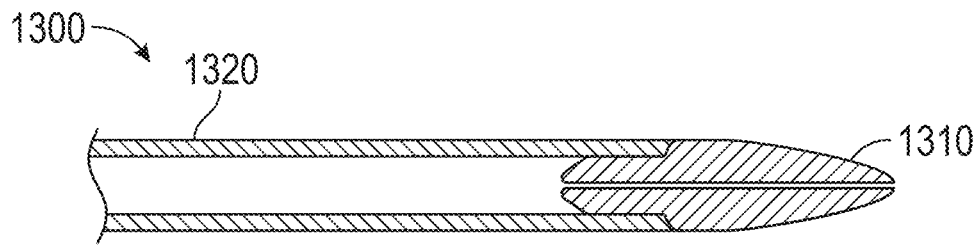
FIGS. 13A-13D schematically illustrate an example dilator device with an external dimension that can be reduced and increased in vivo.
Figure 13B:
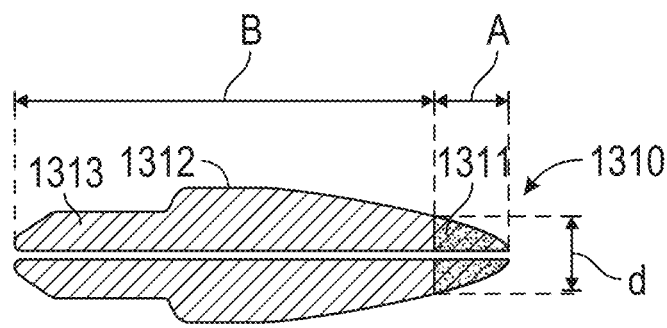

In the example shown in FIG. 13A, device 1300 may include dilator 1310 disposed at the distal end of sheath 1320. As shown in greater detail in FIG. 13B, dilator 1310 may include tip 1311, enlarged region 1312, and reduced region 1313. Reduced region 1313 may be sized so as to securably engage with the distal end of sheath 1320, and enlarged region 1312 may be sized so as to provide device 1300 with a smooth profile between sheath 1320 and tip 1311. Tip 1310 may have an outer dimension d where tip 1311 meets enlarged region 1312, and its distal end may taper to approximately a point. In the example configuration shown in FIG. 13B, dilator 1310 includes a martensitic shape-memory material defining enlarged region 1312 and reduced region 1313 (together, denoted region B), and a self-expanding superelastic material defining tip 1311 (denoted region A). The austenitic finish temperature (Af) of the self-expanding superelastic material may be less than body temperature (which is about 37° C.), e.g., may be in the range of 5-20° C., or 5-15° C. The Af of the martensitic shape memory material may be substantially greater than 37° C., e.g., may be about 40-60° C., e.g., 45-60° C. or about 50° C. Tip 1310, reduced region 1313, and enlarged region 1312 optionally are integrally formed from a common frame with one another.

Figure 13C:
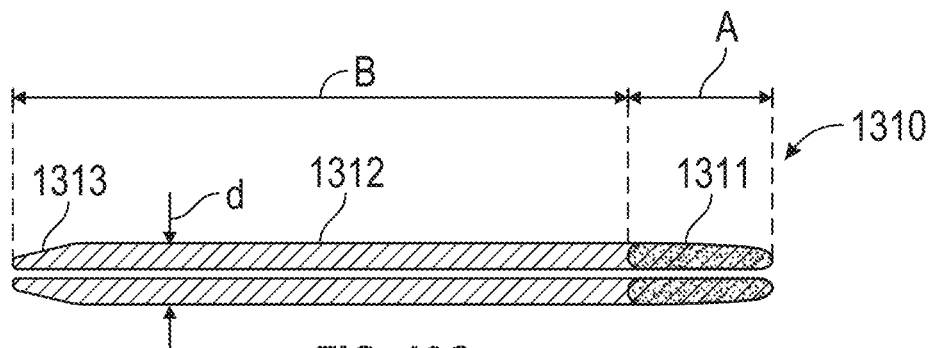
Figure 13D:
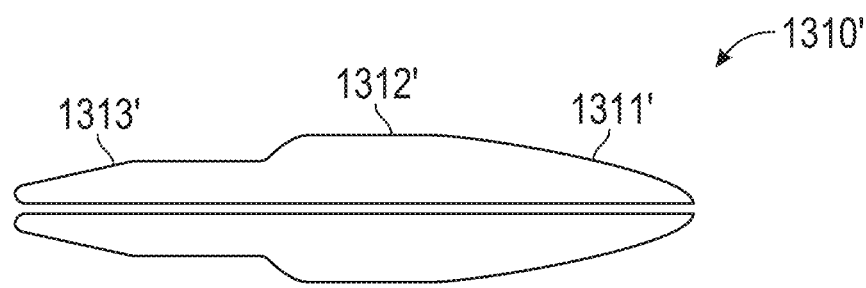

As shown in FIG. 13C, upon application of heat (e.g., using hot saline or RF energy or the use of a laser, magnetic inductance, electrical resistance, or the like) the shape memory material of region B (corresponding to enlarged region 1312 and reduced region 1313) may return to a smaller, heat-set outer dimension that optionally may be approximately equal to d so that the dilator 1310 has a substantially smooth, reduced size profile. In the alternative configuration shown in FIG. 13D, dilator 1310' includes a martensitic shape-memory material defining tip 1311, enlarged region 1312, and reduced region 1313, which may be configured to return to a smaller, heat-set dimension that optionally may be approximately equal to d so that the dilator 1310 has a substantially smooth, reduced size profile.

Figure 14B:
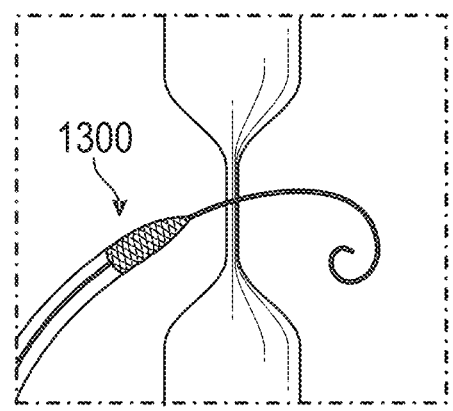
Figure 14C:
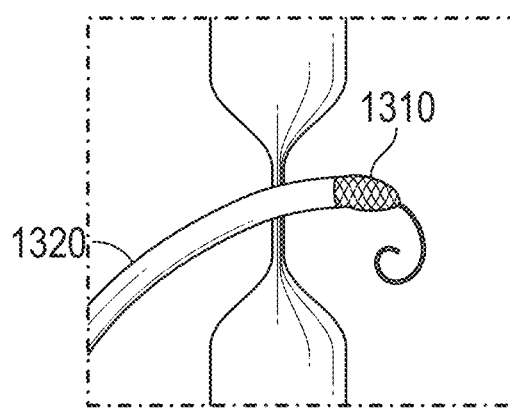
Figure 14D:
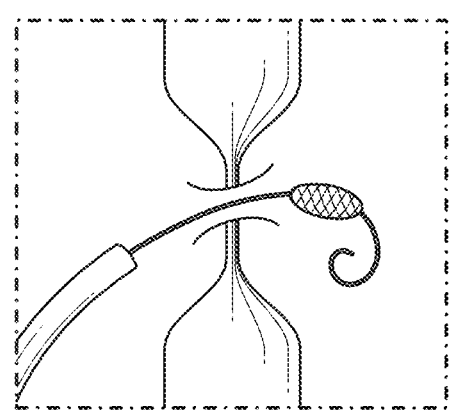
Figure 14E:
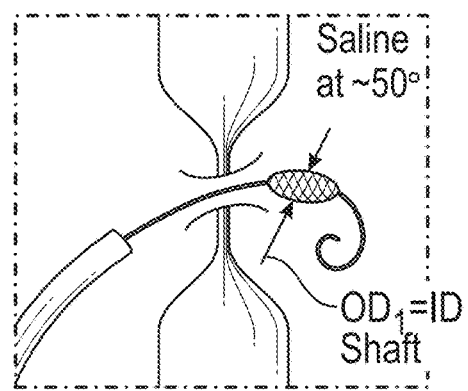
Figure 14F:
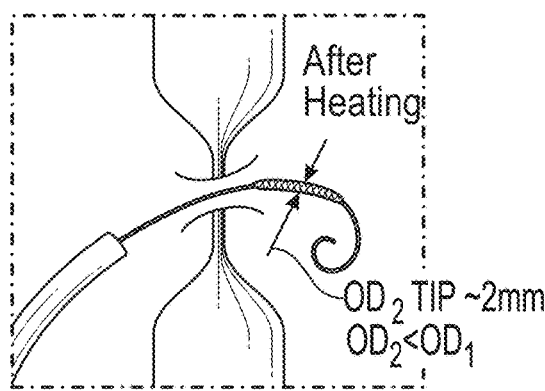
Figure 14G:
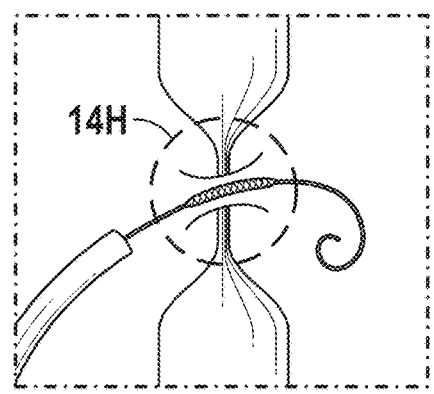
Figure 14H:
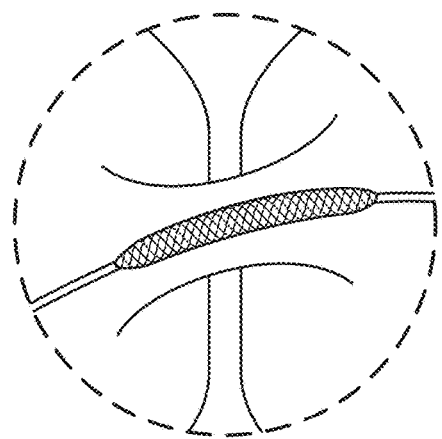
Figure 14I:
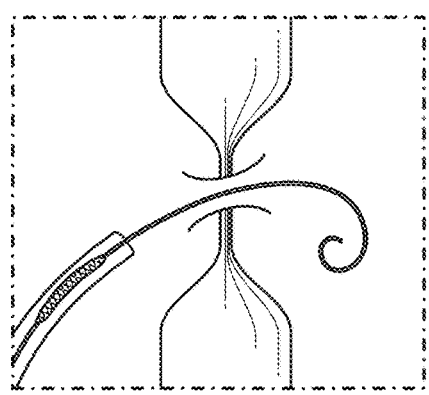

FIGS. 14A-14I schematically illustrate use of the delivery device 1300 of FIGS. 13A-13D in the human body. In the nonlimiting example shown in FIG. 14A, guidewire 1420 is percutaneously placed across a region of the body to be dilated, for example, fossa ovalis 1410 of interatrial septum 1400, creating a small opening having approximately the dimension of guidewire 1420. Device 1300 then is advanced over guidewire 1420 to a position adjacent to fossa ovalis 1410 in a manner such as illustrated in FIG. 14B. As shown in FIG. 14C, pushing on the proximal end of sheath 1320 forces dilator 1310 through fossa ovalis 1410, enlarging the opening to approximately the outer dimension of enlarged region 1312. As shown in FIG. 14D, sheath 1320 may be retracted relative to dilator 1310, leaving dilator 1310 in place on the distal side of fossa ovalis 1410. So as to inhibit harming the tissue of interatrial septum 1400 when retracting dilator 1310, e.g., by catching tissue with enlarged region 1312 when retracting dilator 1310, and so as to inhibit dilator 1310 from catching or becoming entangled with an expandable device that may be delivered across the septum in a manner such as described below, heat may be applied to dilator 1310 on the distal side of fossa ovalis 1410 as shown in FIG. 14E, for example by applying hot saline or RF energy or the use of a laser, magnetic inductance, electrical resistance, or the like at a temperature above the Af of the shape memory material of the dilator. Such heat causes the outer dimension of the enlarged region 1312 to return to its heat-set size. As shown in FIG. 14G and its inset 14H, the reduced-size dilator 1310 may be safely withdrawn through the enlarged opening, and then may be stowed inside of sheath 1320 in a manner such as illustrated in FIG. 14I and subsequently withdrawn from the body. Note that any suitable one of the adjustable devices described elsewhere herein, such as device 700, 1100, 1300, or 2100 may be delivered using delivery device 1300. For example, the adjustable device may be disposed within sheath 1320 and advanced to partially cross the atrial septum together with delivery device 1300 in a manner such as shown in FIG. 14C. Retracting sheath 1320 in a manner such as shown in FIG. 14D deploys the distal shunt flange of the adjustable device in the left atrium, followed by pulling the sheath back to the septal wall, releasing the retention hooks, and pulling the sheath further back such that the septum drags the remainder of the shunt out of the sheath, allowing the proximal flange of the shunt to self-expand in the right atrium. The dimension of dilator 1310 then may be adjusted in vivo and withdrawn through the adjustable device, thus providing a "sheathless" implantation procedure with a relatively low crossing profile and a relatively short procedure time.

Figure 15A:
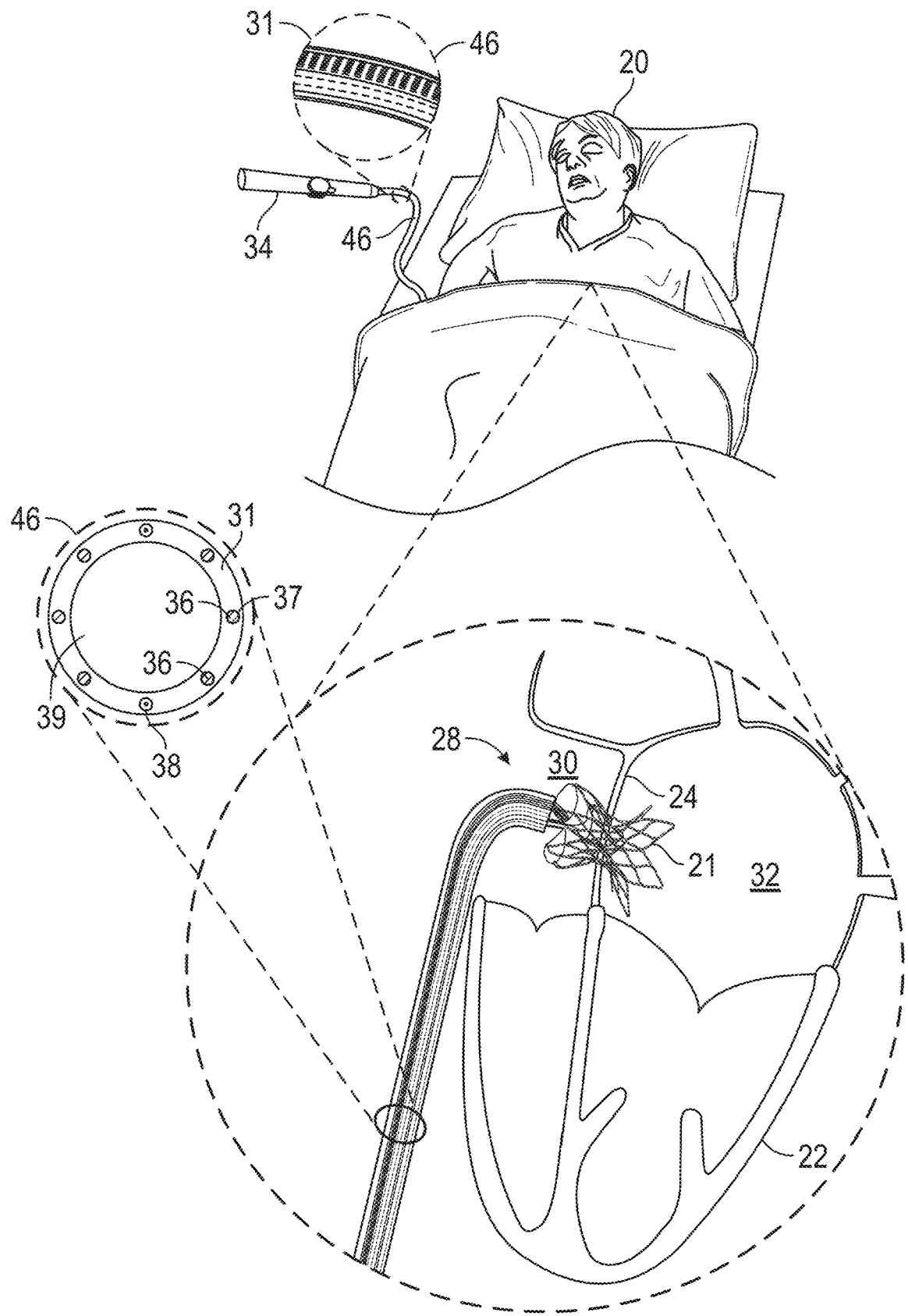
FIGS. 15A-15E schematically illustrate another example device with an internal dimension that can be reduced and increased in vivo, and an example of its temporary use in the human body.
Figure 15B:
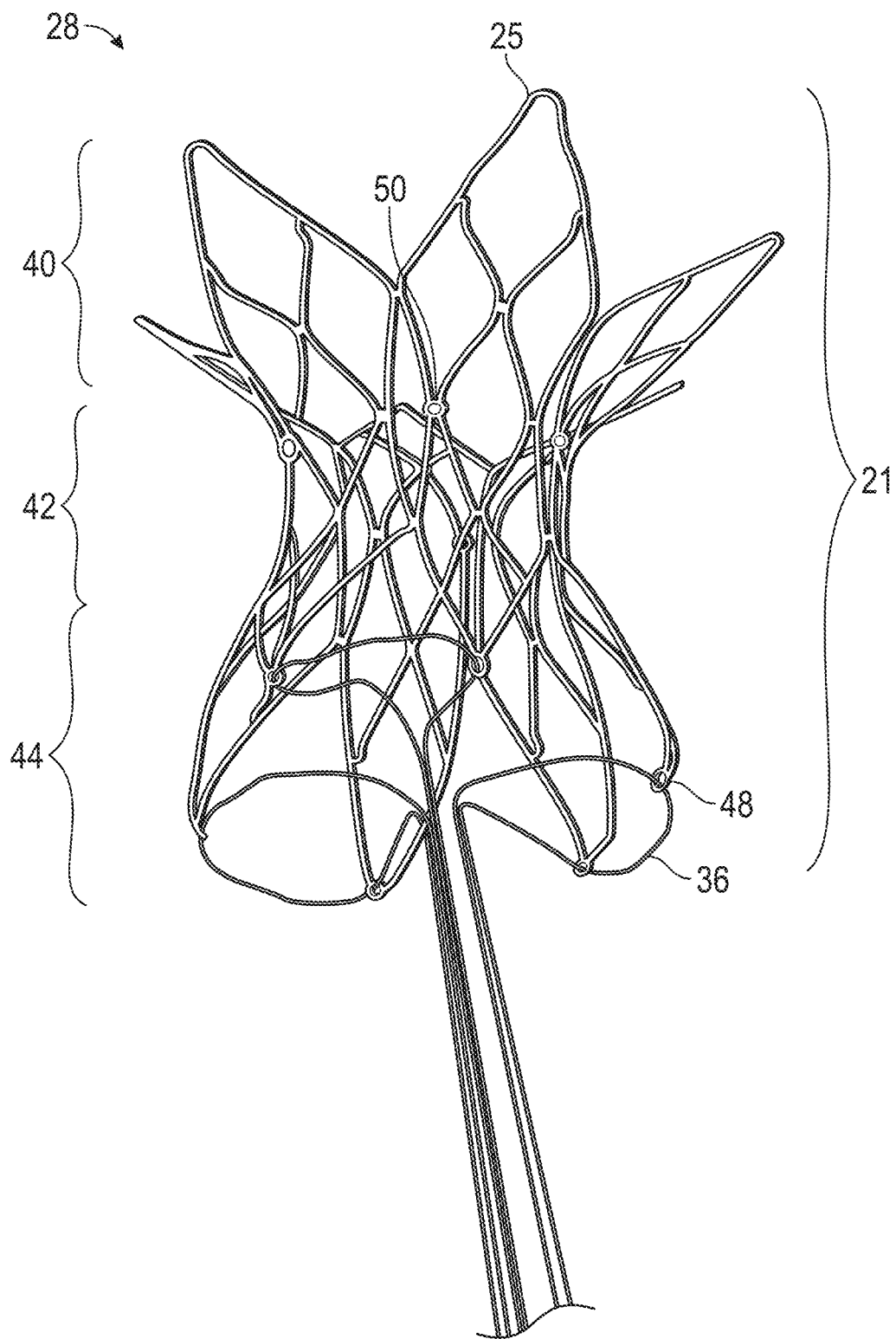

As noted above, the present devices may be permanently or temporarily implanted in the body. In a temporary implantation, the device may be configured for easy removal and may have a dimension that is adjustable in a manner such as described elsewhere herein, or may be permanently connected to the end of a catheter. For example, FIGS. 15A-15E schematically illustrate an example device with an internal dimension that can be reduced and increased in vivo, and an example of its temporary use in the human body. More specifically, FIG. 15A is a schematic illustration of a temporary apparatus 28 inside a subject 20, FIG. 15B is a schematic illustration of temporary apparatus 28, in accordance with some examples provided herein, and FIGS. 15C-15E collectively show a technique for removing temporary apparatus 28 from a subject, in accordance with some examples provided herein.

Apparatus 28 includes device 21, which may be configured similarly as device 200 described with reference to FIGS. 2A-2B or device 700 described with reference to FIG. 7, and which may be placed between two chambers of the heart 22 of subject 20, such as within the interatrial septum 24 of heart 22, between the right atrium 30 and the left atrium 32. Alternatively, the device 21 may be placed between the two ventricles of the heart, or between any other two body cavities. In the example illustrated in FIG. 15B, device 21 includes a flared distal portion 40, a flared proximal portion 44, and an intermediate portion 42, which is disposed between distal portion 40 and proximal portion 44. Distal portion 40 and proximal portion 44 anchor the device 21 to septum 24 (i.e., prevent migration of the device from within the septum), while intermediate portion 42 provides a passageway across the septum, through which blood may flow. In a manner similar to that described with reference to FIGS. 2A-2B and FIG. 7, flared distal portion 40 (first component) may include a first self-expanding material, intermediate portion 42 (second component) may include a malleable shape-memory material, and proximal portion 44 (third component) may include a second self-expanding material. Proximal portion 44, distal portion 40, and intermediate 42 portion optionally are integrally formed from a common frame with one another. The flared distal and proximal portions 40, 44 (first and third components) of device 21 expand to their natural shapes (the shapes shown in FIGS. 15A-15B) upon being released from a delivery sheath 46, while the intermediate portion 42 (second component) provides a cross sectional area that may be increased and reduced in vivo in a manner such as further described below. It is noted that, for clarity, apparatus 28 is drawn disproportionately large, relative to heart 22, in FIG. 15A. The proximal and distal portions 40, 44 of device 21 may be "flared," in that these portions extend radially outward at an acute angle from the axis of the intermediate portion of the stent. In some examples, as shown, each of the proximal and distal portions of the device 40, 44 includes a plurality of leaves 25, such as, for example, six leaves 25, as shown. In other examples, the proximal portion and/or the distal portion does not include a plurality of leaves, but rather, is shaped to define a flared ring, or has some other suitable form.

To facilitate removal of device 21 from the subject in a manner such as described further below with reference to FIGS. 15C-15E, some examples include one or more device-collapsing flexible longitudinal elements 36, which extend from proximal portion 44 to the exterior of the subject. For example, as shown in FIGS. 15A-15B, the device-collapsing flexible longitudinal elements may include control wires 36. In some examples, while inside the subject, wires 36 are contained within control wire lumens 37 of a delivery catheter 31 passing between proximal portion 44 and the exterior of the subject. For example, delivery catheter 31 may exit the subject via a femoral vein of the subject. As shown in FIG. 15A, the proximal ends of control wires 36 may be coupled to control handle 34, via which wires 36 may be pulled (or alternatively, released, such as to allow the proximal portion of the device to expand). Wires 36 may remain coupled to the device 21 throughout the time that the device is in place inside the subject. Due to wires 36 remaining coupled to device 21, the device may be easily removed at any desired time (e.g., immediately) upon receiving indication that further shunting is no longer required through the device, e.g., in a manner such as described with reference to FIGS. 15C-15E. FIG. 15B shows a particular example in which proximal portion 44 is shaped to define a plurality of orifices 48, and each of control wires 36 passes through at least two of orifices 48. For example, as shown, the end of each leaf 25 may be shaped to define an orifice 48, and each wire may pass through the respective orifices of two adjacent leaves, such that the wire forms a loop that passes through the orifices. (Thus, in the illustrated example, device having six proximal leaves is coupled to three wires 36, each wire separately controlling the collapse of a respective pair of adjacent leaves.) To collapse the proximal portion of device 21, the two proximal ends of each of the wires may be pulled.

Alternatively to the example shown, a single wire 36 may form a loop that passes through all of the orifices 48, this single wire controlling the collapse of the entire proximal portion 44. In other words, by pulling on the two ends of this single wire, the entire proximal portion may be collapsed. In yet other examples, wires 36 do not form loops; rather, a separate wire is coupled to each leaf. For example, each leaf may be coupled to the distal end of a respective wire. Thus, for example, a device having six proximal leaves is coupled to six wires, one wire per leaf. Similarly, wires 36 may be formed as extensions of the leaves, such that each leaf has a wire extension that extends to the exterior of the subject. In such examples, the proximal portion of the device may be collapsed by pulling on the single proximal end of each of the wires.

In some cases, it may be beneficial to increase or reduce the cross sectional area of intermediate portion 42 while device 21 is inside the subject, e.g., in a manner such as described elsewhere herein. To allow the cross sectional area of intermediate portion 42 to be increased, delivery catheter 31 may include an enlarged central multipurpose lumen 39 through which an angioplasty balloon or other suitable balloon may be passed over a guidewire and inflated in a manner such as described elsewhere herein. To reduce the cross sectional area of intermediate portion 42, a catheter with one or more holes may be used to inject hot saline within device 21, in a manner such as described elsewhere herein, to heat intermediate portion 42. In some examples, the catheter with one or more holes is passed over a guidewire within delivery catheter 31. In other examples, the catheter with one or more holes is not passed over the guidewire but is introduced to device 21 separately from the guidewire through multipurpose lumen 39 of delivery catheter 31. It will be appreciated that to increase and reduce the cross sectional area of intermediate portion 42, e.g., to provide an appropriate flow rate through device 21 or to reposition device 21, processes of balloon expansion and heating may be repeated any suitable number of times.

In some examples, the adjustment of the cross sectional area of intermediate portion 42 of device 21 is based on pressure monitoring. For example, pressure sensors disposed on the device 21 may be used to acquire intra-atrial pressure measurements. A signal indicative of such pressure measurements may be transmitted outside the body via conductors 38 (also referred to as signal wires), shown schematically in FIG. 15A. The cross sectional area of intermediate portion 42 may be adjusted in response to such measurements. Alternatively, or additionally, the cross sectional area of intermediate portion 42 may be adjusted in response to hemodynamic monitoring, such as by the application of flow imaging techniques such as pulsed wave (PW) or continuous wave (CW) Doppler echocardiography.

In some examples, to place the device 21 within the septum, the device is first collapsed and placed inside a delivery sheath 46 that has been inserted percutaneously into the vasculature of the subject, such as via a femoral vein of the subject, and is then passed through the vasculature into right atrium 30, e.g., via the inferior vena cava. (Alternatively, sheath 46 may be passed into the right atrium via the jugular vein and superior vena cava.) Subsequently, the distal end of the sheath is passed through the septum and into left atrium 32. Prior to passing the distal end of the sheath through the septum, a puncturing element may be used to create an opening in the septum, and, optionally, a dilator may be used to enlarge the opening, such that the distal end of the sheath may easily pass through the septum; in some examples, the dilator is configured and used in a manner such as described with reference to FIGS. 13A-14I. Once the sheath is across the septum, the dilator is removed and the device 21, connected to catheter 31, is collapsed and placed into the proximal end of the delivery sheath 46, and the catheter 31 is used to push the device 21 through the delivery sheath until the distal flared portion 40 of the device is pushed from the distal end of the sheath and allowed to expand to its deployed shape. Sheath 46 is then slowly withdrawn from the septum until the distal flared portion of device 21 engages the left atrial side of the septum. Continued withdrawal of the sheath causes the device 21 to be dragged out of the sheath by the septum, until the proximal flared portion 44 is released, allowing it to expand to its deployed shape on the right atrial side of the septum, as shown in FIG. 15A. The expanded distal and proximal flared portions, 40 and 44, thereby securely anchor the device 21 across the interatrial septum. Intermediate portion 42 (second component) initially may remain in its crimped or compressed configuration having a first cross sectional area, and may be suitably expanded to a second cross sectional area using a balloon which is passed over a guidewire through lumen 39 of catheter 31. The cross sectional area of intermediate portion 42 subsequently may be increased and reduced in vivo in a manner such as described elsewhere herein.

Following the deployment of device 21, sheath 46 and catheter 31 may remain within the subject while device 21 is in place. For example, sheath 46 and catheter 31 may remain within the subject such that the distal end of the catheter is near the proximal portion of the device. The catheter may thus be used to deliver medication to the device site, pressure sensors in the catheter may be used to monitor the intra-atrial pressure, balloons may be introduced within device 21 to increase the cross sectional area of intermediate portion 42, or catheters with one or more holes may be introduced within device 21 to reduce the cross sectional area of intermediate portion 42. By way of example, FIG. 15A shows catheter 31 coupled to a control handle 34, such that control handle 34 may be used to advance and withdraw the catheter through sheath 46.

Device 21 helps relieve excess intra-atrial pressure, by allowing blood to flow from the higher-pressure atrium to the lower-pressure atrium, with a flow rate that may be increased or reduced based on the needs of the particular patient. Device 21 may thus be used as a temporary acute treatment of any relevant condition (e.g., pulmonary hypertension or congestive heart failure) for which the relief of excess pressure is beneficial, or, for example, to help prevent left ventricular dilation and remodeling following an acute myocardial insult. When device 21 is used as an acute treatment, the subject remains hospitalized until the subject's physician decides that sufficient treatment has been provided, at which point device 21 is removed from the subject in a manner such as described with reference to FIGS. 15C-15E, and the subject is released from hospital as appropriate. In some examples, device apparatus 28 includes one or more pressure sensors, disposed, for example, on device 21, on any of the longitudinal elements, or in catheter 31. Such pressure sensors may be used to measure (e.g., continuously) the pressure in the subject's right atrium and/or left atrium, in order to monitor progression of the treatment, to determine whether and by how much the cross sectional area of intermediate portion 42 should be adjusted, and ascertain the point in time at which the device may be removed from the subject. For example, one pressure sensor may be disposed on the proximal portion 40 of device 21, and another pressure sensor on the distal portion 44 of the device, such that the pressure in both the left atrium and the right atrium is measured.

In another embodiment, device 21 is used as temporary measurement device to determine the optimal size for a permanently implanted shunt to be subsequently implanted. In this embodiment, the cross sectional area of intermediate portion 42 of device 21 is adjusted while monitoring pressures and/or other physiological parameters as described for the acute treatment embodiment described above. Once the optimum cross sectional area has been determined, device 21 is removed from the subject in a manner such as described with reference to FIGS. 15C-15E, and a permanent shunt of the indicated size is implanted.

Figure 15C:
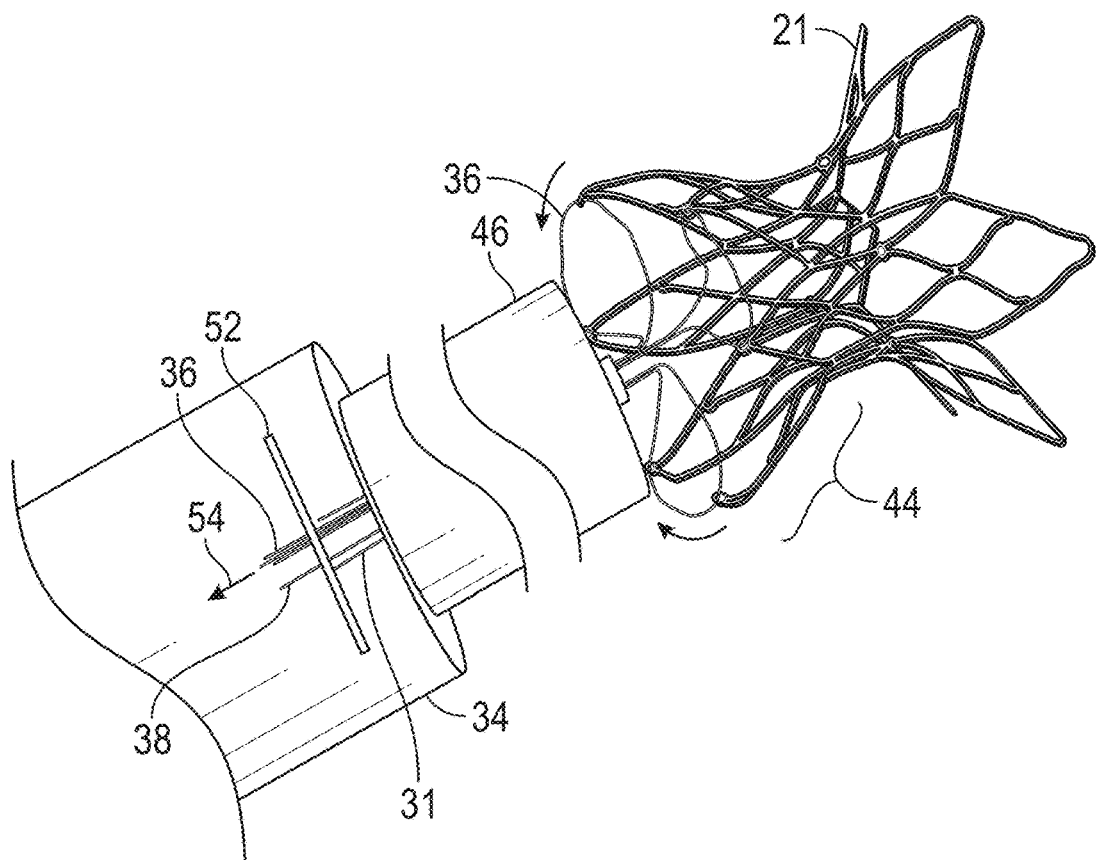
Figure 15D:
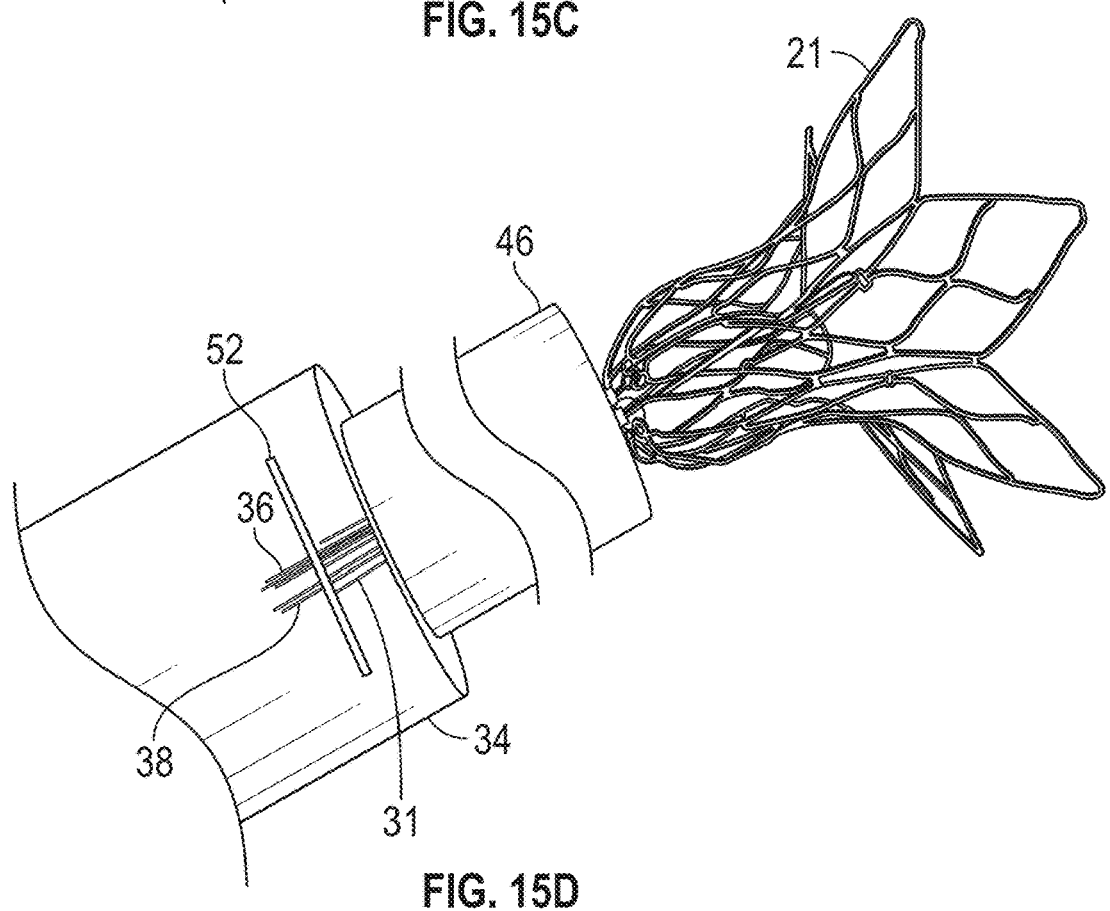
Figure 15E:
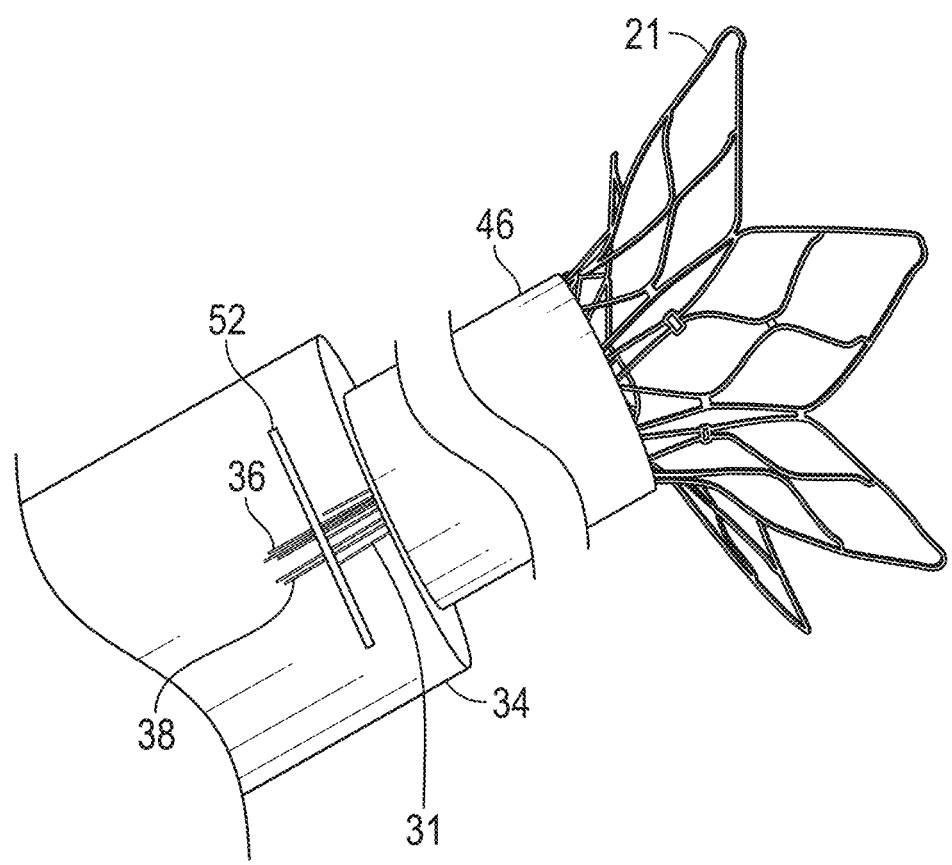
Figure 16A:
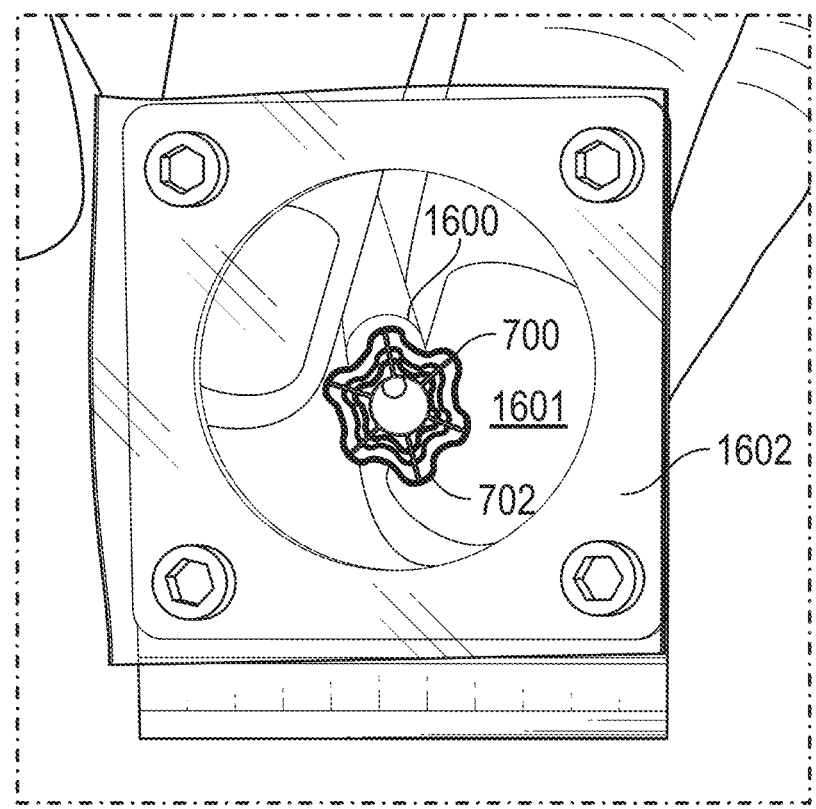
FIGS. 16A-16H are images of a device prepared and used in accordance with examples provided herein.
Figure 16B:
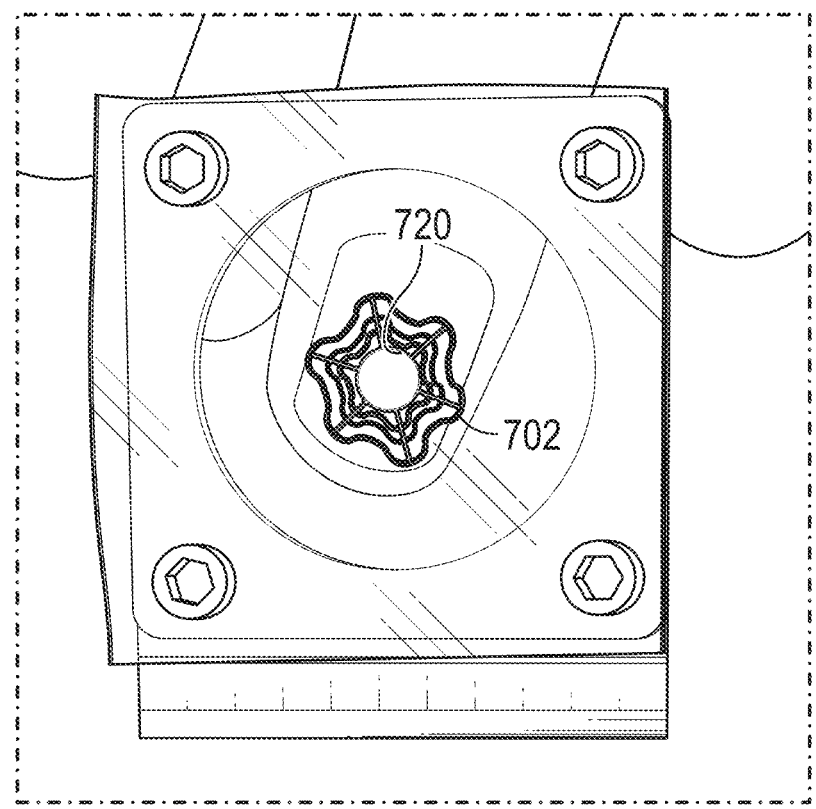
Figure 16C:
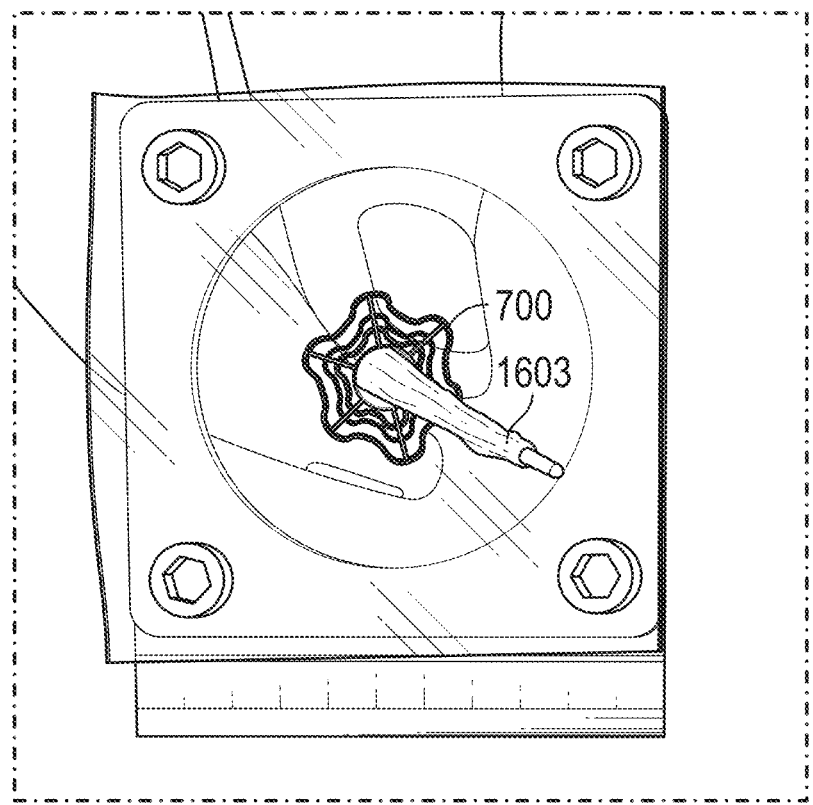
Figure 16D:
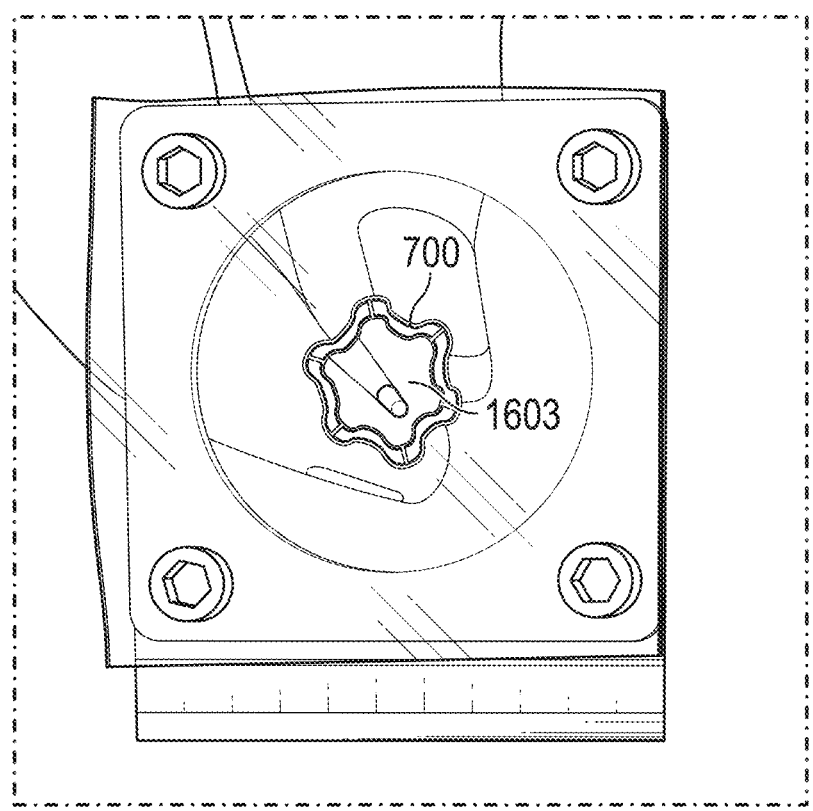
Figure 16E:
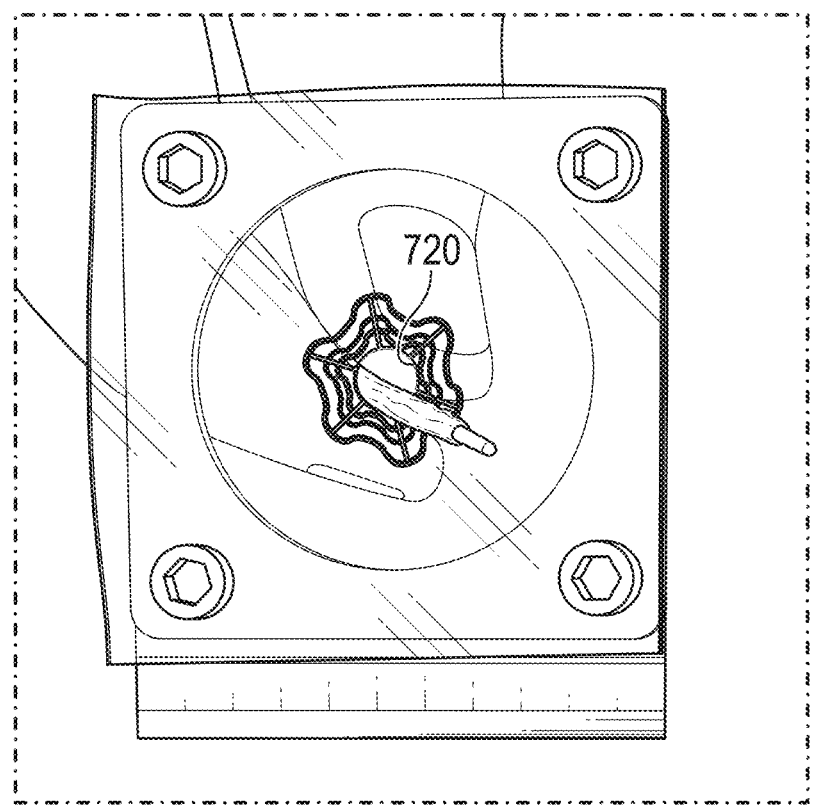
Figure 16F:
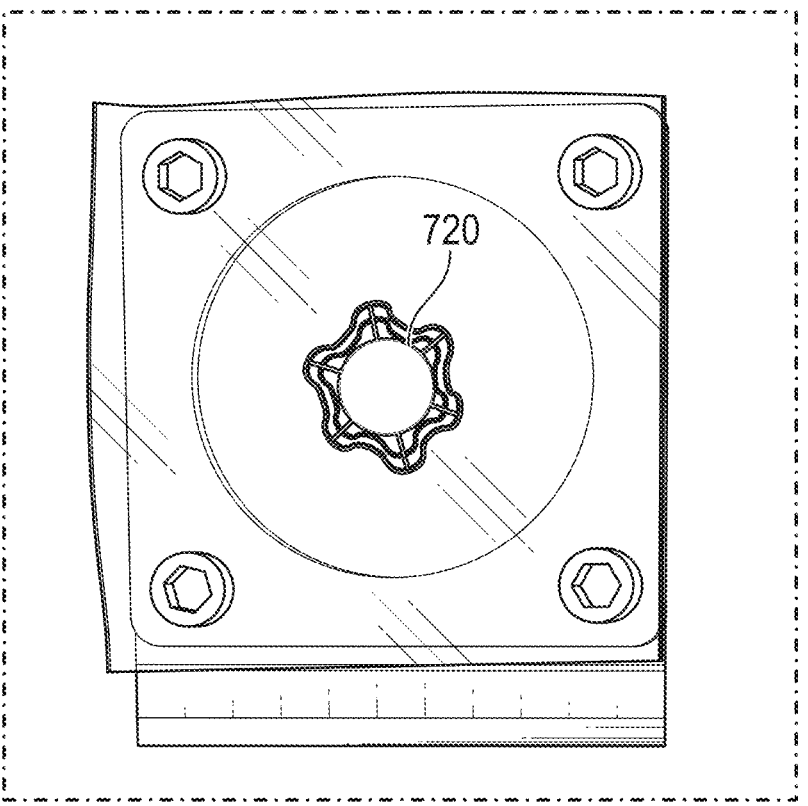
Figure 16G:
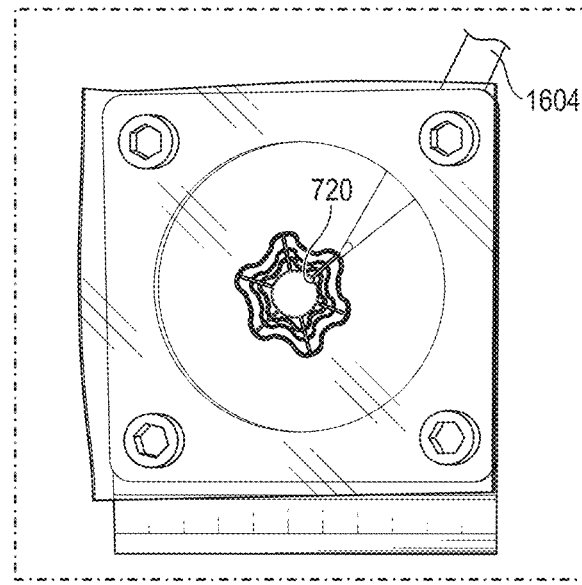
Figure 16H:
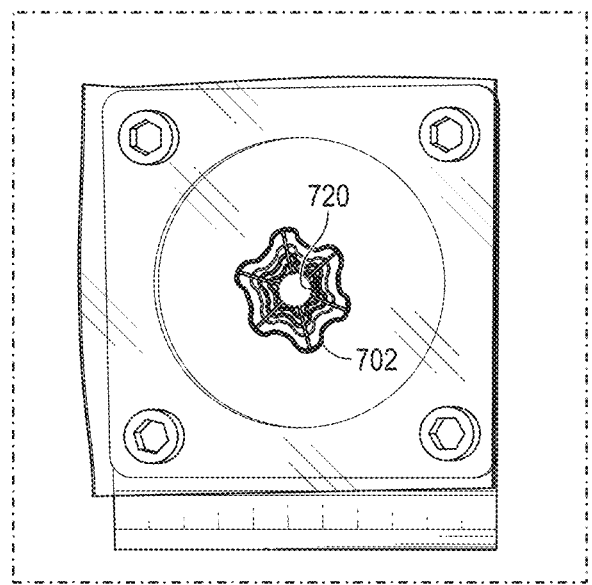

Reference is now made to FIGS. 15C-15E, which collectively show a technique for removing device 21 from subject 20, in accordance with some examples provided herein. It is noted that many of the details shown in FIGS. 15C-15E are provided by way of example only, and that many variations of the illustrated technique are included within the scope of the present disclosure. In FIG. 15C, sheath 46 is advanced until the distal end of the sheath is close to proximal portion 44 of device 21. Subsequently, control wires 36 attached to device 21 are pulled, as indicated by the arrow 54 shown in FIG. 15C, such that an inward radial force is exerted on proximal portion 44. The inward radial force causes proximal portion 44 to at least partially collapse, as shown in FIG. 15D. Following the collapse of the proximal portion of device 21, as shown in FIG. 15E, sheath 46 is advanced distally over device 21 while catheter 31 is held in place, drawing the proximal portion of device 21 into the distal end of the sheath. (In passing over device 21, the sheath may at least partly pass through the interatrial septum.) As sheath 46 continues to pass over device 21 from the position shown in FIG. 15E, the catheter may be pulled proximally while holding the sheath in place, pulling device 21 further into the sheath until the sheath collapses distal portion 40 of device 21, such that device 21 becomes entirely collapsed within the sheath. Subsequently, the sheath, containing catheter 31 and device 21, may be removed from the subject.

In some examples, sheath 46 is advanced while proximal portion 44 is collapsing, such that, as proximal portion 44 continues to collapse, the catheter passes over device 21, until the distal end of the catheter crosses through the septum and reaches the distal portion of device 21. (In such examples, the state shown in FIG. 15D may not actually come to transpire, because sheath 46 covers the proximal portion of device 21 before the proximal portion 44 of device 21 is fully collapsed.) Then, as the pulling of device 21 by catheter 31 via wires 36 continues while sheath 46 is held in place or is pushed forward, the distal end of the catheter exerts a force on the distal portion 40 of device 21, such that the distal portion of device 21 collapses, and device 21 is drawn into the catheter. In such examples, due to the sheath being advanced over device 21 while wires 36 are pulled, device 21 may be relatively unlikely to be pulled into the right atrium before collapsing into the sheath.

FIGS. 15C-15E show a nonlimiting example in which catheter 31 extends to a stopper 52 contained inside of control handle 34, wires 36 passing through stopper 52. As the wires are pulled, stopper 52 inhibits or prevents catheter 31 from moving proximally, such that most of the pulling force acts on proximal portion 44, rather than on catheter 31. Although flexible, catheter 31 is resistant to buckling, such that the pulling force is effectively transferred to proximal portion 44. In some examples, two separate tubes run through a single lumen, or two separate lumens, of catheter 31, one of these tubes holding control wires 36, and the other of these tubes holding signal wires 38. In another embodiment, control wires 36 as well as the signal wires 38, when present, run through a separate individual lumens disposed in the wall of catheter 31, leaving an enlarged central multipurpose lumen 39, as shown in FIG. 15A. Such tubes may provide additional resistance to buckling, such that the pulling force exerted on the wires is effectively transmitted to device 21. In such embodiments, stopper 52 may be used to inhibit or prevent the wire-holding tubes from moving proximally as the wires are pulled.

In some examples, proximal portion 44 may be provided in a malleable shape-memory phase at body temperature, heat set to a collapsed configuration similar to that shown in FIG. 15D, and deployed in a manner similar to that described with reference to FIGS. 15A-15B. However, instead of self-expanding, proximal portion 44 may be deployed by positioning an hourglass-shaped balloon through device 21, and inflating the balloon to expand the proximal portion. Such balloon expansion of proximal portion 44 may be performed after self-expansion of distal portion 40.

It is noted that the apparatus and methods such as described with reference to FIGS. 15A-15E may also be used for applications in which device 21 is to be permanently implanted. In such applications, during the implantation procedure, wires 36 may be used to facilitate the retrieval or repositioning of device 21, in the event that the device was not placed at the proper location. Subsequently, upon confirmation that device 21 is properly situated, wires 36 may be detached from device 21, and removed from the subject.

Working Example

The following example is intended to be purely illustrative, and not limiting of the present disclosure.

FIGS. 16A-16H are sequential images of a device prepared and used in accordance with examples provided herein. More specifically, the diabolo-shaped shunt frame device 700 described with reference to FIG. 7 was formed from NITINOL with an initial austenitic finish temperature below 20° C., so that it would be in austenitic superelastic phase at body temperature of 37° C. The superelastic device 700 was heat-set to the shape shown in FIG. 7, within a jig that formed a neck diameter of 4 mm. Subsequently, the shunt was changed from a purely self-expanding, superelastic austenitic phase to a configuration where at least some elements of the frame exhibited malleable shape-memory martensitic phase physical properties, with all dimensions, including the neck diameter, remaining the same, by reheating the device to above 500° C. in an oven for a suitable duration. At the time of FIG. 16A, within a tank of 37° C. water, a transparent membrane 1601 is suspended in tooling 1602 to simulate an atrial septum, and shunt frame device 700 is deployed from behind the opening in membrane 1601 via sheath 1600 in a manner such as described elsewhere herein. It should be noted that the distal flange 702 (toward the viewer) has self-expanded from its crimped configuration in the delivery sheath 1600, indicating that this component is at least in part in an austenitic superelastic phase at the 37° C. temperature of the water bath, in accordance with the example set forth in FIG. 8A. At the time of FIG. 16B, following deployment across the transparent membrane, the neck 720 of device 700 has an initial cross-sectional area corresponding to its heat set minimum diameter of approximately 4 mm. At the time of FIG. 16C, commercially available angioplasty balloon 1603 is inserted through the neck of device 700. At the time of FIG. 16D, balloon 1603 is inflated to a diameter of approximately 7 mm at a pressure and for a duration sufficient to deform the neck of device 700. At the time of FIG. 16E, the balloon 1603 is deflated. At the time of FIG. 16F, it may be seen that neck 720 of device 700 remains at a diameter of approximately 7 mm after balloon 1603 is withdrawn, in accordance with the example set forth in FIG. 8B. At the time of FIG. 16G, neck 720 is bathed in heated saline via rapid injection through a catheter 1604, in accordance with the example set forth in FIG. 8C. At the time of FIG. 16H, after the heating shown in FIG. 16G, neck 720 has been returned to its approximately 4 mm heat set diameter, in accordance with the example set forth in FIG. 8D, demonstrating that the neck region 720 of device 700 exhibits the desired martensitic shape-memory properties. Operations such as described with reference to FIGS. 16C-16G may be repeated any suitable number of times so as to increase and reduce the dimensions of neck 720 as desired, while first and third portions 710, 730 securely retain device 700 in the opening through membrane 1601 simulating the atrial septum. Similar operations may be performed on other devices provided herein, e.g., so as to adjust the flow rate of such devices or to permit repositioning of the devices. Accordingly, it may be understood that one or more dimensions of the present devices suitably may be increased and decreased in vivo.

One complication that can arise when adjusting the dimension of the shunt over time is tissue trauma to the atrial septum. The encapsulated shunt may be designed to promote tissue ingrowth and endothelialization and therefore expanding or reducing the encapsulated shunt after tissue has adhered to the encapsulated shunt over time can result in trauma to the atrial septum. Provided herein are devices for adjusting the dimensions of the shunt without disturbing the septal tissue surrounding the device. In particular, the device may include a bridge as described in U.S. Pat. No. 11,813, 386 to Nac, the entire contents of which are incorporated herein by reference. For example, the bridge may be formed of biocompatible material that extends between the outer surfaces of first and second flared end regions, creating a gap between the bridge and a neck region of the encapsulated shunt. The bridge may be configured to engage the patient's atrial septum, rather than the encapsulated shunt itself such that, when the device is adjusted in vivo, the bridge may be configured to remain the same outer diameter while only the inner diameter of the shunt is modified. Accordingly, the bridge prevents dehiscence that may result when the device is adjusted in vivo. Further, the bridge may mitigate any bypass flow that may flow around the outside of the device after the diameter of the neck region is reduced in vivo. In addition, the bridge may be formed of a material having properties selected to encourage tissue ingrowth to thereby facilitate anchoring of the bridge, and accordingly the shunt, to the surrounding tissue.

The bridge described above could also be used with encapsulated shunts that are not adjustable in vivo, as well as encapsulated shunts that are disposed in another portion of the human body, such as a body lumen (e.g., a blood vessel). Patients who may benefit from an interatrial shunt also may have required or will require a prior transeptal procedure resulting in a hole in the septal wall. Alternatively, the patient may have septal defect that is predilated larger than the delivery system required to implant the device described here. Incorporating the bridge of biocompatible material to the encapsulated shunt increases the outer diameter of the device, thus permitting implantation of the device in the enlarged septal hole, without affecting the inner diameter of the device and fluid flow rate throughout the device.

Figure 17A:
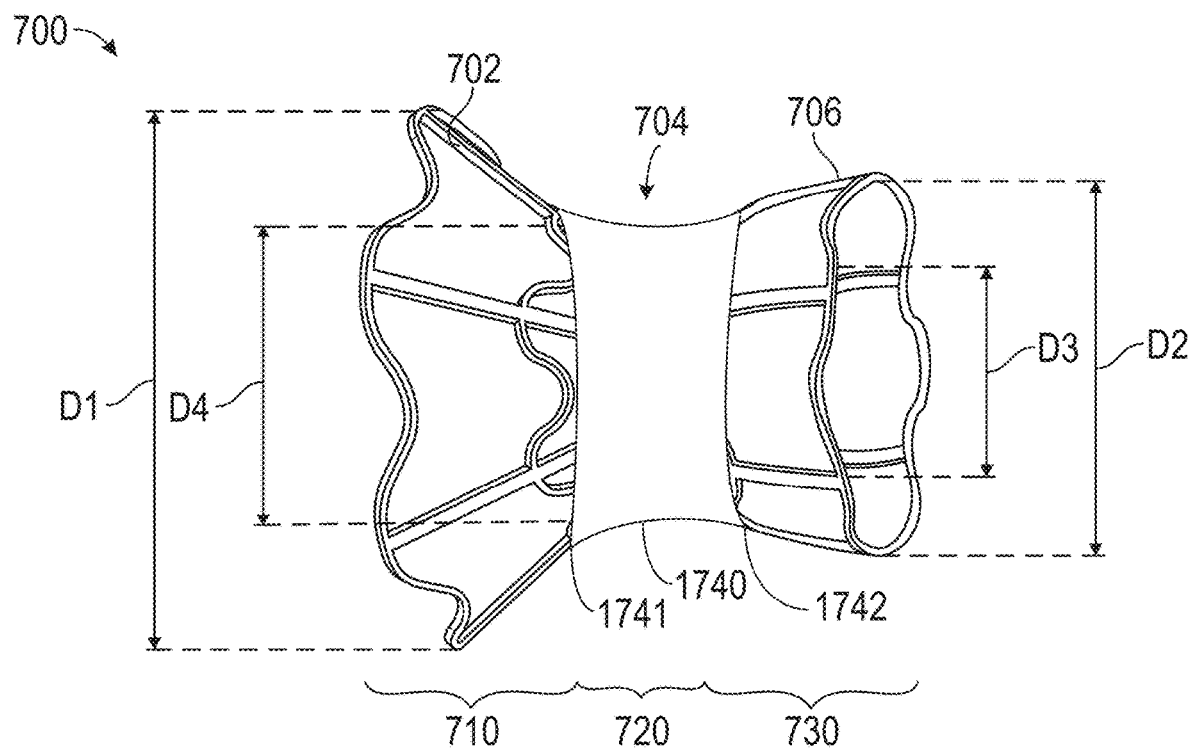
FIG. 17A is a side view of the device of FIG. 7 with a bridge constructed in accordance with the principles of the present disclosure.
Figure 17C:
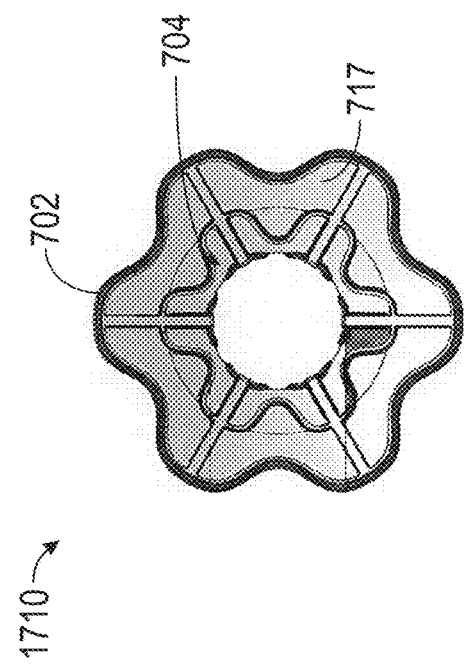
FIGS. 17B-17E are side, cross-sectional, and perspective views of the device of FIG. 17A.
Figure 17E:
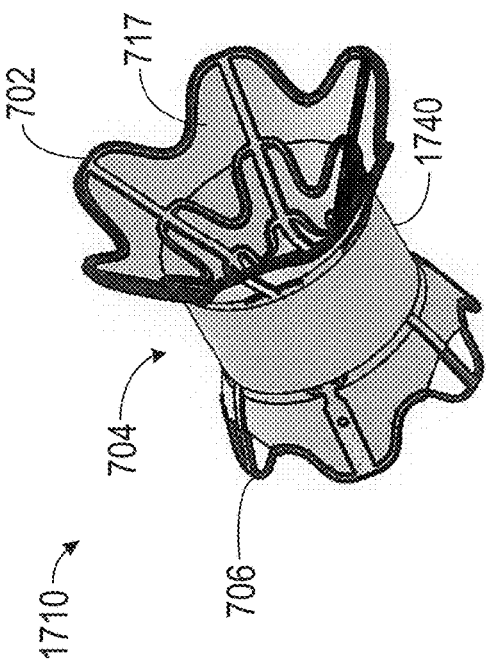

For example, referring now to FIGS. 17A and 17E, a shunt, e.g., shunt 700, with a bridge is provided. As described above, first flared end region 702 has first end region dimension D1, second flared end region 706 has second end region dimension D2, and neck region 704 has neck dimension D3 which may be increased or reduced in a manner such as described with reference to second component 720 illustrated in FIGS. 19A-19D. As shown in FIG. 17A, shunt 700 may be modified to add bridge 1740 at neck region 704, which is configured to engage a patient's atrial septum. As described above, shunt 700 is preferably encapsulated with graft material to create a shunt-graft assembly and a passageway to permit blood to flow; this graft material has been omitted from FIG. 17A to better illustrate the location of bridge 1740. Bridge 1740 may be made of a biocompatible material, such as a polymer or a natural material as described above, and may be the same material as the material used to encapsulate the frame or may be a different material. Preferably, the biocompatible material of the bridge is one that encourages tissue adherence such that contact with the septal wall is maintained if the inner diameter of the shunt is decreased. Maintaining contact with the septal wall helps prevent any fluid bypass around the outside of the device. The biocompatible material may be configured to promote tissue ingrowth over the entire bridge or over only a portion of the bridge. For example, holes may be placed at the location of bridge 1740 that is configured to engage the atrial septum while the remainder of bridge 1740 remains whole such that tissue ingrowth is not encouraged on the flared end regions. Such addition of holes or other processing to promote tissue ingrowth or encourage adhesion may be performed on the biocompatible material prior to or after the shunt is assembled.

In addition, or alternatively, bridge 1740 may be made of a different biocompatible material than the biocompatible material used to encapsulate the shunt. For example, the shunt may be encapsulated with a biocompatible material, such as ePTFE, having a sufficiently small pore size such that tissue ingrowth is mitigated and the bridge may be made of a biocompatible material having a larger pore size that is designed to encourage tissue ingrowth. Generally, the larger the pore size of the biocompatible material, the greater the adherence of tissue to the biocompatible material. In addition to encouraging tissue growth, greater porosity permits the exchange of fluids in and out of the gap between the outer surface of neck region 704 and bridge 1740. For example, bridge 1740 may be made of ePTFE that has a larger intermodal distance (e.g., approximately 60-200 μm) than the ePTFE that encapsulates the shunt.

Alternatively, bridge 1740 may be made of woven Dacron to further encourage tissue ingrowth. The Dacron may be securely attached to the encapsulated shunt using stitches. Because Dacron is bulkier than ePTFE, the cross-section of the device in the collapsed or crimped configuration may be increased, which may mean that a larger diameter sheath may be required for delivery of the device. Additional materials that may be used to promote tissue ingrowth include using a mesh-like structure, electrospun fabrics, or silicone.

In some embodiments, the shunt may be encapsulated with ePTFE having a thickness of 0.002" and an internodal distance of <=30 microns. Clowes et al., Rapid Transmural Capillary Ingrowth Provides a Source of Intimal Endothelium and Smooth Muscle in Porous PTFE Prostheses, Arterial Graft Failure, Vol. 123, No. 2, pages 220-230 (May 1986) describes that ePTFE with IND <=30 microns exhibits low porosity and Applicant's studies have shown that tissue ingrowth is inhibited within shunts encapsulated with ePTFE with IND=30 microns. On the other hand, bridge 1740 may have a thickness of 0.002" or 0.005" and a pore size to augment cellular and collagen transmural infiltration into the potential space between bridge 1740 and other layers of ePTFE. This can be done using a larger pore size ePTFE (for example with an ePTFE material having IND ranging from 60 to 200 microns). Alternatively, transmural infiltration may be encouraged by creating a pattern or plurality of perforations of similar dimension into bridge 1740 fabricated from conventional low-porosity (IND <=30 microns), either before or after its application to the shunt. Such dedicated perforation process may be performed using, e.g., an energy source such as laser, RF, etc., or a mechanical source e.g. punch, or any other technique known to those skilled in the art of thin materials processing.

In some embodiments, the frame encapsulation material is intended to block tissue ingrowth, whereas the bridge encapsulation material would be more elastic to support the significant expansion/contraction in diameter, without damaging the Fossa Ovalis or the frame encapsulation material. In some embodiments, the gap 1743 between the bridge 1740 and the neck region 704 increases as the shunt neck region 704 is contracted. Bridge 1740 may be configured to remain engaged with the patient's atrial septum when the neck region is contracted. In some embodiments, the biocompatible material of bridge 1740 has a porosity (as measured by, e.g., its internodal distance) greater than the porosity of the biocompatible material of the encapsulation of the shunt frame. As such, the internodal distance of the bridge material may be selected to permit tissue ingrowth while the internodal distance of the encapsulation material is selected to inhibit tissue ingrowth. In some embodiments, the internodal distance of the bridge is greater than 30 microns (e.g., in a range of 45-200 microns) while the internodal distance of the encapsulation is less than or equal to 30 microns. In one embodiment, the internodal distance of the bridge is 60 microns while the internodal distance of the encapsulation is 30 microns. The biocompatible material of the bridge and the biocompatible material of the encapsulation may be expanded polytetrafluoroethylene (ePTFE).

Bridge 1740 may have a length shorter than shunt-graft assembly 1710 and a diameter greater than the diameter of neck region 704. Bridge 1740 may have first end 1741 and second end 1742 and may be shaped and sized such that first end 1741 is disposed approximately half way up first flared end region 702 and second end 1742 is disposed approximately half way up second flared end region 706. Alternatively, first end 1741 and second end 1742 may extend further up first flared end region 702 and second flared end region 706 or may be attached nearer neck region 704. Bridge 1740 may be stretched such that a gap is created between the outer surface of neck region 704 and the inner surface of bridge 1740. The gap may be widest at the narrowest point of the outer surface of neck region 704.

As described above, the encapsulated shunt may be adjusted in vivo to increase or decrease the neck dimension and thereby adjust the fluid flow rate through the shunt. Because the encapsulated shunt may be designed to promote tissue ingrowth and endothelialization, tissue may adhere to the shunt over time. Adjustments of the encapsulated shunt to increase or decrease the dimensions can therefore result in trauma to the atrial septum. Bridge 1740 is designed to prevent dehiscence and to mitigate the tissue trauma that can result from such adjustments. Bridge 1740 is configured to engage with the atrial septum and defines outer diameter D4. Preferably, outer diameter D4 is larger than neck dimension D3. In one embodiment, outer diameter D4 may be 7-9 mm and neck dimension D3 may be 4.5-5.5 mm. When the device is adjusted in vivo, bridge 1740 may be configured to remain the same outer diameter D4 while only the neck dimension D3 of the shunt and the size of the gap is modified. Due to the creation of a gap between neck region 704 and bridge 1740, neck dimension D3 may be decreased or increased up to outer diameter D4 causing an increase or decrease in the size of the gap, without disturbing the septal tissue contacting and surrounding bridge 1740 and while maintaining contact with the septal tissue such that leakage or bypass flow around the outer surface of the shunt is minimized.

Bridge 1740 could also be used with encapsulated shunts that are not adjustable in vivo. In particular, incorporating bridge 1740 into an encapsulated shunt may be beneficial for patients who have an enlarged hole prior to implantation of the device, for example, from a prior transseptal procedure, or have a septal defect that is predilated larger than the delivery system required to implant the device described herein. For example, for a patient with severe mitral regurgitation and poor left ventricular function, it may be clinically desirable to first perform a repair procedure on the mitral valve, e.g. MitraClip® of mitral annuloplasty by the percutaneous transseptal approach, followed by interatrial shunt placement. These mitral valve procedures currently use a 23Fr I.D. (~8 mm outer diameter) guiding catheter to cross the foramen ovalis. After mitral repair, a shunt with an outer minimal diameter matching the larger aperture defect caused by the prior procedure may be implanted, wherein the conduit as a smaller diameter desirable for shunting (e.g. 5.0 to 6.5 mm). Likewise, such shunts advantageously may be used where, during the transseptal procedure, the fossa ovalis has been torn, thus creating a larger aperture defect than required.

Incorporating the bridge of biocompatible material to the encapsulated shunt increases the outer diameter of the device, thus permitting implantation of the device in the enlarged septal hole, without affecting the inner diameter and fluid flow rate throughout the device. Further, bridge 1740 permits the inner diameter of the encapsulated shunt to be temporarily increased, for example, during a separate transseptal procedure after implantation of the device, without disturbing the outer diameter of the neck region, thus minimizing the risk of tears to the septal tissue. As will be understood by a person having ordinary skill in the art, the present devices described herein, e.g., with reference to FIGS. 1A-1E, 2A-2E, 3A-3D, 4A-4B, 5A-5B, 6, 7, 8A-8D, 9A-9B, 15A-15E, 20A-20F, and 21A-22I, may similarly incorporate a bridge.

Figure 17B:
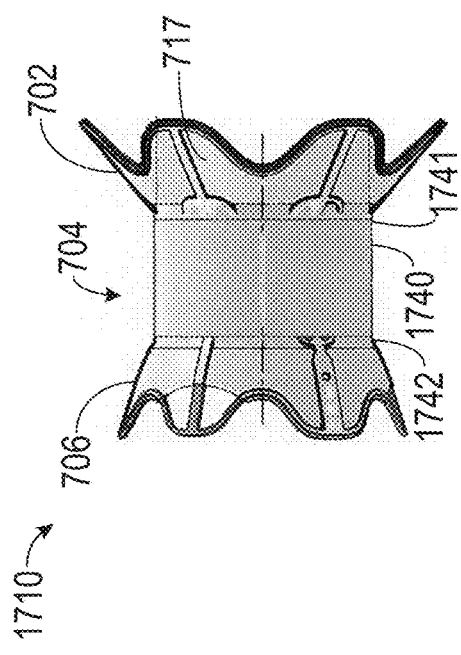
Figure 17D:
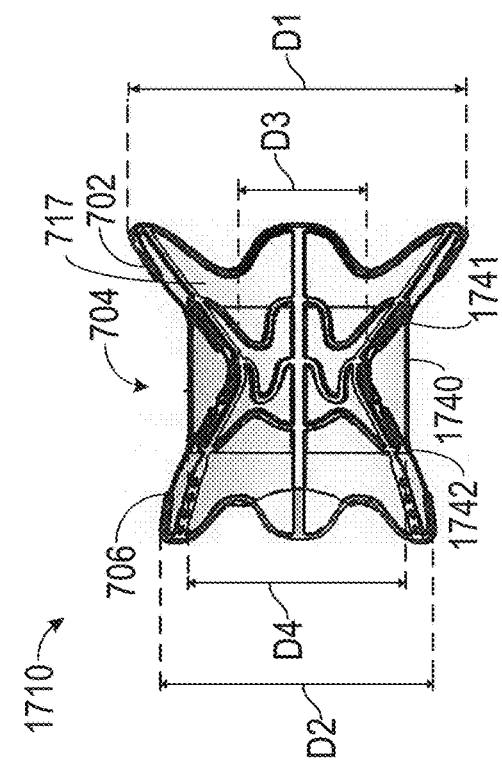

Referring now to FIGS. 17B to 17E, additional side, front, side cross-sectional, and perspective views are shown, respectively. FIG. 17B shows shunt 700 encapsulated with biocompatible material 717 to create shunt-graft assembly 1710 and to define a flow path through shunt-graft assembly 1710. As shown in FIG. 17D, neck region 704 defines the inner diameter, neck dimension D3, of the passageway through which blood flows. Bridge 1740 surrounds the entire neck region 704 to define outer diameter D4.

Figure 18A:
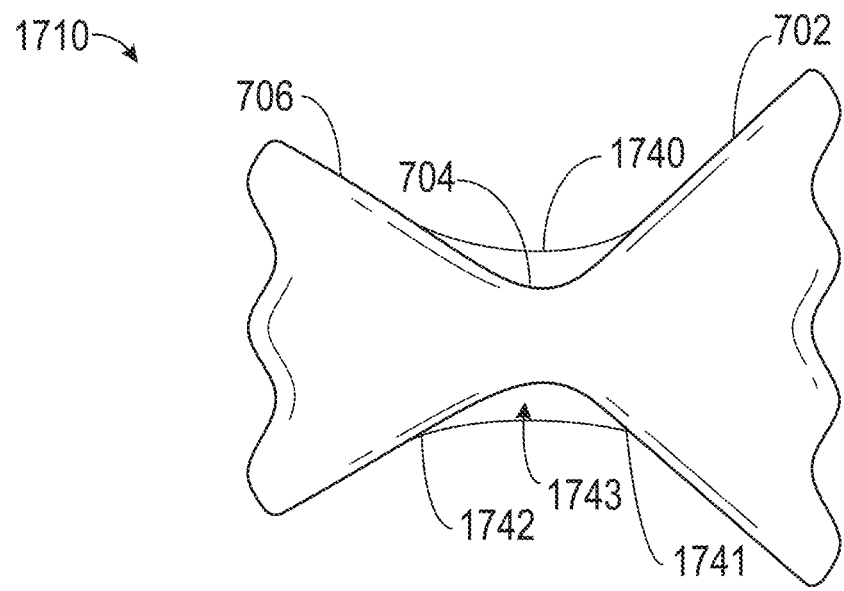
FIGS. 18A and 18B are cross-sectional side views of the device of FIG. 17A.
Figure 18B:
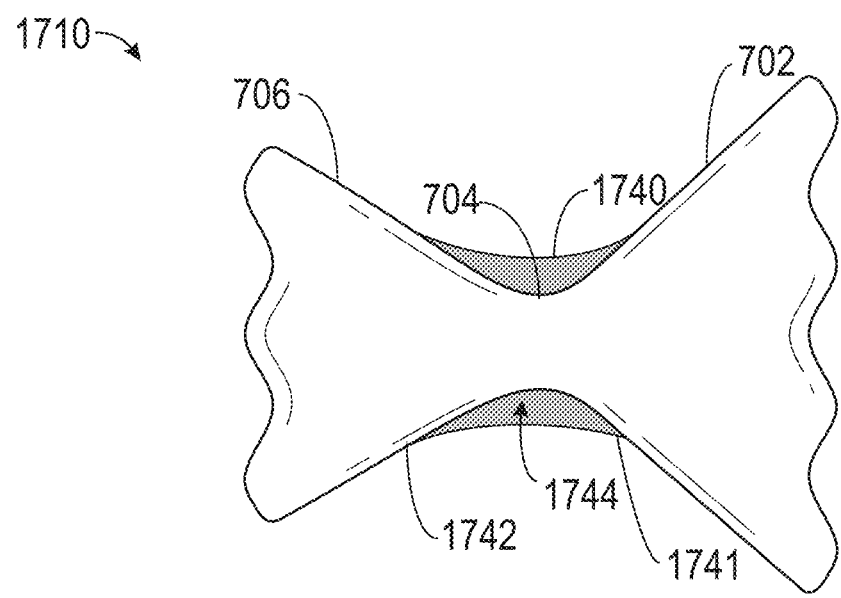

Referring now to FIGS. 18A and 18B, cross-sectional side views of the device of FIG. 17A showing an unfilled and a filled gap between the bridge and the encapsulated shunt. Bridge 1740 is attached at first end 1741 to first flared end region 702 and is attached at second end 1742 at second flared end region 706. Preferably, bridge 1740 is stretched such that a gap is created between neck region 704 and bridge 1740. Gap 1743 may be filled with a flexible biocompatible material or a liquid biocompatible material, such as a hydrogel. Alternatively, gap 1743 may be filled with bodily fluids upon delivery and implantation of shunt-graft 1710. This embodiment is advantageous where the dimensions of the shunt are configured to be adjusted in vivo. Specifically, gap 1743 may be increased or decreased during such adjustments while the outer diameter of the neck region that contacts the atrial septum (e.g., the bridge) remains the same, thus minimizing any tissue trauma. For example, bridge 1740 may be made of cPTFE having holes such that when shunt-graft assembly 1710 expands, the biocompatible material disposed within gap 1743 is configured to permeate through bridge 1740.

As shown in FIG. 18B, the gap between bridge 1740 and the encapsulated shunt may be filled with a biocompatible material, such as a polymer or a natural material that is not flexible such that the gap remains the same size even if the dimensions of shunt-graft assembly 1710 are adjusted. This embodiment may be beneficial where the device is designed to be implanted into an enlarged septal hole and the device is not configured to be adjusted in vivo. In particular, because the inner diameter of the device may not be adjusted, the dimensions of gap 1744 do not need to be adjustable. Accordingly, gap 1744 may be filled with a solid material or a low durometer material such as a hydrogel, which may increase the stability of the device and make the bridge more robust.

Figure 19A:
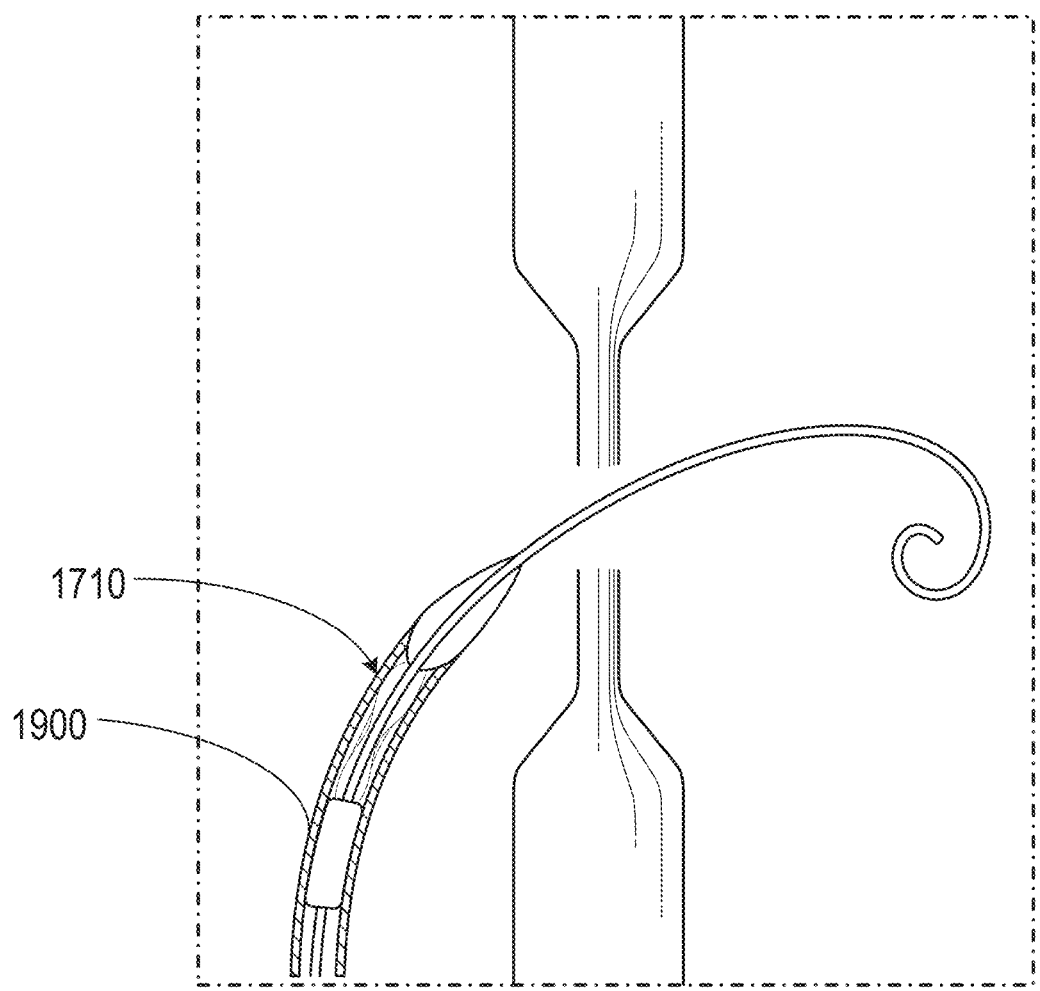
FIGS. 19A-19E illustrate example steps for using the device of FIG. 17A in the human body.
Figure 19B:
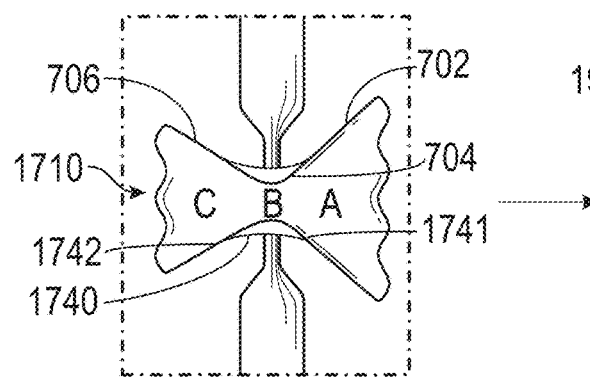

FIGS. 19A-19E schematically illustrate example steps for using the device of FIG. 17A in the human body. Shunt-graft assembly 1710 may be crimped to a cylindrical shape, for example by pushing it through a conical loading device. In one non-limiting example, shunt-graft assembly 1710 may be crimped to an outer dimension of about 4.6 mm, the inside dimension of a 14F Cook sheath. For example, FIG. 19A illustrates shunt-graft assembly 1710 disposed within sheath 1900. As will be understood by one of skill in the art, shunt-graft assembly 1710 may be crimped to a smaller or larger outer dimension if a different size Cook sheath is used. In addition, a layer of hydrogel may be placed with gap 1744 between bridge 1740 and shunt-graft assembly 1710, which may affect the crimped dimension. The delivery catheter and sheath 1900 may be designed as described in U.S. Pat. No. 9,713,696 to Yacoby, U.S. Pat. No. 11,612,385 to Nae, entitled "Systems and Methods for Delivering Implantable Devices across an Atrial Septum," U.S. Patent App. Pub. No. 2022/0184356 to Nae, and/or WO 2023/079498, each assigned to the assignee of the present application, the entire contents of each of which are incorporated by reference herein. The sheath may be percutaneously placed through a blood vessel to a desired location in the human body. As the crimped shunt is pushed out of sheath 1900, the self-expanding superelastic flared end regions spring open to their set configuration, while the malleable shape-memory central neck region remains constrained at or near its crimped dimension, e.g., in a manner such as illustrated in FIG. 19B in which bridge 1740, disposed over neck region 704 (designated "B" and corresponding to second component 720), engages an opening in the human body.

Depending on the desired direction of blood flow through shunt-graft assembly 1710, first flared end region 702 and second flared end region 706 (designated "A" or "C" and corresponding to first component 710 or third component 730) provides an inlet and the other of the flared ends (designated "C" or "A" and corresponding to third component 730 or first component 710) provides an outlet. For example, bridge 1740 may engage an opening created through a fossa ovalis of an interatrial septum between a right atrium and a left atrium, one of the flared ends extends into the right atrium, and the other flared end extends into the left atrium. In some configurations, the flared end in the right atrium is an inlet and the flared end in the left atrium is an outlet, whereas in other configurations, the flared end in the left atrium is an inlet and the flared end in the right atrium is an outlet. As used herein, "inlet" means component with ingress of blood flow, and "outlet" means component with outgress (egress) of blood flow. The particular components that respectively may be used to provide ingress and outgress (egress) of blood flow may be selected based on the condition being treated. For example, in HF, the inlet may be on the left atrial (LA) side, where blood flow from LA to right atrium (RA), and LA decompression, are desirable. In contradistinction, in PAH, the interatrial pressure gradient is reversed causing R to L flow and RA decompression, and the inlet is on the RA side.

Figure 19C:
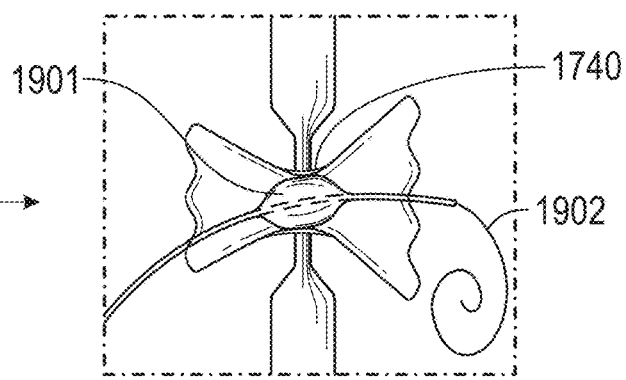

The cross sectional area (and dimension) of the orifice provided by the malleable shape-memory central neck region may be increased or reduced so as to adjust the flow of fluid through shunt-graft assembly 1710. For example, in a manner such as illustrated in FIG. 19C, the neck region may be expanded by balloon dilatation using balloon 1901 (e.g., a 12 mm diameter balloon), which may be fed through the orifice using a wire 1902. Preferably, balloon 1901 expands the neck region only to a threshold outer diameter, defined by bridge 1740, such that expansion of the neck region does not affect the outer diameter of the device or disturb the septal tissue surrounding bridge 1740. For example, bridge 1740 may be sized and shaped to define an outer diameter of 7-14 mm and balloon 1901 may be configured to expand the neck region up to 9 mm.

Figure 19D:
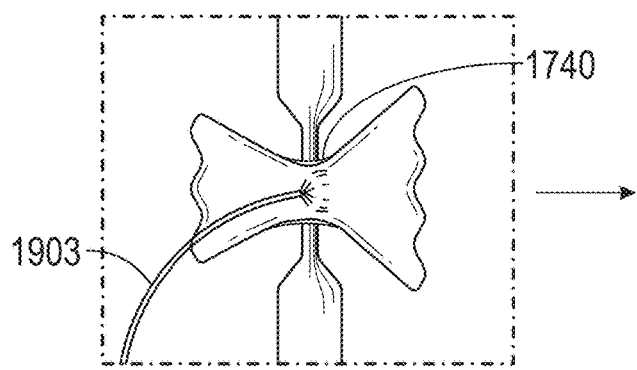
Figure 19E:
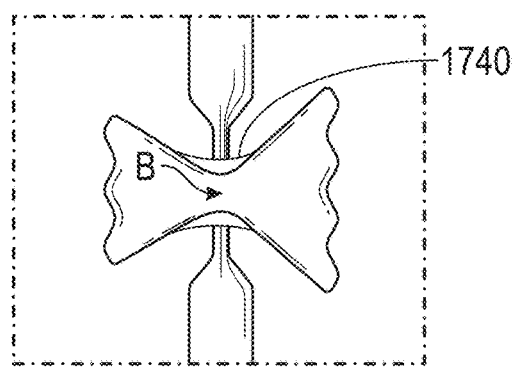

Additionally, in a manner such as illustrated in FIG. 19D and as described above, the neck region may be contracted by injecting, via a distal end of catheter 1903, a bolus of hot saline having a temperature above the Af of the malleable shape-memory material (e.g., at 40-65° C. or 45-65° C.), which may cause the neck region to return to its heat-set dimension, which may be different from its crimped dimension and preferably is 4.5-5.5 mm. FIG. 19D illustrates one method of heating the neck region, but other methods may be used. For example, the saline may be injected via side-holes in catheter 1903. Further, a second balloon catheter may be inserted through shunt-graft assembly 1710 such that the balloon is distal to the location the saline is delivered and the balloon may be expanded to block blood flow through shunt-graft assembly 1710 during delivery of the saline. In other examples, a pair of electrodes may be positioned to contact shunt-graft assembly, e.g., via catheter 1903, and actuated at an appropriate voltage and frequency to heat the neck region to or above its Af. In still other examples, other suitable means of locally applying heat to shunt 700, such as a laser, magnetic inductance, electrical resistance, or the like, may be used. Preferably, the return of the neck region to its heat-set dimension does not affect the outer diameter of bridge 1740, as illustrated in FIG. 19E.

For example, heat from the saline may cause the malleable shape-memory material to transition to an austenitic phase, contracting the neck region back to its crimped (or otherwise heat set) dimension, following which the neck region cools to body temperature and transitions back to its martensitic phase. The saline may be delivered in any suitable manner, for example by a flexible catheter having one or more apertures (e.g., one end hole, one side hole, or multiple side-holes) through which hot saline may flow and that may be placed within the neck region, for example, over a guidewire through the neck region. In one non-limiting example, the neck region may have its crimped inner dimension, typically 1-2 mm, at a first time, such as when initially deployed in a manner such as illustrated in FIG. 19B. The neck region then may be expanded using balloon dilatation to any desired larger dimension between the crimped dimension and the outer diameter of bridge 1740 at a second time. The neck region then may be contracted using hot saline to its heat-set dimension at a third time. The heat-set dimension is determined by the size of the jig used in a heat-setting step during manufacture and may be approximately the same as, may be smaller than, or may be larger than the dimension of the neck region in the crimped state. The heat-set dimension may be greater than the dimension of the catheter used to deliver hot saline, and greater than the deflated dimension of the dilation balloon, but smaller than or equal to the smallest anticipated desired final shunt dimension, for example 4 mm. The neck region then again may be expanded using balloon dilatation to any desired larger dimension between 4 mm and the outer diameter of bridge 1740 at a second time. Any suitable number of expansions and contractions may be applied to the neck region, at any desired time or at separate times than one another, so as to provide a suitable, and customized, flow of fluid through the device for each given patient.

It will be appreciated that what constitutes a suitable flow of fluid for a given patient also may change over time, and that the present devices suitably may be adjusted so as to provide that flow of fluid as appropriate, or so as to suitably fixate the devices within a lumen. It will also be appreciated that the self-expanding superelastic components are not affected by the injection of hot saline, and so will retain their initial full expanded dimension while the shape-memory component (in this example the neck region) is being adjusted. Furthermore, any suitable method for heating the shape memory materials may be used besides or in addition to hot saline, e.g., RF heating or the use of a laser, magnetic inductance, electrical resistance, or the like.

As described above, the present devices may comprise individual components that are formed separately and assembled together. For example, the first and second expandable end regions may be formed and heat treated to achieve the superelastic properties described herein, separate from the neck region, which may be formed and heat treated to achieve the martensitic, shape-memory properties described herein. By treating the shape-memory components separate from the superelastic components, the components may be treated in large batches without a complex treatment apparatus as may be required for manufacturing hybrid shunts from a unitary nitinol frame, which may significantly reduce manufacturing time. As described in further detail below with regard to FIGS. 20A to 22I, the components of the various devices described herein may be assembled together via interlocking shapes that retain the advantages of unitary construction, particularly, a smooth, continuous transition between the components throughout the range of device dimensions, e.g., neck diameters, as discontinuous changes in lumen diameter may introduce undesirable eddies and/or turbulence in flow. Such flow disturbances can lower the discharge coefficient or even produce platelet activation and thrombus formation, or conceivably even damage to red blood cells (hemolysis).

Figure 20A:
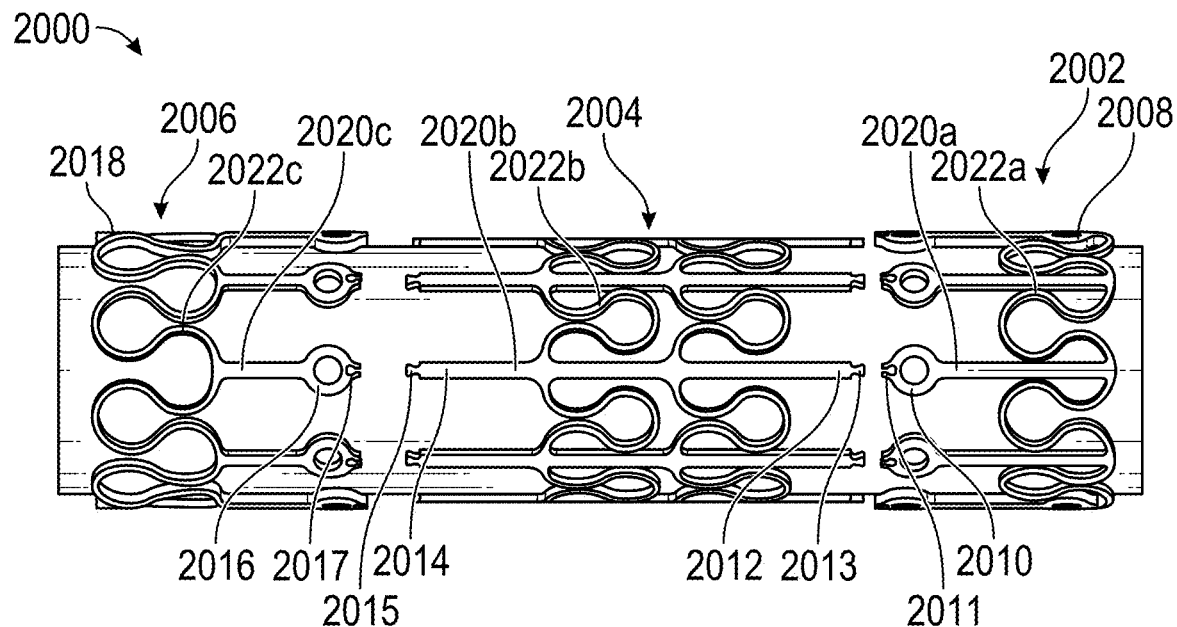
FIGS. 20A and 20B illustrate another example device with an internal dimension that can be reduced and increased in vivo having interlocking components in an unassembled configuration.
Figure 20B:
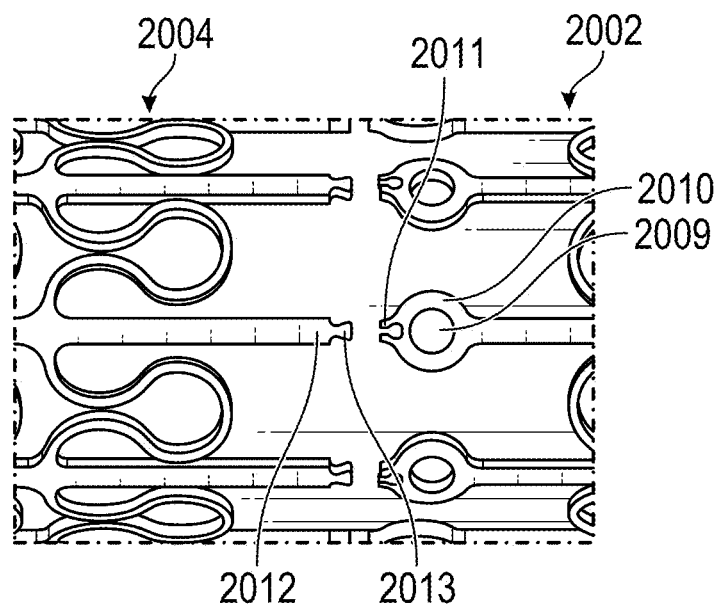

Referring now to FIGS. 20A-20F, a hybrid shunt device having interlocking components with different shape-memory properties that are treated separately and assembled together is provided. FIGS. 20A and 20B illustrate hybrid shunt 2000 in an unassembled configuration, e.g., after the separate components have been treated to achieve the desired material properties. For example, shunt 2000 may be formed of first end region 2002, neck region 2004, and second end region 2006. As described above, neck region 2004 may be treated such that it is malleable at body temperature, e.g., having an Af temperature between about 40-60° C., and first end region 2002 and second end region 2006 may be treated such that they are superelastic at body temperature, e.g., having an Af temperature between about 5-20° C.

As shown in FIG. 20A, first end region 2002 may include proximal end 2008 and distal end 2010 having a plurality of first end region connectors 2011, neck region 2004 may include proximal end 2012 having a plurality of proximal neck region connectors 2013 and distal end 2014 having a plurality of distal neck region connectors 2015, and second end region 2006 may include proximal end 2016 having a plurality of second end region connectors 2017 and distal end 2018. Like device 700 of FIG. 7, each of first end region 2002, neck region 2004, and second end region 2006 may be formed of a plurality of longitudinal extending struts interconnected via one or more circumferentially extending sinusoidal rings. For example, as shown in FIG. 20A, first end region 2002 may include a plurality of longitudinal struts 2020a interconnected via sinusoidal ring 2022a, such that the plurality of first end region connectors 2011 are disposed at distal end 2010 of each of longitudinal struts 2020a. Neck region 2004 may include a plurality of longitudinal struts 2020b interconnected via sinusoidal rings 2022b, such that the plurality of proximal neck region connectors 2013 are disposed at proximal end 2012 of each of longitudinal struts 2020b and the plurality of distal neck region connectors 2015 are disposed at distal end 2014 of each of longitudinal struts 2020b. Second end region 2006 may include a plurality of longitudinal struts 2020c interconnected via sinusoidal ring 2022c, such that the plurality of second end region connectors 2017 are disposed at proximal end 2016 of each of longitudinal struts 2020c. As will be understood by a person having ordinary skill in the art, although FIG. 20A illustrates first end region 2002 and second end region 2006 having a single sinusoidal ring, first end region 2002 and second end region 2006 may each include more than one sinusoidal ring interconnecting plurality of longitudinal struts 2020a, 2020c. Similarly, although FIG. 20A illustrates neck region 2004 having two sinusoidal rings, neck region 2004 may have less or more than two sinusoidal rings interconnecting plurality of longitudinal struts 2020b. Moreover, shunt 2000 may include less or more longitudinal struts than is illustrated in FIG. 20A.

Each connector of the plurality of first end region connectors 2011 of first end region 2002 may have a shape configured to interlock with a complementary shape of each connector of the plurality of proximal neck region connectors 2013 of neck region 2004, and each connector of the plurality of second end region connectors 2017 of second end region 2006 may have a shape configured to interlock with a complementary shape of each connector of the plurality of distal neck region connectors 2015 of neck region 2004. For example, the complementary shapes of first end region connectors 2011 and proximal neck region connectors 2013, and second end region connectors 2017 and distal neck region connectors 2015 may include tab and socket elements. As will be understood by a person having ordinary skill in the art, other complementary shapes may be used that provide an interlocking puzzle-like connection.

For example, as shown in FIG. 20B, first end region connectors 2011 may include a socket element and proximal neck region connectors 2013 may include a tab element. Similarly, distal neck region connectors 2015 may include a tab element and second end region connectors 2017 may include a socket element. As will be understood by a person having ordinary skill in the art, first end region connectors 2011 and second end region connectors 2017 alternatively may include a tab element, whereas proximal neck region connectors 2013 and distal neck region connectors 2015 include a socket element. In some embodiments, distal end 2010 of first end region 2002 (and similarly proximal end 2016 of second end region 2006) may include eyelet 2009 adjacent to socket element 2011 to improve structurally integrity of socket element 2011 while also providing flexibility to first end region 2002 as first end region 2002 transitions between a collapsed delivery state and an expanded deployed state, as well as during adjustment of the lumen diameter of neck region 2004. Moreover, a radiopaque marker may be disposed within eyelet 2009 to facilitate visualization of shunt 2000, e.g., under fluoroscopy.

As shown in FIG. 20B, socket element 2011 includes an opening sized and shaped to fixedly receive tab element 2013. Preferably, when socket element 2011 and tab element 2013 are at the same temperature, tab element 2013 is slightly larger than the opening of socket element 2011 such that tab element 2013 may be permanently fixed to socket element 2011 when tab element 2013 is disposed within the opening of socket element 2011. Accordingly, tab element 2013 may be thermally contractible, e.g., via cooling, such that tab element 2013 transitions from a first size to a second size smaller than the first size, and smaller than the opening of socket element 2011. While in the thermally contracted state having the second size, tab element 2013 may be fitted within the opening of socket element 2013, such that when tab element 2013 and socket element 2011 are brought to the same temperature while tab element 2013 is disposed within the opening of socket element 2011, tab element 2013 may be permanently fixed to socket element 2011. For example, tab element 2013 may thermally expand to its first size, such that tab element 2013 is fixed within the opening of socket element 2011, e.g., via an interference fit. When tab element 2013 is fixed within the opening of socket element 2011, tab element 2013 and socket element 2011 form a rigid connection that provides a smooth, continuous transition between first end region 2002 and neck region 2004, such that first end region 2002 may bend uniformly relative to neck region 2004 as a single element would. Tab elements 2015 at distal end 2014 of neck region 2004 may be fixed to socket elements 2017 at proximal end 2016 of second end region 2006 in the same manner as tab elements 2013 and socket elements 2011 described herein.

Additionally, or alternatively, socket element 2011 may be thermally expandable, e.g., via heating, such that the opening of socket element 2011 transitions from a first size to a second size larger than the first size, and larger than tab element 2013. While in the thermally expanded state having the second size, tab element 2013 may be fitted within the opening of socket element 2011, such that when tab element 2013 and socket element 2011 are brought to the same temperature while tab element 2013 is disposed within the opening of socket element 2011, tab element 2013 may be permanently fixed to socket element 2011. For example, socket element 2011 may thermally contract to its first size, such that tab element 2013 is fixed within the opening of socket element 2011, e.g., via an interference fit. Accordingly, tab element 2013 and socket element 2011 may form a rigid connection that provides a smooth, continuous transition between first end region 2002 and neck region 2004, such that first end region 2002 may bend uniformly relative to neck region 2004 as a single element would. In some embodiments, tab element 2013 and socket element 2011 may be welded together to permanently fix first end region 2002 to neck region 2004, and similarly tab element 2015 and socket element 2017 may be welded together to permanently fix second end region 2006 to neck region 2004. Moreover, in some embodiments, the plurality of first end region connectors 2011 also may be configured to interlock with the plurality of distal neck region connectors 2015, and the plurality of second end region connectors 2017 also may be configured to interlock with the plurality of proximal neck region connectors 2013.

Figure 20C:
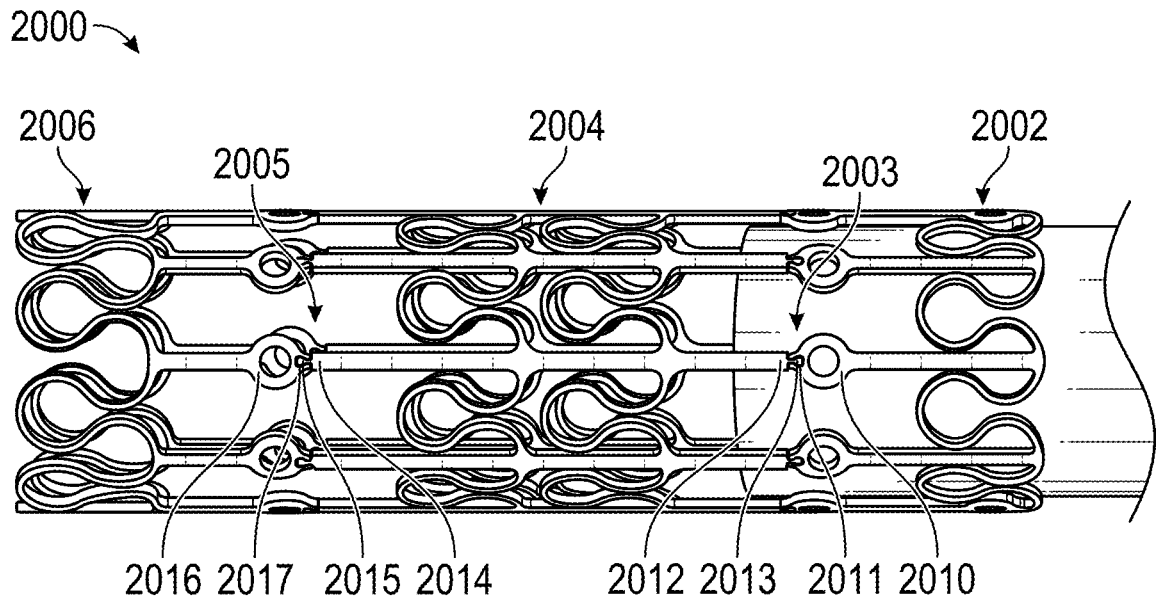
FIGS. 20C and 20D illustrate the device of FIGS. 20A and 20B in an assembled configuration in a collapsed delivery state.
Figure 20D:
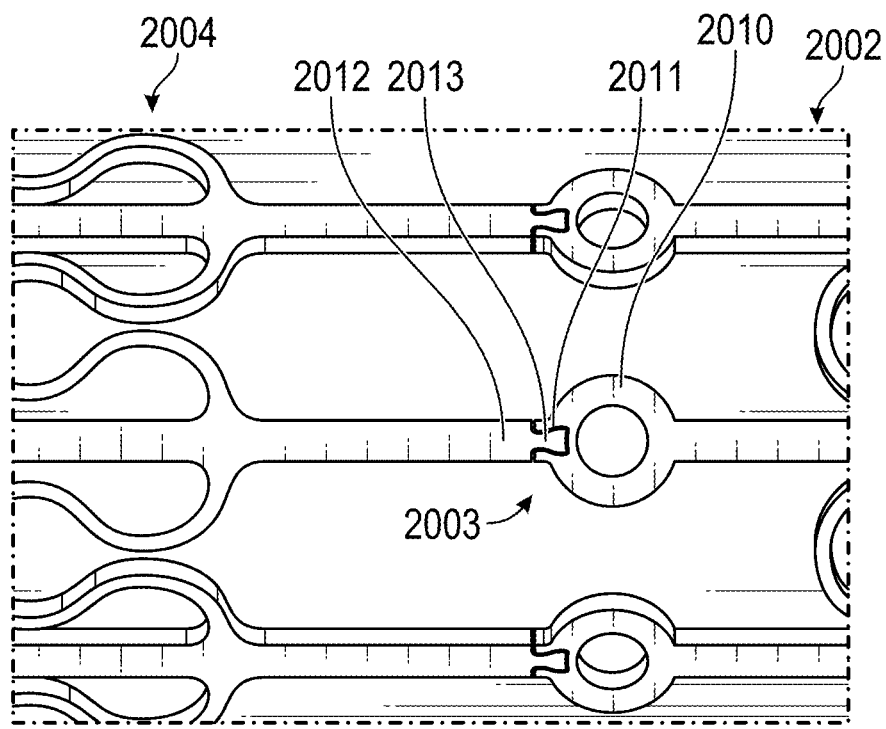

FIGS. 20C and 20D illustrate the components of shunt 2000 permanently fixed together in an assembled configuration where first end region 2002 is permanently fixed to neck region 2004 via first end region connectors 2011 and proximal neck region connectors 2013 at first connection 2003, and second end region 2006 is permanently fixed to neck region 2004 via second end region connectors 2017 and distal neck region connectors 2015 at second connection 2005. As shown in FIG. 20C, each of first end region connectors 2011 may be permanently fixed to proximal neck region connectors 2013 along a single plane at first connection 2003, and each of second end region connectors 2017 may be permanently fixed to each of distal neck region connectors 2015 along a single plane at second connection 2005. For example, the planes may be parallel to each other and may be perpendicular to a longitudinal axis of neck region 2004.

Alternatively, each of first end region connectors 2011 may be permanently fixed to each of proximal neck region connectors 2013 in a staggered manner along the circumference of shunt 2000, such that stress is distributed to alternate sides of the connections, thus distributing the strain and producing a smoother transition between components. For example, every other connection of first end region connectors 2011 and proximal neck region connectors 2013 may be offset from the adjacent connections of first end region connectors 2011 and proximal neck region connectors 2013 therebetween. Accordingly, every other longitudinal strut of first end region 2002 may longer (or shorter) than the adjacent longitudinal struts therebetween of first end region 2002, and for every longer (or shorter) longitudinal strut of first end region 2002, the corresponding longitudinal strut of neck region 2004 may be shorter (or longer) than the adjacent longitudinal struts therebetween of neck region 2004. Each of second end region connectors 2017 may similarly be permanently fixed to each of distal neck region connectors 2015 in a staggered manner along the circumference of shunt 2000.

Figure 20E:
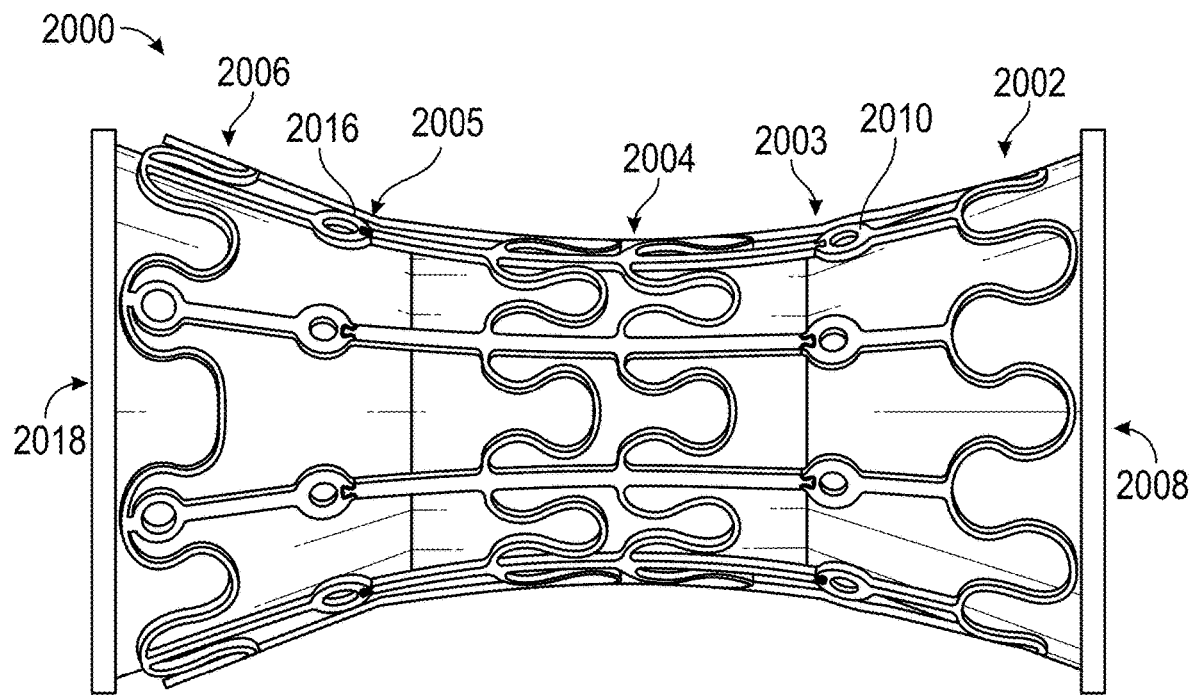
FIGS. 20E and 20F illustrate the device of FIGS. 20A and 20B in an assembled configuration in an expanded deployed state.
Figure 20F:
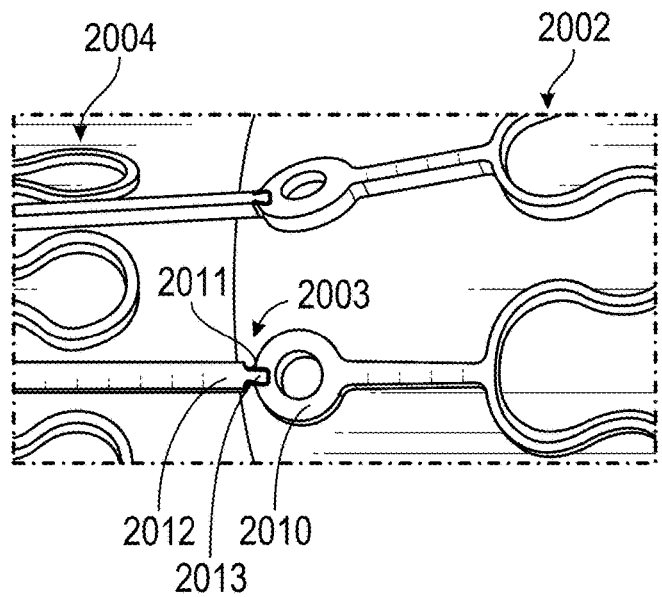

FIGS. 20E and 20F illustrate assembled shunt 2000 with first end region 2002 and second end region 2006 in their expanded deployed states. As shown in FIG. 20E, in the expanded state, proximal end 2008 of first end region 2002 flares radially outward from distal end 2010 at first connection 2003, and distal end 2018 of second end region 2006 flares radially outward from proximal end 2016 at second connection 2005. Moreover, as described above, the components of shunt 2000 are constructed such that first connection 2003 provides a smooth, continuous transition from neck region 2004 to first end region 2002, as shown in FIG. 20F, and second connection 2005 provides a smooth, continuous transition from neck region 2004 to second end region 2006 throughout the range of lumen diameters of neck region 2004. Accordingly, first connection 2003 and second connection 2005 provides smooth, continuous transitions between the respective components as first end region 2002 and second end region 2006 transitions between their collapsed delivery states and expanded deployed states, for any given lumen diameter of neck region 2004.

In some embodiments, neck region 2004 may be treated in a non-uniform manner. For example, a center portion of neck region 2004 may be treated to produce a martensitic phase at body temperature and an Af temperature of, e.g., around 40-50° C. or 42° C., while the end portions of neck region 2004 that are to be fixedly coupled to the superelastic first and second end regions 2002, 2006 may be treated to produce an intermediate phase between martensite and austenite, e.g., an R-phase, at body temperature. In this embodiment, there may be a more gradual change in response to manipulation of the device, such as by mechanical expansion or thermal contraction of the shape-memory neck region, resulting in a smooth, continuous transition between the connected components.

Figure 21C:
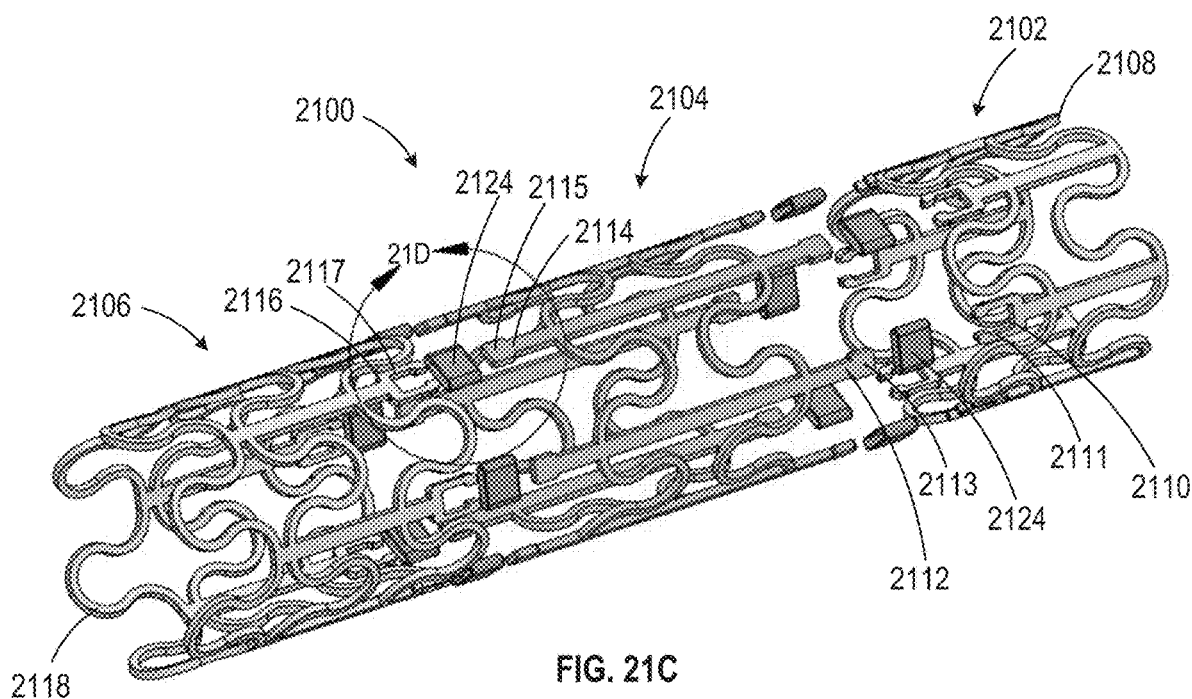
FIGS. 21C and 21D illustrate the device of FIGS. 21A and 21B in an unassembled configuration.
Figure 21D:
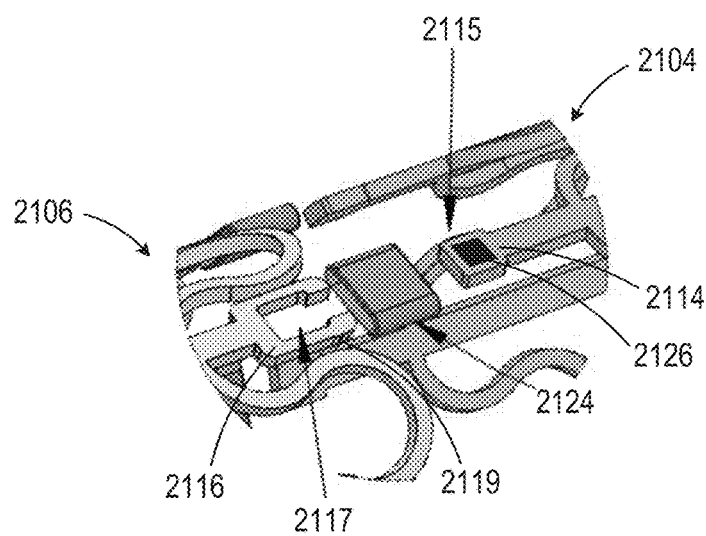

Referring now to FIGS. 21A-21D, another hybrid shunt device having interlocking components with different shape-memory properties that are treated separately and assembled together is provided. FIGS. 21A and 21B illustrate hybrid shunt 2100 in an assembled configuration, and FIGS. 21C and 21D illustrate hybrid shunt 2100 in an unassembled configuration, e.g., after the separate components have been treated to achieve the desired material properties. For example, shunt 2100 may be formed of first end region 2102, neck region 2104, and second end region 2106. As described above, neck region 2104 may be treated such that it is malleable at body temperature, e.g., having an Af temperature between about 40-60° C., and first end region 2102 and second end region 2106 may be treated such that they are superelastic at body temperature, e.g., having an Af temperature between about 5-20° C. In some embodiments, like neck region 2004, neck region 2104 may be treated in a non-uniform manner.

As shown in FIG. 21C, first end region 2102 may include proximal end 2108 and distal end 2110 having a plurality of first end region connectors 2111, neck region 2104 may include proximal end 2112 having a plurality of proximal neck region connectors 2113 and distal end 2114 having a plurality of distal neck region connectors 2115, and second end region 2106 may include proximal end 2116 having a plurality of second end region connectors 2117 and distal end 2118. Like device 2000 of FIGS. 20A-20F, each of first end region 2102, neck region 2104, and second end region 2106 may be formed of a plurality of longitudinal extending struts interconnected via one or more circumferentially extending sinusoidal rings. For example, as shown in FIGS. 21A and 21C, first end region 2102 may include a plurality of longitudinal struts 2120a interconnected via sinusoidal rings 2122a, such that the plurality of first end region connectors 2111 are disposed at distal end 2110 of each of longitudinal struts 2120a.

Neck region 2104 may include a plurality of longitudinal struts 2120b interconnected via sinusoidal rings 2122b, such that the plurality of proximal neck region connectors 2113 are disposed at proximal end 2112 of each of longitudinal struts 2120b and the plurality of distal neck region connectors 2115 are disposed at distal end 2114 of each of longitudinal struts 2120b. Second end region 2106 may include a plurality of longitudinal struts 2120c interconnected via sinusoidal ring 2122c, such that the plurality of second end region connectors 2117 are disposed at proximal end 2116 of each of longitudinal struts 2120c. As will be understood by a person having ordinary skill in the art, although FIGS. 21A and 21B illustrate first end region 2102 having two sinusoidal rings and second end region 2106 having three sinusoidal rings, first end region 2102 may include less or more than two sinusoidal rings interconnecting plurality of longitudinal struts 2120a, and second end region 2106 may each include less or more than three sinusoidal rings interconnecting plurality of longitudinal struts 2120c. Similarly, although FIGS. 21A and 21B illustrate neck region 2104 having two sinusoidal rings, neck region 2104 may have less or more than two sinusoidal rings interconnecting plurality of longitudinal struts 2120b. Moreover, shunt 2100 may include less or more longitudinal struts than is illustrated in FIGS. 21A and 21C.

Like the connectors of shunt 2000, each connector of the plurality of first end region connectors 2111 of first end region 2102 may have a shape configured to interlock with a complementary shape of each connector of the plurality of proximal neck region connectors 2113 of neck region 2104, and each connector of the plurality of second end region connectors 2117 of second end region 2106 may have a shape configured to interlock with a complementary shape of each connector of the plurality of distal neck region connectors 2115 of neck region 2104. For example, the complementary shapes of first end region connectors 2111 and proximal neck region connectors 2113, and second end region connectors 2117 and distal neck region connectors 2115 may include tab and socket elements. As shown in FIG. 21D, second end region connectors 2117 may include a socket element and distal neck region connectors 2115 may include a tab element. Similarly, proximal neck region connectors 2113 may include a tab element and first end region connectors 2111 may include a socket element. As will be understood by a person having ordinary skill in the art, first end region connectors 2111 and second end region connectors 2117 alternatively may include a tab element, whereas proximal neck region connectors 2113 and distal neck region connectors 2115 include a socket element.

As shown in FIG. 21D, socket element 2117 includes an opening sized and shaped to receive tab element 2115. Unlike the tab and socket elements of shunt 2000, tab element 2115 may be fitted within the opening of socket element 2117 without thermally contracting tab element 2115 or thermally expanding socket element 2117. Instead, when tab element 2115 is disposed within the opening of socket element 2117, retaining ring 2124 may be disposed over both tab element 2115 and socket element 2117 to thereby maintain the rigid connection between neck region 2104 and second end region 2106 at second connection 2105, as shown in FIG. 21B, while providing a smooth, continuous transition from neck region 2104 to second end region 2106 throughout the range of lumen diameters of neck region 2104. Similarly, when tab element 2113 at proximal end 2112 of neck region 2104 is disposed within the opening of socket element 2111 at distal end 2110 of first end region 2102, retaining ring 2124 may be disposed over both tab element 2113 and socket element 2111 to thereby maintain the rigid connection between neck region 2104 and first end region 2102 at first connection 2103, while providing a smooth, continuous transition from neck region 2104 to first end region 2102 throughout the range of lumen diameters of neck region 2104. Accordingly, first end region 2102 and second end region 2106 may bend uniformly relative to neck region 2104 as a single element would. In some embodiments, retaining rings 2124 may be made from radiopaque materials such that they are visible under fluoroscopy.

Moreover, the shunt devices described herein further may include one or more physiologic sensors, e.g., pressure sensors configured to acquire intra-atrial pressure measurements. For example, shunt 2100 may include one or more pressure sensors disposed at first connections 2103, e.g., for measuring pressure in a first atrium of the patient's heart, and/or at second connection 2105, e.g., for measuring pressure in a second atrium of the patient's heart, such that the progression of the treatment may be continuously monitored. As shown in FIG. 21D, sensor 2126, e.g., a pressure sensor, may be disposed on, e.g., embedded within, one or more of tab elements 2115, such that sensor 2126 is enclosed within retaining ring 2124 when retaining ring 2124 is disposed over tab element 2115 and socket element 2117 at second connection 2105, as described above. Accordingly, retaining ring 2124 may form a hermetic biocompatible packaging that resists ingress of corrosive body fluids on the electronic components of sensor 2126, while minimizing residual internal stress on sensor 2126.

Sensor 2126 similarly may be disposed on one or more of tab elements 2113, such that sensor 2126 may be enclosed within retaining ring 2124 when retaining ring 2124 is disposed over tab element 2113 and socket element 2111 at first connection 2103. Accordingly, pressure measurements obtained by the sensor at first connections 2103, e.g., atrial pressure within a first atrium of the patient's heart, and pressure measurements obtained by the sensor at second connections 2105, e.g., atrial pressure within a second atrium of the patient's heart, may be used to calculate a pressure gradient across shunt 2100, between the first and second atria. For example, the sensors may be configured for telemetry and include circuitry for transmitting data between each other and/or to a receiver external to the patient's body for processing. Sensors 2126 may be configured to acquire other physiological measurements including, for example, flow, velocity, temperature, pH, or the concentration of certain chemical species, within one or both atria, e.g., for comparing the measurements across the shunt, as described above. For example, sensors 2126 may be constructed similar to the sensors described in U.S. Patent App. Pub. No. 2022/0151784 to Eigler, assigned to the assignee of the present application, the entire contents of which are incorporated by reference herein. Additionally, or alternatively, sensor 2126 may be disposed on, e.g., embedded within, retaining ring 2124 itself.

Like shunt 2000, each of first end region connectors 2111 may be permanently fixed to each of proximal neck region connectors 2113 along a single plane at first connection 2103, and each of second end region connectors 2117 may be permanently fixed to each of distal neck region connectors 2115 along a single plane at second connection 2105. Alternatively, each of first end region connectors 2111 and each of second end region connectors 2117 may be permanently fixed to each of proximal neck region connectors 2113 and each of distal neck region connectors 2115, respectively, in a staggered manner along the circumference of shunt 2100, such that stress is distributed to alternate sides of the connections, thus distributing the strain and producing a smoother transition between components.

Figure 22A:
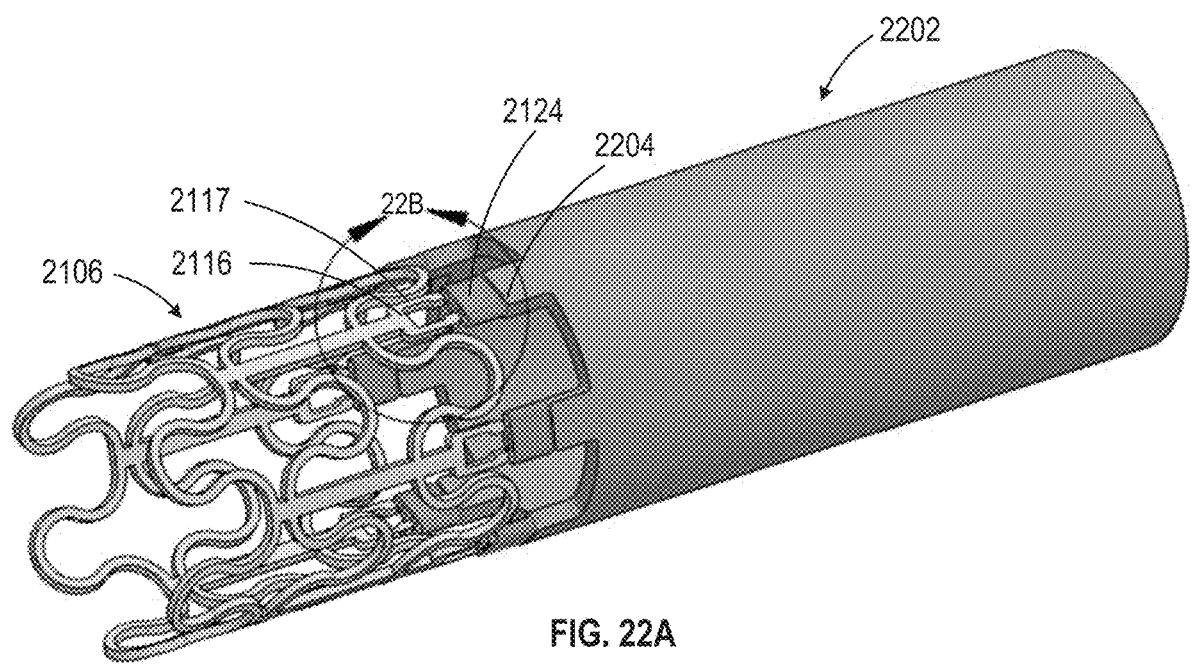
FIGS. 22A-22I illustrate an example method of assembling the device of FIGS. 21A and 21B.
Figure 22B:
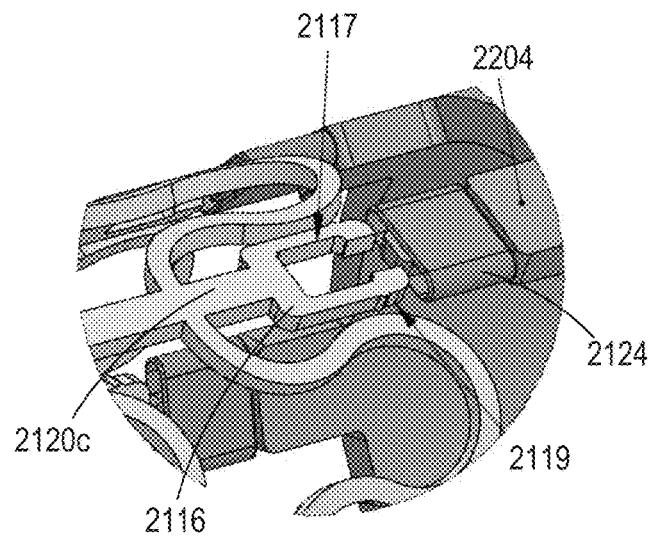
Figure 22C:
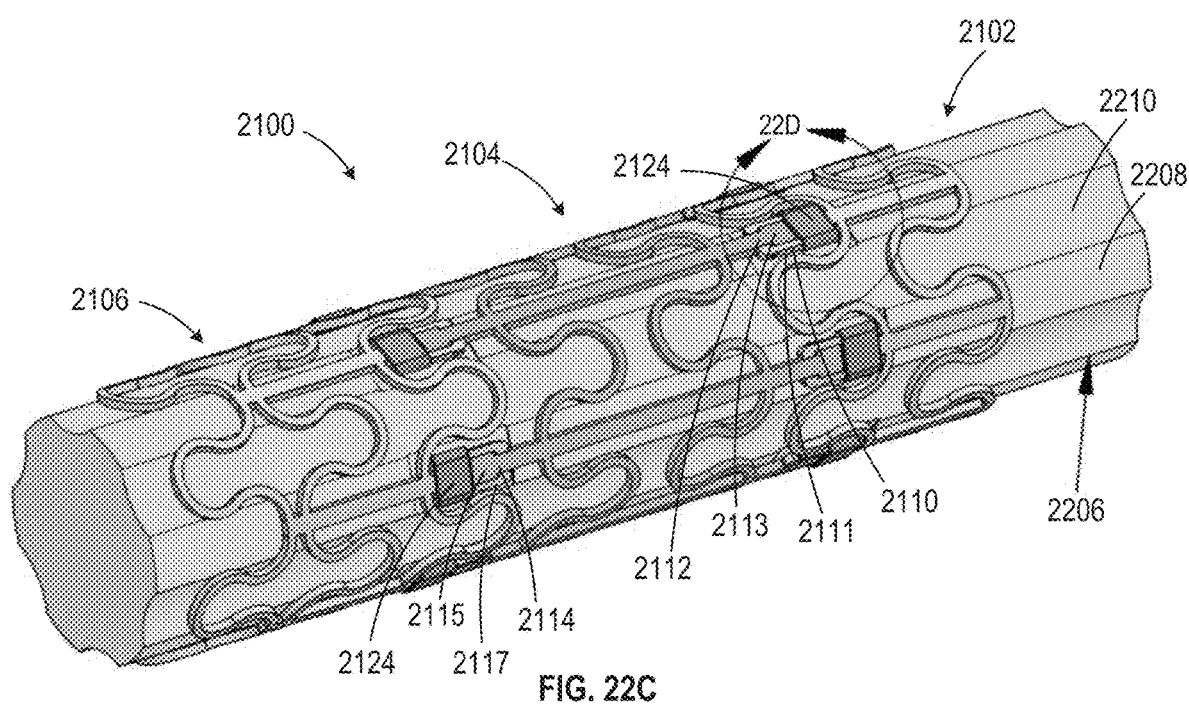
Figure 22D:
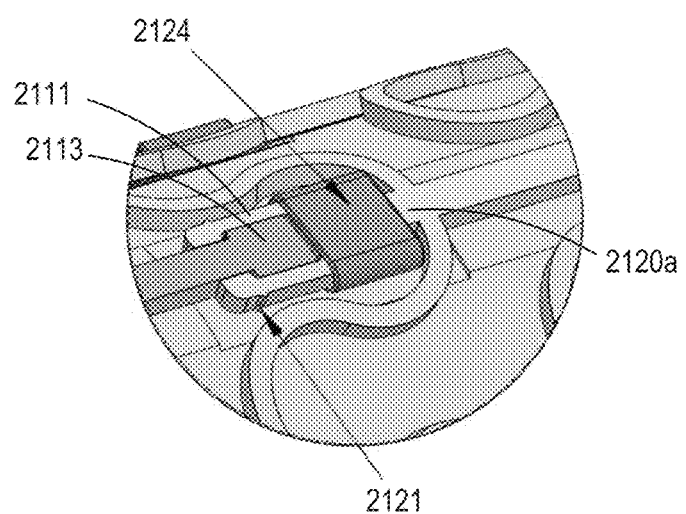

Referring now to FIGS. 22A-22I, an exemplary method for assembling the components of shunt 2100 is provided. First, retaining rings 2124 may be disposed over and beyond each connector of first end region 2102 and second end region 2106, e.g., first end region connectors 2111 and second end region connectors 2117, such that each retaining ring 2124 is temporarily disposed over longitudinal struts 2120a of first end region 2102 and longitudinal struts 2120c of second end region 2106 and the opening of the respective socket elements is exposed. For example, as shown in FIGS. 22A and 22B, retaining ring alignment tool 2202 may be used to slide each retaining ring 2124 over each second end region connector 2117. An end of retaining ring alignment tool 2202 may include one or more fingers 2204, each having an extended portion extending therefrom, sized and shaped to receive retaining ring 2124 thereon, and configured to align with a connector of the plurality of second end region connectors 2117, such that when aligned, retaining ring 2124 may easily be transferred from finger 2204 over connector 2117 and onto longitudinal strut 2120c, as shown in FIG. 22D.

In some embodiments, retaining ring alignment tool 2202 may have a number of fingers 2204 corresponding to the number of connectors of the plurality of second end region connectors 2117, as shown in FIG. 22A, such that each retaining ring 2124 may be deposited over each connector of second end region 2106 simultaneously as a group, or individually. Retaining ring alignment tool 2202 may similarly be used to slide each retaining ring 2124 over each first end region connector 2111. In addition, as shown in FIG. 22B, the outer surface of each socket element 2117, e.g., the lateral sides of the fingers of socket element 2117 defining the opening of socket 2117, may include one or more protrusions 2119 extending outwardly therefrom to facilitate securement of retaining ring 2124 to tab element 2115 and socket element 2117 when tab element 2115 is disposed within the opening of socket element 2117, e.g. via interference fit. When tab element 2115 is not disposed within socket element 2117, the fingers of socket element 2117 may be pushed inward towards each other, e.g., as retaining ring 2124 is moved over socket element 2117, via engagement between protrusions 2119 and the inner surface of retaining ring 2124.

As shown in FIGS. 22C and 22D, the components of shunt 2100 may then be assembled together over alignment pin 2206. Alignment pin 2206 may include a plurality of ridges 2208 extending longitudinally along the outer surface of alignment pin 2206, each ridge 2208 spaced apart circumferentially about the outer surface of alignment pin 2206 and separated by a plurality of grooves 2210. The position of ridges 2208 on alignment pin 2206 may correspond with the longitudinal struts of shunt 2100, as shown in FIG. 22C, to thereby provide support to the points of connection between the components of shunt 2100. As shown in FIG. 22C, tab elements 2113 of neck region 2104 may be fitted within the opening of socket elements 2111 of first end region 2102 when retaining rings 2124 are disposed over the longitudinal struts of first end region 2102, and tab elements 2115 of neck region 2104 may be fitted within the opening of socket elements 2117 of second end region 2106 when retaining rings 2124 are disposed over the longitudinal struts of second end region 2106. FIG. 22D illustrates tab element 2113 of neck region 2104 disposed within the opening of socket element 2111 having protrusions 2121 while retaining ring 2124 is disposed over longitudinal strut 2120a of first end region 2102.

Figure 22E:
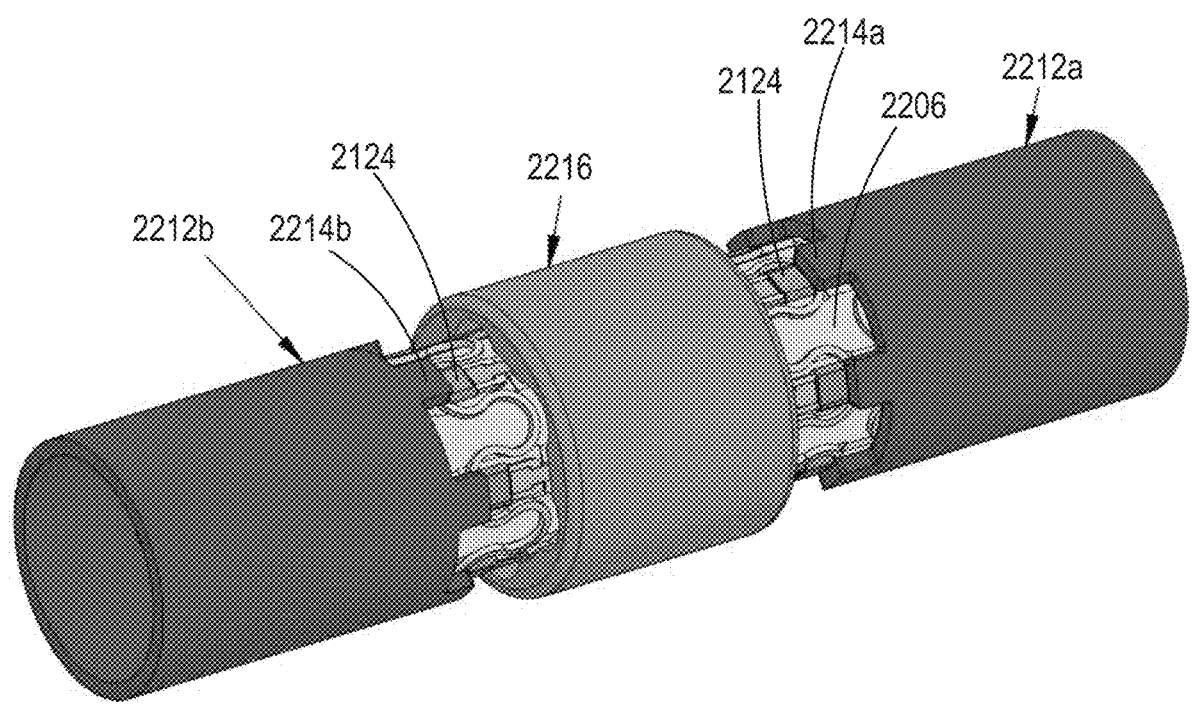
Figure 22F:
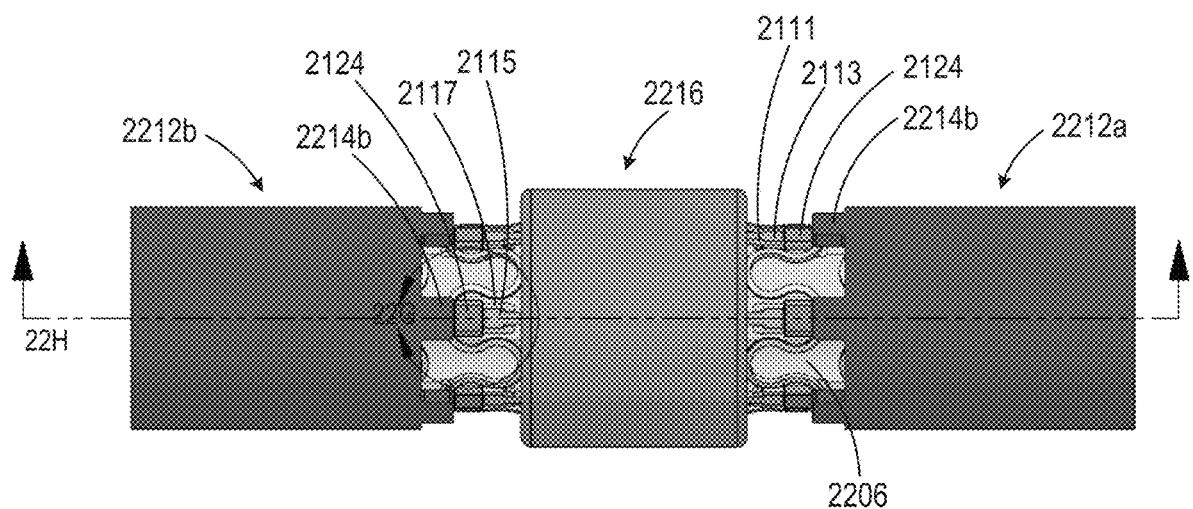

Next, each retaining ring 2124 may be moved such that they are disposed over the socket/tab connections. As shown in FIGS. 22E, 22F, and 22H, support ring 2216 having a lumen extending therethrough may be slid over shunt 2100 over alignment pin 2206 until support ring 2216 is positioned over the middle portion of neck region 2104. The inner surface of support ring 2216 may have a plurality of ridges and grooves, such that the position of the ridges correspond with the longitudinal struts of shunt 2100, as shown in FIG. 22E, to thereby provide additional support to the points of connection between the components of shunt 2100 along with ridges 2208 of alignment pin 2206 and prevent buckling of the frame of shunt 2100 as retaining rings 2124 are moved to their final position over the socket/tab connections.

Moreover, as shown in FIGS. 22E, 22F, and 22H, one or more seating rings 2212a, 2212b may be used to slide each retaining ring 2124 over each socket/tab connection between neck region 2104 and first and second end regions 2102, 2106. Accordingly, seating rings 2212a, 2212b may have a lumen extending therethrough sized and shaped such that seating rings 2212a, 2212b may be advanced over first and second end regions 2102, 2106 over alignment pin 2206. An end of each seating ring 2212a, 2212b may include one or more fingers 2214a, 2214b, respectively, each sized and shaped to be aligned with and engage with retaining ring 2124 as seating rings 2212a, 2212b are moved over first and second end regions 2102, 2106, respectively, towards neck region 2104 over alignment pin 2206.

Figure 22G:
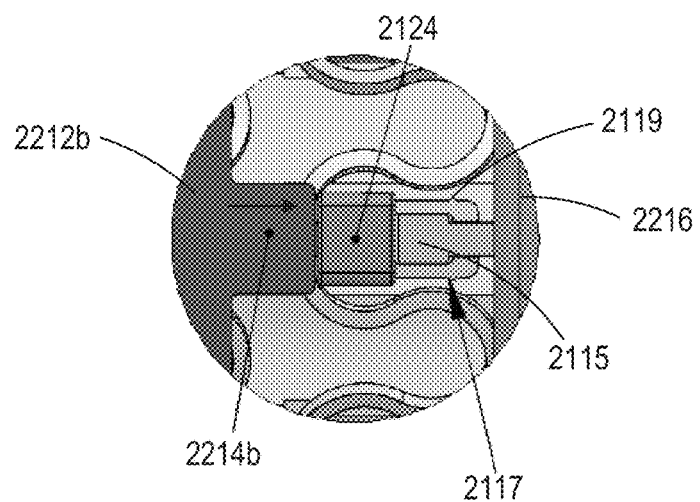
Figure 22H:
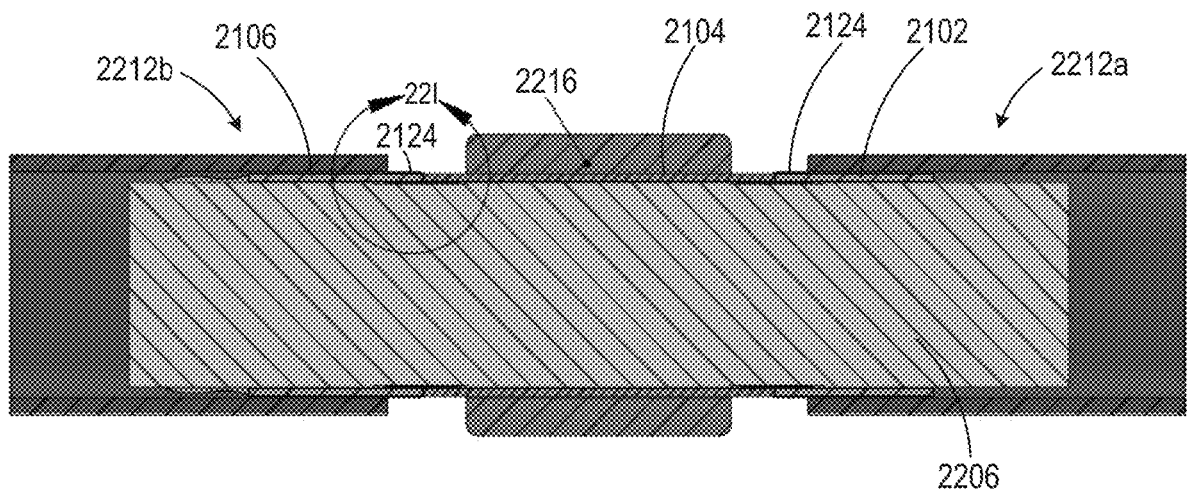
Figure 22I:
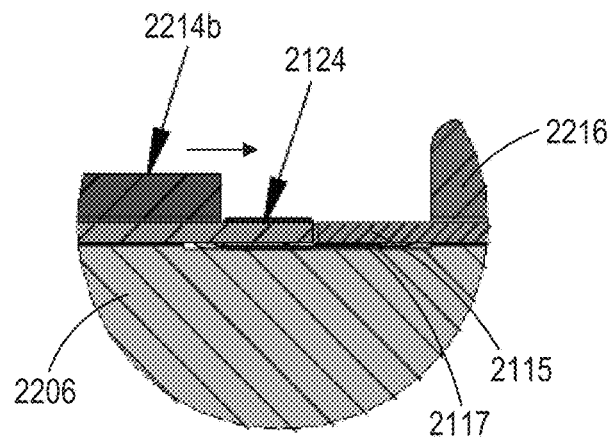

For example, as shown in FIGS. 22G and 22I, seating ring 2212b may be moved proximally over second end region 2106 over alignment pin 2206 in the direction of the arrow until finger 2214b contacts and engages with retaining ring 2124, such that further proximal movement of seating ring 2212b causes finger 2214b to push retaining ring 2124 over socket element 2217 and tab element 2115. As tab element 2115 is fitted within the opening of socket element 2117, the fingers of socket element 2217 defining the opening cannot move inward, and thus, protrusions 2119 exert a force against the inner surface of retaining ring 2124 when retaining ring 2124 is disposed thereon to facilitate securement of retaining ring 2124 over the socket/tab connection. As shown in FIG. 22I, retaining ring 2124 may have a very thin wall thickness to thereby provide a smooth, continuous transition from neck region 2104 to second end region 2106 as described above.

In some embodiments, seating ring 2212b may have a number of fingers 2214b corresponding to the number of connectors of the plurality of second end region connectors 2117, as shown in FIG. 22E, such that each retaining ring 2124 may be moved to its final position over the socket/tab connection simultaneously as a group, or individually. Seating ring 2212a may similarly be used to slide each retaining ring 2124 to its final position over each socket/tab connection between neck region 2104 and first end region 2102. Preferably, both seating rings 2212a, 2212b are pushed simultaneously to move the retaining rings to their final position over the respective socket/tab connections between neck region 2104 and first region 2102 and between neck region 2104 and second end region 2106. Alternatively, a single seating ring may be used to push the retaining rings over the first set of socket/tab connections at, e.g., at first connection 2103, and subsequently to push the remaining retaining rings over the second set of socket/tab connections at, e.g., at second connection 2105, or vice versa. As described above, an encapsulant may be disposed over shunt 2100, e.g., when retaining rings 2124 are in their final positions over the respective socket/tab connections, thereby further securing the retaining rings to shunt 2100. As will be understood by a person having ordinary skill in the art, hybrid shunts 2000, 2100 may be used in conjunction with the other features described herein, e.g., for acute treatment as described above with regard to FIGS. 15A-15E and/or bridge 1740 of FIGS. 17A-17E.

Figure 23B:
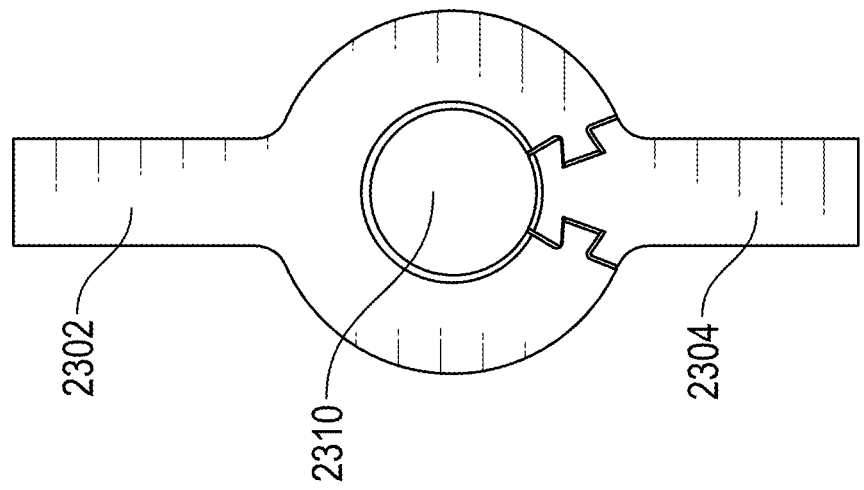
FIGS. 23A-23E illustrate alternative exemplary interlocking components of a hybrid shunt constructed in accordance with the principles of the present disclosure.
Figure 23A:
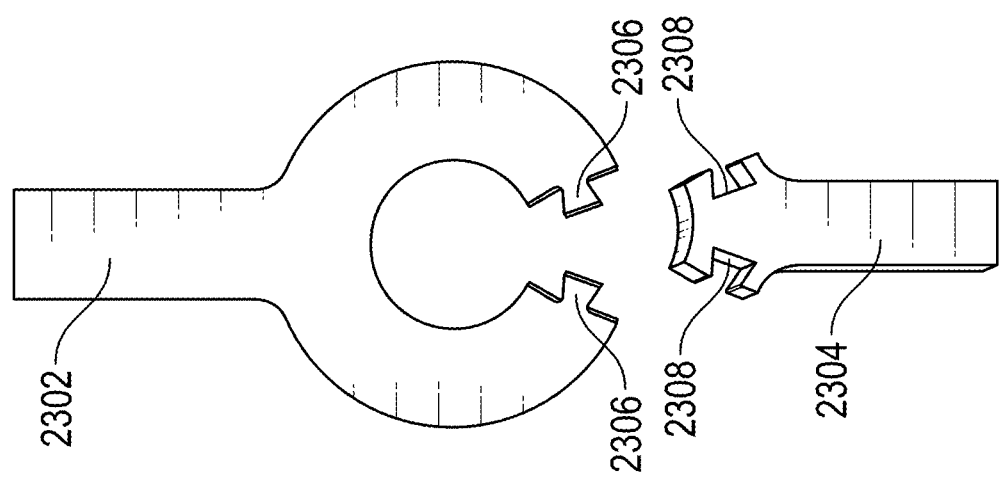

Referring now to FIGS. 23A to 23E, alternative exemplary interlocking components for permanently coupling separately treated regions of a hybrid shunt are provided. As shown in FIG. 23A, first interlocking component 2302, e.g., a first end region connector of a first end region of the hybrid shunt, may include a first geometry, e.g., one or more tab elements 2306, and second interlocking component 2304, e.g., a proximal neck region connector of a neck region of the hybrid shunt, may include a second geometry, e.g., one or more socket elements 2308, sized and shaped to complementarily receive one or more tabs 2306, as shown in FIG. 23B. As shown in FIG. 23A, tab elements 2306 may be disposed at the distal ends of a pair of fingers extending from a distal region of first interlocking component 2302 in a circular manner, such that the pair of fingers define a circular shaped opening therebetween. For example, the pair of fingers may initially extend away from each other, and then towards each other to thereby form the circular shaped opening. The inner surface of the circular shaped opening defined by the pair of fingers of first interlocking component 2302 may form at least a portion of eyelet 2310 when tab elements 2306 are disposed within socket elements 2308, as shown in FIG. 23B. Accordingly, the inner surface at the proximal end of second interlocking component 2304, e.g., the end facing towards first interlocking component 2302 when first interlocking component 2302 is coupled to second interlocking component 2304, may form the remaining portion of eyelet 2310 when tab elements 2306 are disposed within socket elements 2308, as shown in FIG. 23B.

Figure 23E:
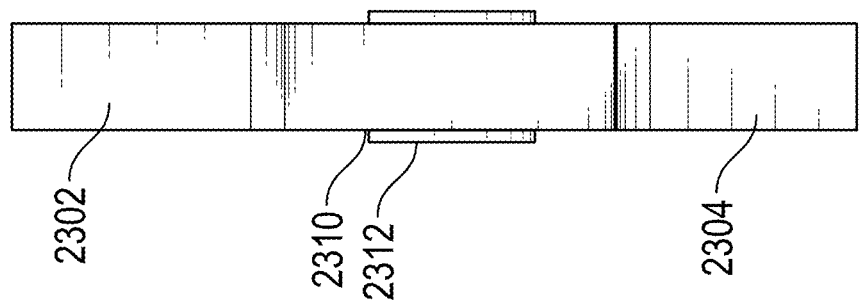
Figure 23D:
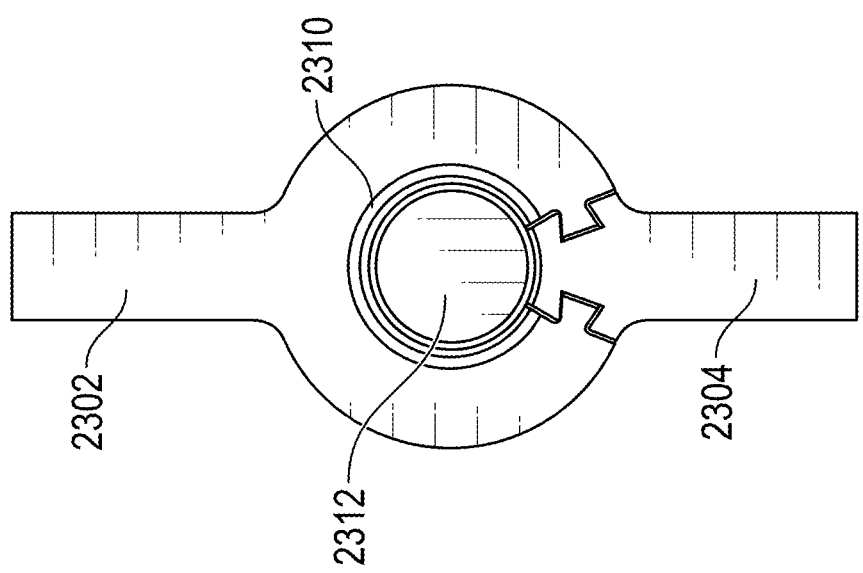
Figure 23C:
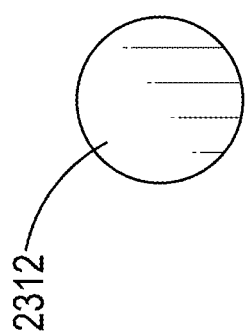

FIG. 23C illustrates a plug-like component, e.g., radiopaque marker 2312, sized and shaped to be tightly disposed within eyelet 2310 defined by first interlocking component 2302 and second interlocking component 2304 when tab elements 2306 are disposed within socket elements 2308. Radiopaque marker 2312 may be formed of, e.g., Tantalum, Platinum, Iridium etc., to thereby facilitate visualization under fluoroscopy. Moreover, radiopaque marker 2312 may have a geometry that is slightly larger than the geometry of eyelet 2310, such that, when radiopaque marker 2312 is disposed within eyelet 2310, radiopaque marker 2312 applies a mechanical force to first interlocking component 2302 and second interlocking component 2304 to thereby secure tab elements 2306 within socket elements 2308 and permanently fix first interlocking component 2302 to second interlocking component 2304, as shown in FIG. 23D. FIG. 23E is a side view of first interlocking component 2302 and second interlocking component 2304 when radiopaque marker 2312 is disposed within eyelet 2310. Thus, when radiopaque marker 2312 is disposed within eyelet 2310, tab elements 2306 and socket elements 2308 form a rigid connection that provides a smooth, continuous transition between the first end region and the neck region of the hybrid shunt, such that the first end region may bend uniformly relative to the neck region as a single element would. As will be understood by a person having ordinary skill in the art, eyelet 2310 may have a geometry other than a circle shape, such that radiopaque marker 2312 may have a corresponding shape configured to be tightly disposed within the eyelet. Alternatively, instead of a radiopaque marker, one or more of eyelets 2310 may have one or more physiologic sensors disposed therein. For example, as described above, the physiological sensors may be configured to acquire measurements including, for example, intra-atrial pressure measurements, flow, velocity, temperature, pH, or the concentration of certain chemical species.

As will be understood by a person having ordinary skill in the art, first interlocking component 2302 be may the proximal neck region connector of the neck region of the hybrid shunt, and accordingly, second interlocking component 2304 may be the first end region connector of the first end region of the hybrid shunt, such that the first end region and the neck region of the hybrid shunt may be permanently fixed together to form a rigid connection. Moreover, the second end region connector of the second end region of the hybrid shunt may have a geometry similar to the geometry of first interlocking component 2302 when the distal neck region connector of the neck region of the hybrid shunt may have a geometry similar to the geometry of second interlocking component 2304, or alternatively, the second end region connector of the second end region of the hybrid shunt may have a geometry similar to the geometry of second interlocking component 2304 when the distal neck region connector of the neck region of the hybrid shunt may have a geometry similar to the geometry of first interlocking component 2302.

Accordingly, provided herein is an interatrial shunt for placement at an atrial septum of a patient's heart for adjustably regulating fluid flow therethrough. The interatrial shunt may be configured similarly as one or more of device 200 described with reference to FIGS. 2A-2E; device 700 described with reference to FIGS. 7, 8A-8D, 9A-9B, and 10A-10C; device 28 described with reference to FIGS. 15A-15E; device 2000 of FIGS. 20A-20F; or device 2100 of FIGS. 21A-21D. For example, the interatrial shunt may include a body that includes first and second expandable end regions coupled in fluid communication by a neck region. The first expandable end region may be configured to be placed in a first atrium of the heart, the second expandable end region may be configured to be placed in a second atrium of the heart, and the neck region may be configured for placement at the atrial septum.

The body may include a shape-memory material, e.g., in a manner such as described elsewhere herein. The body may define a passageway through the neck region for blood to flow between a first atrium and a second atrium, e.g., in a manner such as device 700 described with reference to FIGS. 7, 8A-8D, 9A-9B, and 10A-10C; device 28 described with reference to FIGS. 15A-15E; device 2000 of FIGS. 20A-20F; or device 2100 of FIGS. 21A-21D. The first and second regions may be superelastic at body temperature, and the neck region may be malleable at body temperature, e.g., in a manner such as described elsewhere herein. A flow area of the passageway through the neck region may be adjusted in vivo, e.g., in a manner such as described elsewhere herein.

The neck region may be heat treated to exhibit different shape memory properties than the first and second expandable end regions such that a cross-sectional area of the passageway is adjustable in vivo. For example, the first and second expandable end regions that are superelastic may include NITINOL having an austenitic finish temperature (Af) between 5-20° C., e.g., in a manner such as described elsewhere herein. The neck region that is malleable may include NITINOL having an austenitic finish temperature (Af) between 40-60° C., e.g., in a manner such as described elsewhere herein. The neck region may be mechanically expandable, e.g., in a manner such as described elsewhere herein. The neck region may be thermally contractible, e.g., in a manner such as described elsewhere herein.

For example, the malleable shape-memory material may be configured to be expanded in vivo such that the passageway expands from the cross-sectional area to a second cross-sectional area larger than the cross-sectional area, e.g., in a manner such as described elsewhere herein. The malleable shape-memory material may be configured to be contracted in vivo such that the passageway contracts from the second cross-sectional area to a third cross-sectional area smaller than the second cross-sectional area, e.g., in a manner such as described elsewhere herein. The cross-sectional area may be between 4.9 to 28.3 mm$^2$ and the second cross-sectional area and the third cross-sectional area may be between 15.9 to 78.6 mm$^2$.

The malleable shape-memory material may include NITINOL having an austenitic finish temperature (Af) between 40-60° C., e.g., in a manner such as described elsewhere herein. The self-expanding superelastic material may include NITINOL having an austenitic finish temperature (Af) between 5-20° C., e.g., in a manner such as described elsewhere herein. The malleable shape-memory material may be mechanically expandable, e.g., in a manner such as described elsewhere herein. The malleable shape-memory material may be thermally contractible, e.g., in a manner such as described elsewhere herein. The cross-sectional area of the neck region may be smaller than respective cross-sectional areas of at least one of the first and second expandable end regions. The first and second expandable end regions may extend into the first and second atria, respectively, such that respective ends of the first and second expandable end regions may not contact the atrial septum. As described above, the first and second expandable end regions and the neck region may comprise a diabolo-shaped shunt. The first and second expandable end regions and the neck region may be integrally formed from a common frame, e.g., in a manner such as described elsewhere herein. Alternatively, the first and second expandable end regions and the neck region may be formed separately and assembled together, e.g., in a manner such as described elsewhere herein. The first and second expandable end regions and the neck region may be at least partially encapsulated with a biocompatible material, e.g., in a manner such as described elsewhere herein.

It will be appreciated that in any of the present examples, device configurations may be reversibly modified in vivo. In many examples, the configuration change includes increasing or decreasing a dimension of a device, such as an internal dimension of the device or an external dimension of the device. However, other configuration changes suitably may be implemented, such as those described in U.S. Pat. No. 6,964,680 to Shanley, entitled "Expandable medical device with tapered hinge," the entire contents of which are incorporated by reference herein.

While various illustrative embodiments of the invention are described above, it will be apparent to one skilled in the art that various changes and modifications may be made therein without departing from the invention. For example, although examples of the present devices are described as having two or three components, it should be understood that the present devices may include any suitable number of components that respectively include a self-expanding superelastic material or a malleable shape-memory material. The appended claims are intended to cover all such changes and modifications that fall within the true spirit and scope of the invention.

What is claimed:

1. A hybrid shunt comprising shape-memory material for placement at an atrial septum of a patient's heart, the hybrid shunt comprising:
a neck region configured to be malleable at body temperature;
a first end region configured to be superelastic at body temperature, a distal end of the first end region configured to be permanently fixed to a proximal end of the neck region at a first connection;
a second end region configured to be superelastic at body temperature, a proximal end of the second end region configured to be permanently fixed to with a distal end of the neck region at a second connection; and
a passageway extending through the first end region, the neck region, and the second end region for blood to flow across the atrial septum,
wherein a flow area of the passageway through the neck region is configured to be adjustable in vivo.

2. The hybrid shunt of claim 1, wherein the first and second end regions are not formed integrally with the neck region.

3. The hybrid shunt of claim 1, wherein the proximal and distal ends of the neck region comprise a shape configured to interlock with a complementary shape of the distal end of the first end region and the proximal end of the second end region, respectively.

4. The hybrid shunt of claim 3, wherein the complementary shapes of the proximal and distal ends of the neck region and the distal end of the first end region and the proximal end of the second end region comprise a tab element and a socket element.

5. The hybrid shunt of claim 4, wherein the tab element is configured to be thermally contracted or the socket element is configured to be thermally expanded such that the tab element fits within the socket element, and wherein, when the tab and socket elements are brought to a same temperature while the tab element is received within the socket element, the tab element and the socket element form a rigid connection.

6. The hybrid shunt of claim 4, further comprising a retaining ring configured to be disposed over the tab and socket elements when the tab element is fitted within the socket element to maintain a rigid connection between the tab and socket elements.

7. The hybrid shunt of claim 6, wherein an outer surface of the socket element comprises one or more protrusions, such that the retaining ring maintains the rigid connection between the tab and socket elements via interference fit between the one or more protrusions and an inner surface of the retaining ring.

8. The hybrid shunt of claim 6, further comprising a physiological sensor disposed on the tab element, such that the physiological sensor is enclosed within the retaining ring when the retaining ring is disposed over the tab and socket elements.

9. The hybrid shunt of claim 1, wherein the first and second end regions are configured to self-expand from a collapsed delivery state to an expanded deployed state at body temperature.

10. The hybrid shunt of claim 9, wherein, in the expanded deployed state, a proximal end of the first end region flares outwardly from the distal end of the first end region at the first connection, and a distal end of the second end region flares outwardly from the proximal end of the second end region at the second connection.

11. The hybrid shunt of claim 1, wherein the distal end of the first end region comprises a plurality of circumferentially spaced apart connectors configured to be permanently fixed to a corresponding plurality of circumferentially spaced apart connectors of the proximal end of the neck region at the first connection, and wherein the proximal end of the second end region comprises a plurality of circumferentially spaced apart connectors configured to be permanently fixed to a corresponding plurality of circumferentially spaced apart connectors of the distal end of the neck region at the second connection.

12. The hybrid shunt of claim 11, wherein the plurality of circumferentially spaced apart connectors of the distal end of the first end region and the proximal end of the neck region are permanently fixed along a single plane at the first connection, and
wherein the plurality of circumferentially spaced apart connectors of the proximal end of the second end region and the distal end of the neck region are permanently fixed along a single plane at the second connection.

13. The hybrid shunt of claim 11, wherein the plurality of circumferentially spaced apart connectors of the distal end of the first end region and the proximal end of the neck region are permanently fixed in a staggered manner at the first connection, such that the connections do not all lie in a single plane, and
wherein the plurality of circumferentially spaced apart connectors of the proximal end of the second end region and the distal end of the neck region are permanently fixed in a staggered manner at the second connection, such that the connections do not all lie in a single plane.

14. The hybrid shunt of claim 1, wherein the neck region comprises NITINOL having an austenitic finish temperature (Af) between 45-60° C.

15. The hybrid shunt of claim 1, wherein the neck region is configured to be mechanically expandable in vivo such that the passageway expands from a first cross-sectional area to a second cross-sectional area larger than the first cross-sectional area.

16. The hybrid shunt of claim 1, wherein the neck region is configured to be thermally contractible in vivo.

17. The hybrid shunt of claim 1, wherein the first and second end regions comprise NITINOL having an austenitic finish temperature (Af) between 5-20° C.

18. The hybrid shunt of claim 1, wherein the first and second end regions and the neck region comprise a diabolo-shaped shunt.

19. The hybrid shunt of claim 1, wherein the first and second end regions and the neck region are at least partially encapsulated with a biocompatible material.

20. The hybrid shunt of claim 1, further comprising a bridge extending from a first outer surface of the first end region to a second outer surface of the second end region, the bridge formed of biocompatible material and configured to engage the patient's atrial septum.

21. The hybrid shunt of claim 20, wherein the first and second end regions and the neck region are at least partially encapsulated with a biocompatible material integrally formed with the bridge.

22. The hybrid shunt of claim 20, wherein the first and second end regions and the neck region are at least partially encapsulated with a biocompatible material different from the biocompatible material of the bridge.

23. The hybrid shunt of claim 22, wherein the biocompatible material of the bridge is configured to permit tissue ingrowth and the biocompatible material of the encapsulation is configured to inhibit tissue ingrowth.

24. The hybrid shunt of claim 22, wherein the biocompatible material of the bridge has an internodal distance greater than the internodal distance of the biocompatible material of the encapsulation.

25. The hybrid shunt of claim 24, wherein the internodal distance of the bridge material is selected to permit tissue ingrowth while the internodal distance of the encapsulation material is selected to inhibit tissue ingrowth.

26. The hybrid shunt of claim 24, wherein the biocompatible material of the bridge and the biocompatible material of the encapsulation are expanded polytetrafluoroethylene (ePTFE).

27. The hybrid shunt of claim 20, wherein the biocompatible material of the bridge comprises a porosity selected to permit tissue ingrowth.

28. The hybrid shunt of claim 20, wherein the bridge is configured to remain engaged with the patient's atrial septum when the neck region is contracted.

29. The hybrid shunt of claim 1, further comprising one or more physiological sensors disposed at the first and/or second connections.

30. The hybrid shunt of claim 29, wherein the one or more physiological sensors are configured to measure at least one of pressure, flow, velocity, temperature, or pH.

* * * * *